US007951382B2

(12) United States Patent
Gelber et al.

(10) Patent No.: US 7,951,382 B2
(45) Date of Patent: May 31, 2011

(54) METHODS FOR TREATMENT OF TYPE 2 DIABETES

(75) Inventors: Cohava Gelber, Nokesville, VA (US); Liping Liu, Manassas, VA (US); Zhidong Xie, Manassas, VA (US); Pranvera Ikonomi, Manassas, VA (US); John R Simms, Haymarket, VA (US); Catherine R Auge, Haymarket, VA (US)

(73) Assignee: American Type Culture Collection, Manassas, VA (US)

( * ) Notice: Subject to any disclaimer, the term of this patent is extended or adjusted under 35 U.S.C. 154(b) by 0 days.

(21) Appl. No.: 12/759,072

(22) Filed: Apr. 13, 2010

(65) Prior Publication Data

US 2010/0197596 A1    Aug. 5, 2010

Related U.S. Application Data

(60) Division of application No. 12/319,883, filed on Jan. 12, 2009, now abandoned, which is a continuation-in-part of application No. 11/901,925, filed on Sep. 18, 2007, now abandoned, which is a continuation-in-part of application No. PCT/US2007/007875, filed on Mar. 28, 2007.

(60) Provisional application No. 60/841,717, filed on Sep. 1, 2006.

(51) Int. Cl.
*A61K 38/17* (2006.01)

(52) U.S. Cl. ..................... 424/198.1; 530/300

(58) Field of Classification Search .................. None
See application file for complete search history.

(56) References Cited

U.S. PATENT DOCUMENTS

| 4,230,767 A | 10/1980 | Isaka et al. |
| 4,233,402 A | 11/1980 | Maggio et al. |
| 4,275,149 A | 6/1981 | Litman et al. |
| 4,376,110 A | 3/1983 | David et al. |
| 4,522,811 A | 6/1985 | Eppstein et al. |
| 4,659,678 A | 4/1987 | Forrest et al. |
| 4,699,880 A | 10/1987 | Goldstein |
| 4,727,022 A | 2/1988 | Skold et al. |
| 5,744,305 A | 4/1998 | Fodor et al. |
| 7,255,988 B2 | 8/2007 | Halle et al. |
| 7,648,825 B2 | 1/2010 | Ellis et al. |
| 2004/0224304 A1 | 11/2004 | Berggren |
| 2007/0059722 A1 | 3/2007 | Salonen et al. |

FOREIGN PATENT DOCUMENTS

| EP | 0125023 | 11/1984 |
| EP | 0171496 | 2/1986 |
| EP | 0173494 | 3/1986 |
| EP | 0184187 | 6/1986 |
| EP | 1615035 | 1/2006 |
| JP | 2003235573 | 8/2003 |
| WO | 86/01533 | 3/1986 |
| WO | 87/02671 | 5/1987 |
| WO | 03/014151 A2 | 2/2003 |
| WO | 2004/084797 A2 | 10/2004 |
| WO | 2005/055956 | 6/2005 |
| WO | 2008/030273 | 3/2008 |
| WO | 2009/038689 | 3/2009 |

OTHER PUBLICATIONS

Antibody Directory (2006), Antichymotrypsin, 3 pages.
Belagaje et al. (1979) The Journal of Biochemistry 254:5765-5780.
Better et al. (1988), Science 240:1041-1043.
Boulianne et al. (1984), Nature 312:643-646.
Budde et al. (2005), Combinatorial Chemistry & High Throughput Screening 8:775-781.
Burke et al. (1999), Arch. Intern. Med. 159:1450-1456.
Cabilly et al. (1984) Proc. Natl. Acad. Sci. USA 81:3273-3277.
Chater et al. (1986) In: Sixth International Symposium on Actinomycetales Biology, Akademiai Kaido, Budapest, Hungary pp. 45-54.
DeLong et al. (1988) Biometrics 44:837-845.
Eddy et al. (2003) Diabetes Care 26:3102-3110.
Eddy et al. (2003) Diabetes Care 26:3093-3101.
Glover (1985) ed. DNA Cloning vol. II. pp. 143-238, IRL Press.
Glover (1985) ed. DNA Cloning vol. II. pp. 45-66, IRL Press.
Gorman et al. (1982) Proc. Natl. Acad. Sci. USA 79:6777-6781.
Griffin et al., (2000) Diabetes Metabolism Research and Reviews, 16:164-171.
Grosschedl et al. (1985) Cell 41:885-897.
Gryczan (1982), Academic Press, NY, pp. 307-329.
Hanson et al. (2002) Diabetes 51:3120-3127.
Horvath et al. (2004) Journal of Molecular Evolution 59:488-497.
Hu et al. (2004) Diabetes 53:693-700.
Izaki (1978), Jpn. J. Bacteriol. 33:729-742.
John et al. (1986) Reviews of Infectious Diseases 8:693-704.
Johnston et al. (1988) Science 203:614-625.
Kannel et al. (1976) The American Journal of Cardiology 38:46-51.
Kendall et al. (1987) Journal of Bacteriology 169:4177-4183.
Khorana (1979) Science 203:614-625.
Kohler et al. (1975) Nature 256:495-497.
Kozbor et al. (1983) Immunology Today 4:72-79.
Lathe et al. (1985) J. Molec. Biol. 183:1-12.
Lindström (2003) Diabetes Care 26:725-731.
Liu et al. (1987) The Journal of Immunology 139:3521-3526.
Liu et al. (1987) Proc. Natl. Acad. Sci. USA 84:3439-3443.
Marks et al. (1993) Bio/Technology 11:1145-1149.
Meigs et al. (2004) JAMA 291:1978-1986.
Miller et al. (1989) Bio/Technology 7:698-704.
Mischak et al. (2004) Clinical Science 107:485-495.
Morrison et al. (1984) Proc. Natl. Acad. Sci. USA 81:6851-6855.
Muller (1983) Methods in Enzymology 92:589-601.
Neuberger et al. (1985) Nature 314:268-270.
Nyyssönen et al. (1993) Bio/Technology 11:591-595.

(Continued)

*Primary Examiner* — Ruixiang Li
(74) *Attorney, Agent, or Firm* — Nixon Peabody LLP

(57) ABSTRACT

The present invention relates generally to the identification of biological markers associated with an increased risk of developing Diabetes, as well as methods of using such biological markers in diagnosis and prognosis of Diabetes. The biological markers of the invention may indicate new targets for therapy or constitute new therapeutics for the treatment or prevention of Diabetes.

6 Claims, 23 Drawing Sheets

OTHER PUBLICATIONS

O'Marcaigh et al. (1993) Clinical Pediatrics 32:485-491.
Okayama et al. (1983) Mol. Cell. Biol. 3:280.
Potter et al. (1984) Proc. Natl. Acad. Sci. USA 81:7161.
Sabin et al. (1989) BioTechnology 7:705-709.
Sahagan et al. (1986) The Journal of Immunology 137:1066-1074.
Shultz (1996) Clinical Interpretation of Laboratory Procedures, pp. 192-199.
Stefan et al. (2006) Diabetes Care 29:853-857.
Stern et al. (1984) American Journal of Epidemiology 120:834-851.
Stern et al. (1993) Diabetes 42:706-714.
Sun et al. (1987) Proc. Natl. Acad. Sci. USA 84:214-218.
UniProtKB/Swiss-Prot P0100 (1991) Serpina3, 8 pages.
UniProtKB/Swiss-Prot Q63556 (1996) Serpina3M, 4 pages.
Velculescu et al. (1995) Science 270:484-487.
Wahl et al. (1983) The Journal of Nuclear Medicine 24:316-325.
Weidle et al. (1987) Gene 51:21-29.
Whittle et al. (1987) Protein Engineering 1:499-505.
Wirth et al. (2002) Proteomics 2:1445-1451.
Wu et al. (1978) Prog. Nucl. Acid Res. Molec. Biol. 21:101-141.
Yoshikawa et al. (1986) Jpn. J. Cancer Res. 77:1122-1133.
Zweig et al. (1992) Clinical Chemistry 38:1425-1428.

| SEQ ID | | | SEQUENCE | IDENTITY | | ACCESSION NR. |
|---|---|---|---|---|---|---|
| 1 | 38AA, A3M | | SGRPPMIVWFNRPFLIAVSHTHGQTILFMAKVINPVGA | 38/38 | (100%) | AAH03559 |
| 8 | SERPINA3 | | ------IVRFNRPFLMIIVPTDTQNIFFMSKVTNPKQA | 17/38 | (44.7%) | AAT08029 |
| 9 | GIP25 | | ------IV-FNRPFLMIIVPTDTQNIFFMSKVTNPKQA | 17/38 | (44.7%) | CAA25459 |
| 10 | UNKNOWN1 | | ------IV-FNRPFLMIIVPTDTQNIFFMSKVTNPKQA | 17/38 | (44.7%) | AAA51546 |
| 11 | A1AT | | ---PP--V-FNKPFVFLMIEQNTKSPLFMGKVVNPTQK | 15/38 | (39.5%) | AAA59454 |
| 12 | KALLISTATIN | | ---------I-FNRPFLVVIFSTSTQSVLFLGKVVDPTKP | 13/38 | (34.2%) | CAD66567 |
| 13 | UNKNOWN2 | | ---------I-FNRPFLVVIFSTSTQSVLFLGKVVDPTKP | 13/38 | (34.2%) | AF113676 |
| 14 | PRO684 | | ------P----FNKPFVFLMIEQNTKSPLFMGKVVNPTQK | 13/38 | (34.2%) | XP_945171 |
| 15 | A1AT LIKE | | ---------FNRPFLVIIKDDITNFPLFIGKVVNPTQK | 12/38 | (31.6%) | CAD62587 |
| 16 | UNKNOWN3 | | ---------FNRPFLLLLWEVTTQSLLFLGKVVNPVAG | 12/38 | (31.6%) | EAW90971 |
| 17 | ATIII -LIKE | | ---------ANRPFLVFIREVPLNTIIFMGRVANPCVK | 12/38 | (31.6%) | |

FIG. 3A

| SEQ ID | | | | Genebank |
|---|---|---|---|---|
| | | I | V R F N R P F L M I I V P T D | |
| 18 SERPINA3 | 1204 | TGCATTAGTGGAGACAA---GGACCAT------- | TGTGCGTTCAACAGGCCCTTCTGATCATCATTGTCCCTACAGACA | BC003559 |
| 19 GIP25 | 1179 | TGCATTAGTGGAGAGA CAA---GGACCAT------- | TGTGCGTTCAACAGGCCCT TCCTGATGATCATTGTCCCT ACAGACA | AY513276 |
| 20 UNKNOWN1 | 540 | TGCATTAGTGGAGACAA---GGACCAT------- | TGTGCGTTCAACAGGCCCT TCCTGATGATCATTGTCCCT ACAGACA | X00947 |
| 21 A1AT | 1165 | CCCCAGAG-----GTCAA------- | TTCAACAAACCCTTGTCTTCTTAATGATTGAACAAAATA | M11465 |
| 22 KALLISTATIN | 1167 | TGC-------CCAGACCAATCGCCACAT------- | CCTGCGGA TTCAACCGGCCCTGTGGTGATCTTTTCCACCAGCA | L19684 |
| 23 UNKNOWN2 | 1222 | TGC-------CCAGACCAATCGCCACAT------- | CCTGCGGA TCCAACCGGCCCTGTGGTGATCTTTTCCACCAGCA | BX248760 |
| 24 PRO0684 | 2257 | T---------ATCC---CCCCCGA | GGTCAAGTTCAACAAACCCTTTGTCTTCTTAATGATTGAACAAAATA | AF113676 |
| 25 A1AT LIKE | 1303 | AGTATCAG---------AC------- | AGTCATGTTCAACCGGCCCTTCCTGGTCATCA---TCAAGGATGACA | XM_940078 |
| 26 UNKNOWN3 | 1199 | CCCATCTCTGAACACCA---TGTCAGACCACCATGCCCA | CTTCAACACGGCC TTTCCTCTTGCCTCCTTTGGGAGTCACCA | BX248259 |
| | | T Q N I F F M S K V T N P K Q A | |
| 18 SERPINA3 | 1275 | CCAGAACATCT----TCTTCATGAGCAAAGTCAAAGTCAAAGT----CCCAAGCAAGCAAGCTTGAGCTTGC | ----CATC------A |
| 19 GIP25 | 1250 | CCC AGAACATCT----TCTTCATGAGCAAAGTCAAAGTCACC AATCCCAAGCAAGCCAAG AGCTTGC | ----CATC------A |
| 20 UNKNOWN1 | 611 | CCAGAACATCT----TCTTCATGAGCAAAGTCAAAGTCACC AATCCCAAGCAAGCCAAG AGCTTGC | ----CATC------A |
| 21 A1AT | 1219 | CCAAGTCTCCCC----TCTTTCATGGGCAAAGTCGTCGACCCCGAAACCATAG | --------------- |
| 22 KALLISTATIN | 1235 | CCAGAGTGTCC----TCTTTCTGGGCAAGGTCGTCGACCCCACGAAACCATAG | --------------- |
| 23 UNKNOWN2 | 1290 | CCCAGAGTGTCC----TCTTTCTGGGCAAGGTCGTCGACCCCACGAAACCATAG | --------------- |
| 24 PRO0684 | 2316 | CCAAGTCTCC CC----TCTTCATGGGCAAAAGTGGTGAATCCCAA | --------------- |
| 25 A1AT LIKE | 1357 | TCACCAACTTTCCGC TCTTCATTGGAAAAGTGGTGAATCCCACCCAA | --------------- |
| 26 UNKNOWN3 | 1276 | CCCAGAGCTTAC----TCTTCCTGGGAAAAGTGTCAACC | --------------- |

FIG. 3B

| Protein origin | Number | Peptide Name | Peptide Sequence |
|---|---|---|---|
| 34867677 | 1 | ATCC D1 | IVWFNRPFLIAVSH [SEQ ID NO: 27] |
| | 2 | ATCC D2 | HGQTILFMAKVI [SEQ ID NO: 28] |
| | 3 | ATCC D3 | SGRPP MIVWF NRPFL IAVSH THGQT ILFMA KVINP VGA [SEQ ID NO: 1] |

Location of the peptides within the protein:

/translation="MAFIAALGLLMAGICPAVLGFPDGTLGNDTLLHKDQDKGTQLDS
LTLESINTDFAFSLYKMLALKNPDKNVFSPLSISAALAIVSLGAKGNTLEEILEVLR
FNLTESYETDIHQGFGHLLQRLSQPGDQVKIITGNALFIDKNLQVLAEFQEKTRALYQ
VEAFTADFQQPRVTEKLINDYVRNQTQGKIQELVSGLKERTSMVLVNYLLFRGKWKVP
FDPDYTFESEFYVDEKRSVKVSMMKIEELTTPYFRDEELSCSVLELKYTGNSSALFIL
PDKGRMQQVEASLQPETLKKWKDSLRPRKIDELYLPRLSISTDYSLEEVLPELGIRDV
**FSQQADLSRITGAKDLSVSQVVHKVVLDVNETGTEAAATGANLVPRSGRPPMIVWFN
RPFLIAVSHTHGQTILFMAKVINPVGA**" (SEQ ID NO: 3)

*FIG. 4A*

| Transcript | Fold Changes | | | | | |
|---|---|---|---|---|---|---|
| | Resistance | | | Progression | | |
| | Day 10 | Day 30 | Increase (fold) | Day 10 | Day 30 | Decrease (%) |
| Steap1 | 3.3 | 6.6 | 200% | -2.8 | -9.7 | 346% |
| Ccl5 | 5.2 | 7 | 135% | -2.7 | -8.9 | 330% |
| Rn164935 | 1.4 | 7.3 | 521% | -1 | -6.6 | 660% |
| Rn171055 | 1.5 | 7.6 | 507% | -0.7 | -7.3 | 1043% |
| RGD1563547 | 1.2 | 7.9 | 658% | -1.3 | -10 | 769% |
| Rn164640 | 1.9 | 8 | 421% | -1.2 | -8.7 | 725% |
| Slc7A | 1.7 | 9.8 | 576% | -1.6 | -3.4 | 213% |
| Ocln | 2.6 | 10.2 | 392% | -1.2 | -8.3 | 692% |
| Scd2 | 1.7 | 10.2 | 600% | -0.5 | -6.2 | 1240% |
| Pfkp | 1.4 | 11.2 | 800% | -1.4 | -11.5 | 821% |
| Folr1 | 1.4 | 11.6 | 829% | -1.7 | -10.9 | 641% |
| RGD1565889 | 1.4 | 12.2 | 871% | -1.7 | -17.5 | 1029% |
| RGD1561931 | 0.9 | 13.8 | 1533% | -1.8 | -10 | 556% |
| Gyk | 2.3 | 14.1 | 613% | -2.2 | -4.4 | 200% |
| Cyp4f4 | 1.8 | 22.8 | 1267% | -2 | -6.4 | 320% |
| Rn149241 | 2.5 | 26.1 | 1044% | -1.9 | -11.3 | 595% |

FIG. 13

METHODS FOR TREATMENT OF TYPE 2 DIABETES

CROSS-REFERENCE TO RELATED APPLICATIONS

This application is a divisional of U.S. application Ser. No. 12/319,883, filed on Jan. 12, 2009 now abandoned, which is a continuation-in-part of U.S. application Ser. No. 11/901,925, filed on Sep. 18, 2007 now abandoned, which is a continuation-in-part of International Application No. PCT/US2007/007875, filed on Mar. 28, 2007, which claims benefit of U.S. Provisional Application Ser. No. 60/841,717, filed on Sep. 1, 2006.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

SEQUENCE LISTING

The instant application contains a Sequence Listing which has been submitted via EFS-Web and is hereby incorporated by reference in its entirety. Said ASCII copy, created on Nov. 6, 2009, is named 05317806.txt, and is 12,345 bytes in size.

FIELD OF THE INVENTION

The present invention relates generally to the identification of biological markers associated with an increased risk of developing Diabetes, as well as methods of using such biological markers in diagnosis and prognosis of Diabetes. Furthermore, selected biological markers of the present invention present new targets for therapy and constitute new therapeutics for treatment or prevention of Diabetes.

BACKGROUND OF THE INVENTION

Diabetes mellitus comprises a cluster of diseases distinguished by chronic hyperglycemia that result from the body's failure to produce and/or use insulin, a hormone produced by β-cells in the pancreas that plays a vital role in metabolism. Symptoms include increased thirst and urination, hunger, weight loss, chronic infections, slow wound healing, fatigue, and blurred vision. Often, however, symptoms are not severe, not recognized, or are absent. Diabetes can lead to debilitating and life-threatening complications including retinopathy leading to blindness, memory loss, nephropathy that may lead to renal failure, cardiovascular disease, neuropathy, autonomic dysfunction, and limb amputation. Several pathogenic processes are involved in the development of Diabetes, including but not limited to, processes which destroy the insulin-secreting β-cells with consequent insulin deficiency, and changes in liver and smooth muscle cells that result in resistance to insulin uptake. Diabetes can also comprise abnormalities of carbohydrate, fat, and protein metabolism attributed to the deficient action of insulin on target tissues resulting from insulin insensitivity or lack of insulin.

Type 2 Diabetes is the most common form of Diabetes, which typically develops as a result of a relative, rather than absolute, insulin deficiency, in combination with the body's failure to use insulin properly (also known in the art as "insulin resistance"). Type 2 Diabetes often manifests in persons, including children, who are overweight; other risk factors include high cholesterol, high blood pressure, ethnicity, and genetic factors, such as a family history of Diabetes. The majority of patients with Type 2 Diabetes are obese, and obesity itself may cause or aggravate insulin resistance. Apart from adults, an increasing number of children are also being diagnosed with Type 2 Diabetes. Due to the progressive nature of the disease, Diabetes complications often develop by the time these children become adults. A study by the American Diabetes Association (ADA) involved 51 children that were diagnosed with Diabetes before the age of 17. By the time these children reached their early 30s, three had kidney failure, one was blind, and two died of heart attacks while on dialysis. This study reinforces the severity of the disease, the serious damage inflicted by Diabetes complications, and the need for early diagnosis of the disease.

The incidence of Diabetes has been rapidly escalating to alarming numbers. Diabetes currently affects approximately 170 million people worldwide with the World Health Organization (WHO) predicting 300 million diabetics by 2025. The United States alone has 20.8 million people suffering from Diabetes (approximately 6% of population and the $6^{th}$ most common cause of death). The annual direct healthcare costs of Diabetes worldwide for people in the 20-79 age bracket are estimated at $153-286 billion and is expected to rise to $213-396 billion in 2025.

Along with the expansion of the diagnosed diabetic population, the undiagnosed diabetic population has also continued to increase, primarily because Type 2 Diabetes is often asymptomatic in its early stages, or the hyperglycemia is often not severe enough to provoke noticeable symptoms of Diabetes. It is believed that approximately 33% of the 20.8 million diabetics in the United States remain undiagnosed. Due to the delay in diagnosis, Diabetes complications have already advanced and thus, the future risk of further complication and derailment is severely increased. To obviate complications and irreversible damage to multiple organs, Diabetes management guidelines advocate initiation of therapeutic intervention early in the prognosis of the disease.

This modern epidemic requires new tools for early detection of Type 2 Diabetes, before the disease instigates significant and irreparable damage. In addition, new treatment paradigms are needed to halt, delay, or ameliorate the massive deterioration in patient health, ideally reversing the course of the disease to partial or complete cure as an alternative or a substitute for current treatments, which merely address chronic management of disease symptoms. Diabetic hyperglycemia can be decreased by weight reduction, increased physical activity, and/or therapeutic treatment modalities. Several biological mechanisms are associated with hyperglycemia, such as insulin resistance, insulin secretion, and gluconeogenesis, and there are several agents available that act on one or more of these mechanisms, such as but not limited to metformin, acarbose, and rosiglitazone.

It is well documented that the pre-diabetic state can be present for ten or more years before the detection of glycemic disorders like Diabetes. Treatment of pre-diabetics with therapeutic agents can postpone or prevent Diabetes; yet few pre-diabetics are identified and treated. Thus, there remains a need in the art for methods of identifying and diagnosing these individuals who are not yet diabetics, but who are at significant risk of developing Diabetes.

SUMMARY OF THE INVENTION

The present invention is premised on the discovery that disease-associated biomarkers can be identified in serum or other bodily fluids long before overt disease is apparent. The presence or absence of these biomarkers from the serum footprints of patients suffering from Type 2 Diabetes precede disruptions in blood glucose control and can be used as early diagnostic tools, for which treatment strategies can be devised and administered to prevent, delay, ameliorate, or reverse irreversible organ damage. One or several of the disease-associated biomarkers of the present invention can be used to diagnose subjects suffering from Type 2 Diabetes or related diseases, or advantageously, to diagnose those subjects who are asymptomatic for Type 2 Diabetes and related diseases. The biomarkers of the present invention can also be used for the design of new therapeutics. For instance, a biomarker absent in a diabetic patient and found in a healthy individual can constitute a new protective or therapeutic agent which, upon administration to the patient, may alleviate symptoms or even reverse the disease.

The present inventors have found a peptide fragment from the Cohen diabetic (CD) rat model that is homologous to human SERPINA1 and SERPINA3. In the CD rat model, the sensitive strain (CDs) develops Diabetes within 30 days when maintained on a high sucrose/copper-poor diet (HSD), whereas the resistant strain (CDr) retains normal blood glucose levels. When maintained indefinitely on regular rodent diet (RD), neither strain develop symptoms of T2D. The peptide fragment was found in the serum of CDr-RD and CDr-HSD, but not in the serum of CDs-RD or CDs-HSD (Example 1), suggesting that the peptide is only found in rats that have not progressed to a diabetic phenotype. The present inventors have further studied the human homolog of this peptide and found that the human homolog exhibits strong kinase inhibitory activity.

Accordingly, in one aspect of the present invention, an isolated peptide comprising an amino acid sequence selected from the group consisting of SEQ ID NO: 1, SEQ ID NO: 2, and SEQ ID NO: 3 is provided. The present invention also concerns an isolated nucleic acid sequence encoding an amino acid sequence selected from the group consisting of SEQ ID NO: 1, SEQ ID NO: 2, and SEQ ID NO: 3.

Another aspect of the invention provides a pharmaceutical composition for inhibiting one or more kinases, comprising as an active ingredient the isolated peptide of the invention, and a pharmaceutically acceptable carrier or diluent.

The present invention also concerns a protein kinase inhibitor, comprising as an active ingredient the isolated peptide of the invention and optionally, a pharmaceutically acceptable carrier or diluent.

In another aspect, the present invention provides a method of inhibiting one or more kinases in a cell, comprising contacting the cell with the isolated peptide of invention. The invention further concerns a method of inhibiting one or more kinases in a subject, comprising administering to the subject the pharmaceutical composition of the invention and measuring the inhibition of one or more kinases.

In another aspect, the present invention provides a method of treating type 2 Diabetes or a pre-diabetic condition in a subject, comprising administering to the subject the pharmaceutical composition of the invention.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, materials, methods, and examples described herein are illustrative only and are not intended to be limiting.

Other features and advantages of the invention will be apparent from and are encompassed by the following detailed description and claims.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 3A depicts a BLAST alignment of the 38-amino acid Serpina 3M (also referred to as "D3") peptide (SEQ ID NO: 1) and proteins identified as having similar sequence identity (SEQ ID NOS 8-17, respectively, in order of appearance).

FIG. 3B shows a BLAST alignment of nucleic acid sequences (SEQ ID NOS 18-26, respectively, in order of appearance) encoding the 38-amino acid Serpina 3M peptide and proteins identified in 3A. Peptide sequence disclosed as SEQ ID NO: 8.

FIG. 4A is a summary of bioinformatic analysis of the D3 peptide. Peptide sequences in the table disclosed as SEQ ID NOS 27-28 & 1.

FIG. 13 is a chart showing the expression of selected transcripts from pancreatic and epididymal fat tissue over time

DETAILED DESCRIPTION OF THE INVENTION

Figure 1:
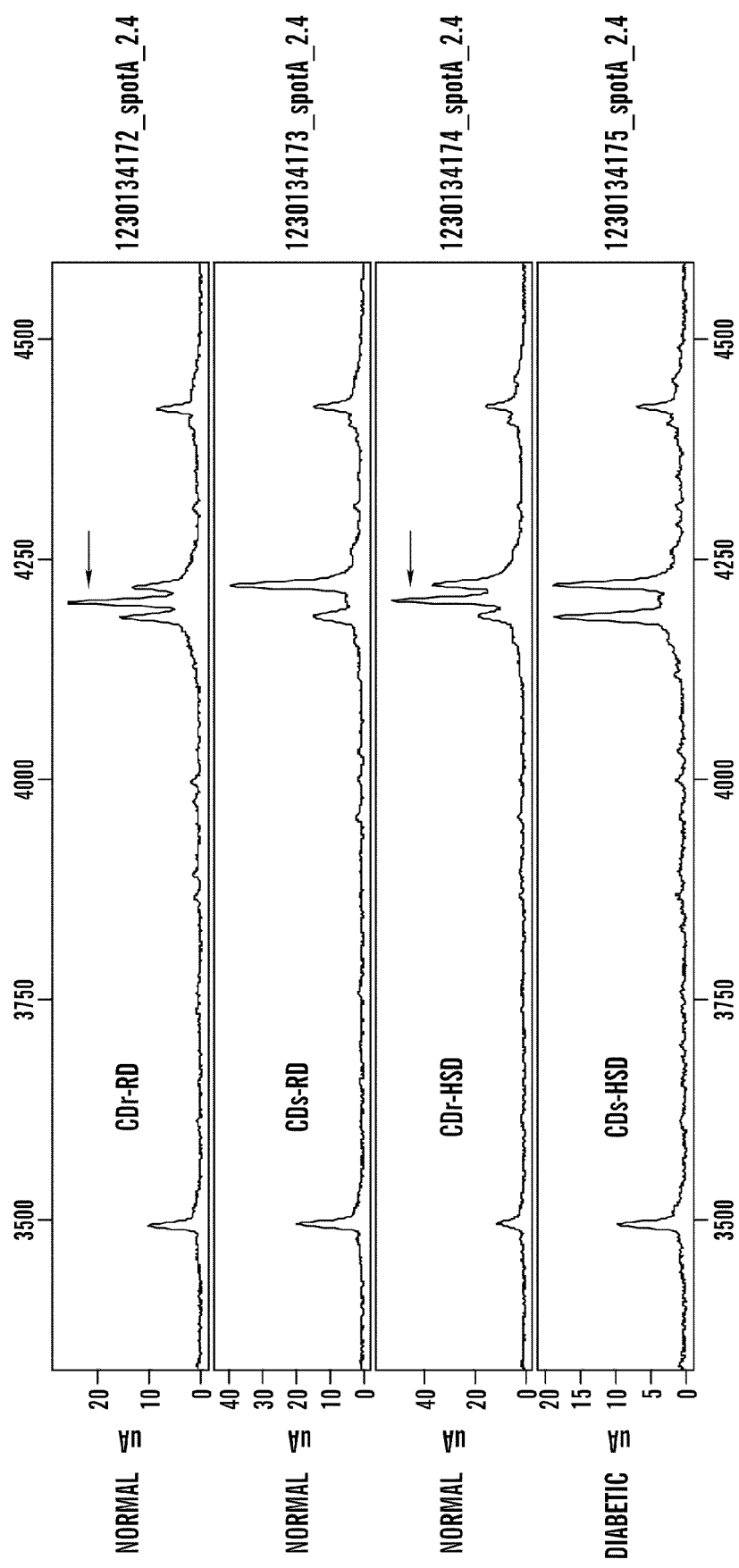
FIG. 1 is a graphical comparison of serum samples from CDr-RD, CDs-RD, CDr-HSD, and CDs-HSD on a SELDI Q10 anion exchange surface chip. A median peak is present in CDr-RD and CDr-HSD (marked by an arrow), but not in CDs-RD and CDs-HSD. A protein fragment from this differentially expressed peak was identified as the C-terminal fragment of Serpina 3M.

The present invention relates to, inter alia, the identification of biomarkers associated with subjects having Diabetes or a pre-diabetic condition, or who are pre-disposed to developing Diabetes or a pre-diabetic condition. Accordingly, the biomarkers and methods of the present invention allow one of skill in the art to identify, diagnose, or otherwise assess those subjects who do not exhibit any symptoms of Diabetes or a pre-diabetic condition, but who nonetheless may be at risk for developing Diabetes or experiencing symptoms characteristic of a pre-diabetic condition. The biomarkers can also be used advantageously to identify subjects having or at risk for developing complications relating to Type 2 Diabetes. These biomarkers are also useful for monitoring subjects undergoing treatments and therapies for Diabetes or pre-diabetic conditions, and for selecting therapies and treatments that would be effective in subjects having Diabetes or a pre-diabetic condition, wherein selection and use of such treatments and therapies slow the progression of Diabetes or pre-diabetic conditions, or substantially delay or prevent its onset. The biomarkers of the present invention can be in the form of a pharmaceutical composition used to treat subjects having type 2 Diabetes or related conditions.

The present inventors have used the Cohen diabetic (CD) rat as a model comprised of 2 strains that manifest many of the common features of type 2 diabetes (T2D) in humans. The sensitive strain (CDs) develops diabetes within 30 days of high sucrose/copper poor diet (HSD), whereas the resistant strain (CDr) retains normal blood glucose levels. Neither strain shows any signs of diabetes when provided regular diet (RD). Thus, incidence of T2D in the CD rat model results from synergistic effects of genetic susceptibility and dietary influence.

Microarray transcriptome profiling revealed a number of biomarkers related to resistance, predisposition or progression of the disease. Particularly, upregulation of Gyk, Scd2 and Nr1h3 and downregulation of Lypla3, Acaa2 and Anxa1 were associated with the resistance to Diabetes. Additionally, forty-eight transcripts showing statistically significant opposite expression trends in resistance or progression of the disease. A decrease in the levels of transcripts involved in angiogenesis and endothelial regulation, such as those encoding, for example, Angiomotin, Folate Receptor 1 and Occludin, was associated with progression of type 2 Diabetes. Similarly, a decrease of expression of Cyp4f4 that mediates leukotriene B(4) metabolism was seen in Diabetes. On the contrary, increased levels of the same markers were associated with resistance to disease. Another interesting finding is a Diabetes associated increase of adipocytic expression of Sox17, a pancreatic progenitor marker. Changes in level of transcripts were observed as early as 10 days after exposure to HSD and became more pronounced after 30 days of the diet. The present invention thus seeks to define predisposition to the development of the type 2 Diabetes as well as be explored as potential drug targets.

In particular, the present inventors have determined that one biomarker in particular, a peptide fragment from the Cohen diabetic (CD) rat model, is homologous to human SERPINA1 and SERPINA3. In the CD rat model, the sensitive strain (CDs) develops Diabetes within 30 days when maintained on a high sucrose/copper-poor diet (HSD), whereas the resistant strain (CDr) retains normal blood glucose levels. When maintained indefinitely on regular rodent diet (RD), neither strain develop symptoms of T2D. The peptide fragment was found in the serum of CDr-RD and CDr-HSD, but not in the serum of CDs-RD or CDs-HSD (Example 1), suggesting that the peptide is only found in rats that have not progressed to a diabetic phenotype. The present inventors have further studied this peptide and found that the peptide exhibits strong kinase inhibitory activity. Thus, the present invention also concerns biomarkers that can act as peptide inhibitors of kinases involved in type 2 Diabetes or pre-diabetic conditions that can be used, for example, in pharmaceutical compositions to treat type 2 Diabetes, pre-diabetic conditions, or related conditions, such as complications related to type 2 Diabetes.

As used herein, "a," "an" and "the" include singular and plural referents unless the context clearly dictates otherwise. Thus, for example, reference to "an active agent" or "a pharmacologically active agent" includes a single active agent as well as two or more different active agents in combination, reference to "a carrier" includes mixtures of two or more carriers as well as a single carrier, and the like.

The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments, regions, conjugates, or derivatives thereof, provided by any known technique, such as, but not limited to, enzymatic cleavage, peptide synthesis or recombinant techniques.

As used herein, the term "antigen binding region" refers to that portion of an antibody molecule which contains the amino acid residues that bind and interact with an antigen and confer on the antibody its specificity and affinity for the antigen. The antibody region includes the "framework" amino acid residues necessary to maintain the proper conformation of the antigen-binding residues.

An "antigen" is a molecule or a portion of a molecule capable of being bound by an antibody which is additionally capable of inducing an animal to produce antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens. Preferred antigens that bind antibodies, fragments and regions of antibodies of the present invention include at least one, preferably two, three, four, five, six, seven, eight, nine, ten or more amino acid residues of SEQ ID NO:1, SEQ ID NO: 2, or SEQ ID NO: 3, but can also bind to any one or more biomarkers of the invention, or metabolites thereof, such as those set forth in Table 1 herein.

The term "biomarker" in the context of the present invention encompasses, without limitation, proteins, peptides (including the peptide inhibitors disclosed herein), nucleic acids, polymorphisms of proteins and nucleic acids, splice variants, fragments of proteins or nucleic acids, elements, metabolites, and other analytes. Biomarkers can also include mutated proteins or mutated nucleic acids. The biomarkers disclosed herein are used interchangeably with the term "T2DBMARKER".

"Complications related to type 2 Diabetes" or "complications related to a pre-diabetic condition" can include, without limitation, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof.

"Diabetes Mellitus" in the context of the present invention encompasses Type 1 Diabetes, both autoimmune and idiopathic and Type 2 Diabetes (together, "Diabetes"). The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level$\geq$11.1 mmol/L ($\geq$200 mg/dL). Other values suggestive of or indicating high risk for Diabetes Mellitus include elevated arterial pressure$\geq$140/90 mm Hg; elevated plasma triglycerides ($\geq$1.7 mmol/L; 150 mg/dL) and/or low HDL-cholesterol (<0.9 mmol/L, 35 mg/dl for men; <1.0 mmol/L, 39 mg/dL women); central obesity (males: waist to hip ratio>0.90; females: waist to hip ratio>0.85) and/or body mass index exceeding 30 kg/m$^2$; microalbuminuria, where the urinary albumin excretion rate$\geq$20 µg/min or albumin:creatinine ratio$\geq$30 mg/g).

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. An epitope can comprise the antibody binding region of any one or more of T2DBMARKERS disclosed herein, or a metabolite thereof. An epitope can also comprise at least one, preferably two, three, four, five, six, seven, eight, nine, ten or more amino acid residues of SEQ ID NO: 1, SEQ ID NO: 2, or SEQ ID NO: 3. The amino acid residues of the epitope that are recognized by the isolated antibodies of the invention need not be contiguous.

"Impaired glucose tolerance" (IGT) is defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75 g oral glucose tolerance test. These glucose levels are above normal but below the level that is diagnostic for Diabetes. Subjects with impaired glucose tolerance or impaired fasting glucose have a significant risk of developing Diabetes and thus are an important target group for primary prevention.

"Insulin resistance" refers to a condition in which the cells of the body become resistant to the effects of insulin, that is, the normal response to a given amount of insulin is reduced. As a result, higher levels of insulin are needed in order for insulin to exert its effects.

"Normal glucose levels" is used interchangeably with the term "normoglycemic" and refers to a fasting venous plasma glucose concentration of less than 6.1 mmol/L (110 mg/dL). Although this amount is arbitrary, such values have been observed in subjects with proven normal glucose tolerance, although some may have IGT as measured by oral glucose tolerance test (OGTT). A baseline value, index value, or reference value in the context of the present invention and defined herein can comprise, for example, "normal glucose levels."

A "pre-diabetic condition" refers to a metabolic state that is intermediate between normal glucose homeostasis, metabolism, and states seen in frank Diabetes Mellitus. Pre-diabetic conditions include, without limitation, Metabolic Syndrome ("Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. The World Health Organization defines values for IFG as a fasting plasma glucose concentration of 6.1 mmol/L (100 mg/dL) or greater (whole blood 5.6 mmol/L; 100 mg/dL), but less than 7.0 mmol/L (126 mg/dL)(whole blood 6.1 mmol/L; 110 mg/dL). Metabolic Syndrome according to National Cholesterol Education Program (NCEP) criteria are defined as having at least three of the following: blood pressure$\geq$130/85 mm Hg; fasting plasma glucose$\geq$6.1 mmol/L; waist circumference>102 cm (men) or >88 cm (women); triglycerides$\geq$1.7 mmol/L; and HDL cholesterol<1.0 mmol/L (men) or 1.3 mmol/L (women).

A "sample" in the context of the present invention is a biological sample isolated from a subject and can include, for example, serum, blood plasma, blood cells, endothelial cells, tissue biopsies, lymphatic fluid, pancreatic juice, ascites fluid, interstitital fluid (also known as "extracellular fluid" and encompasses the fluid found in spaces between cells, including, inter alia, gingival crevicular fluid), bone marrow, sputum, saliva, tears, or urine.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of type 2 Diabetes Mellitus or pre-diabetic conditions. A subject can be male or female. A subject can be one who has been previously diagnosed with or identified as suffering from or having type 2 Diabetes, one or more complications related to type 2 Diabetes, or a pre-diabetic condition, and optionally, but need not have already undergone treatment for the type 2 Diabetes, the one or more complications related to type 2 Diabetes, or the pre-diabetic condition. A subject can also be one who is not suffering from type 2 Diabetes or a pre-diabetic condition. A subject can also be one who has been diagnosed with or identified as suffering from type 2 Diabetes, one or more complications related to type 2 Diabetes, or a pre-diabetic condition, but who show improvements in known Diabetes risk factors as a result of receiving one or more treatments for type 2 Diabetes, one or more complications related to type 2 Diabetes, or the pre-diabetic condition. Alternatively, a subject can also be one who has not been previously diagnosed as having Diabetes, one or more complications related to type 2 Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to type 2 Diabetes or a pre-diabetic condition as defined herein, or alternatively, a subject can be one who has not been previously diagnosed with or identified as having one or more complications related to type 2 Diabetes or a pre-diabetic condition.

Biomarkers of the Invention

Proteins, peptides, nucleic acids, polymorphisms, and metabolites whose levels are changed in subjects who have Diabetes or a pre-diabetic condition, or are predisposed to developing Diabetes or a pre-diabetic condition are summarized in Table 1 and are collectively referred to herein as, inter alia, "Diabetes-associated proteins", "T2DBMARKER polypeptides", or "T2DBMARKER proteins". The corresponding nucleic acids encoding the polypeptides are referred to as "Diabetes-associated nucleic acids", "Diabetes-associated genes", "T2DBMARKER nucleic acids", or "T2DBMARKER genes". Unless indicated otherwise, "T2DBMARKER", "Diabetes-associated proteins", "Diabetes-associated nucleic acids" are meant to refer to any of the sequences disclosed herein. The corresponding metabolites of the T2DBMARKER proteins or nucleic acids can also be measured, herein referred to as "T2DBMARKER metabolites". Calculated indices created from mathematically combining measurements of one or more, preferably two or more of the aforementioned classes of T2DBMARKERS are referred to as "T2DBMARKER indices". Proteins, nucleic acids, polymorphisms, mutated proteins and mutated nucleic acids, metabolites, and other analytes are, as well as common physiological measurements and indices constructed from any of the preceding entities, are included in the broad category of "T2DBMARKERS".

Five hundred and forty-eight (548) biomarkers have been identified as having altered or modified presence or concentration levels in subjects who have Diabetes, or who exhibit symptoms characteristic of a pre-diabetic condition, such as those subjects who are insulin resistant, have altered beta cell function or are at risk of developing Diabetes based upon known clinical parameters or risk factors, such as family history of Diabetes, low activity level, poor diet, excess body weight (especially around the waist), age greater than 45 years, high blood pressure, high levels of triglycerides, HDL cholesterol of less than 35, previously identified impaired glucose tolerance, previous Diabetes during pregnancy ("gestational Diabetes Mellitus") or giving birth to a baby weighing more than nine pounds, and ethnicity.

Table 1 comprises the five hundred and forty-eight (548) T2DBMARKERS of the present invention. One skilled in the art will recognize that the T2DBMARKERS presented herein encompasses all forms and variants, including but not limited to, polymorphisms, isoforms, mutants, derivatives, precursors including nucleic acids, receptors (including soluble and transmembrane receptors), ligands, and post-translationally modified variants, as well as any multi-unit nucleic acid, protein, and glycoprotein structures comprised of any of the T2DBMARKERS as constituent subunits of the fully assembled structure.

TABLE 1

| | T2DBMARKERS | |
|---|---|---|
| T2DBMARKER | Common Name | Alternative Name |
| 1 | Serpina 3M | C-terminal fragment of a predicted protein, similar to serine protease inhibitor 2.4 |
| 2 | Spin 2a | |
| 3 | Fetuin beta | Fetub; Fetuin β; Fetuin B |
| 4 | Apolipoprotein C-III precursor | Apoc3 |
| 5 | Predicted protein, similar to Apolipoprotein C2 | Apoc2, predicted |
| 6 | Alpha-2-HS-glycoprotein | α-2-HS-glycoprotein; Ahsg; Fetuin α; Fetuin A; Aa2-066 |
| 7 | T-kininogen II precursor | |
| 8 | Alpha-1-macroglobulin | α-1-macroglobulin; A2MG; Pzp; pregnancy-zone protein |
| 9 | Serpin C1 | Serine/cysteine proteinase inhibitor, clade C, member 1 (predicted) |
| 10 | Coagulation factor 2 | F2 |
| 11 | Inter-alpha-inhibitor H4 heavy chain | ITIH4 |
| 12 | Vitamin D binding protein prepeptide | Gc; VTDB |
| 13 | Low-molecular weight T-kininogen I precursor | Kininogen; LMW T-kininogen I precursor; major acute phase alpha-1 protein precursor |
| 14 | Apolipoprotein A-1 | Preapolipoprotein A-1; ApoA1 |
| 15 | Predicted protein, similar to apolipoprotein C-II precursor | Apoc2, precursor |

TABLE 1-continued

T2DBMARKERS

| T2DBMARKER | Common Name | Alternative Name |
|---|---|---|
| 16 | Thrombin | Prothrombin precursor; THRB |
| 17 | Apolipoprotein E | ApoE |
| 18 | Liver regeneration-related protein LRRG03 | Tf |
| 19 | Apolipoprotein A-IV | ApoA4 |
| 20 | Alpha-1-inhibitor 3 precursor | LOC297568 |
| 21 | XP_579384 | |
| 22 | Histidine-rich glycoprotein | Hrg |
| 23 | XP_579477 | |
| 24 | Complement component C9 precursor | C9 |
| 25 | Apolipoprotein H | ApoH |
| 26 | B-factor, properdin | Cfb |
| 27 | Hemopexin | Hpx |
| 28 | Calnexin | Ca(2+)-binding phosphoprotein p90 |
| 29 | Reg3a | Rn.11222; regenerating islet-derived 3 alpha |
| 30 | LOC680945 | Rn.1414; similar to stromal cell-derived factor 2-like 1 |
| 31 | Pap | Rn.9727; pancreatitis-associated protein |
| 32 | Ptf1a | Rn.10536; Pancreas specific transcription factor, 1a |
| 33 | Mat1a | Rn.10418; methionine adenosyltransferase I, alpha |
| 34 | Nupr1 | Rn.11182; nuclear protein 1 |
| 35 | Rn.128013 | |
| 36 | Chac1 (predicted) | Rn.23367; ChaC; cation transport regulator-like 1 |
| 37 | Slc7a3 | Rn.9804; solute carrier family 7 (cationic amino acid transporter, y+ system), member 3 |
| 38 | LOC312273 | Rn.13006; trypsin V-A |
| 39 | Rn.47821 | |
| 40 | Ptger3 | Rn.10361; prostaglandin E receptor 3 (subtype EP3 |
| 41 | RGD1562451 | Rn.199400; similar to Pabpc4 predicted protein |
| 42 | RGD1566242 | Rn.24858; similar to RIKEN cDNA 1500009M05 |
| 43 | Cyp2d26 | Rn.91355; Cytochrome P450, family 2, subfamily d, polypeptide 26 |
| 44 | Rn.17900 | Similar to aldehyde dehydrogenase 1 family, member L2 |
| 45 | LOC286960 | Rn.10387; preprotrypsinogen IV |
| 46 | Gls2 | Rn.10202; glutaminase 2 (liver, mitochondrial) |
| 47 | Nme2 | Rn.927; expressed in non-metastatic cells 2 |
| 48 | Rn.165714 | |
| 49 | P2rx1 | Rn.91176; purinergic receptor PX2, ligand-gated ion channel, 1 |
| 50 | Pdk4 | Rn.30070; pyruvate dehydrogenase kinase, isoenzyme 4 |
| 51 | Amy1 | Rn.116361; amylase 1, salivary |
| 52 | Cbs | Rn.87853; cystathionine beta synthase |
| 53 | Mte1 | Rn.37524; mitochondrial acyl-CoA thioesterase 1 |
| 54 | Spink1 | Rn.9767; serine protease inhibitor, Kazal type 1 |
| 55 | Gatm | Rn.17661; glycine amidinetransferase (L-arginine:glycine amidinotransferase) |
| 56 | Tmed6_predicted | Rn.19837; transmembrane emp24 protein transport domain containing 6 |
| 57 | Tff2 | Rn.34367; trefoil factor 2 (spasmolytic protein 1) |
| 58 | Hsd17b13 | Rn.25104; hydroxysteroid (17-beta) dehydrogenase 13 |
| 59 | Rn.11766 | Similar to LRRGT00012 |
| 60 | Gnmt | Rn.11142; glycine N-methyltransferase |
| 61 | Pah | Rn.1652; phenylalanine hydroxylase |
| 62 | Serpini2 | Rn.54500; serine/cysteine proteinase inhibitor, clade I, member 2 |
| 63 | RGD1309615 | Rn.167687 |
| 64 | LOC691307 | Rn.79735; similar to leucine rich repeat containing 39 isoform 2 |
| 65 | Eprs | Rn.21240; glutamyl-prolyl-tRNA synthetase |
| 66 | Pck2_predicted | Rn.35508; phosphoenolpyruvate carboxykinase 2 (mitochondrial) |
| 67 | Chd2_predicted | Rn.162437; chromodomain helicase DNA binding protein 2 |
| 68 | Rn.53085 | |
| 69 | Rn.12530 | |
| 70 | NIPK | Rn.22325; tribbles homolog; cDNA clone RPCAG66 3' end, mRNA sequence |
| 71 | Slc30a2 | Rn.11135; solute carrier family 30 (zinc transporter), member 2 |
| 72 | Serpina10 | Rn.10502; serine/cysteine peptidase inhibitor, clade A, member 10 |

TABLE 1-continued

T2DBMARKERS

| T2DBMARKER | Common Name | Alternative Name |
|---|---|---|
| 73 | Cfi | Rn.7424; complement factor I |
| 74 | Cckar | Rn.10184; cholecystokinin A receptor |
| 75 | LOC689755 | Rn.151728; LOC689755 |
| 76 | Bhlhb8 | Rn.9897; basic helix-loop-helix domain containing class B, 8 |
| 77 | Anpep | Rn.11132; alanyl (membrane) aminopeptidase |
| 78 | Asns | Rn.11172; asparagine synthetase |
| 79 | Slc7a5 | Rn.32261; solute carrier family 7 (cationic amino acid transporter, y+ system), member 5 |
| 80 | Usp43_predicted | Rn.12678; ubiquitin specific protease 43 |
| 81 | Csnk1a1 | Rn.23810; casein kinase 1, alpha 1 |
| 82 | Cml2 | Rn.160578; camello-like 2 |
| 83 | Pabpc4 | Rn.199602 |
| 84 | Gjb2 | Rn.198991; gap junction membrane channel protein beta 2 |
| 85 | Ngfg | Rn.11331; nerve growth factor, gamma |
| 86 | Clca2_predicted | Rn.48629 |
| 87 | RGD1565381 | Rn.16083; similar to RIKEN cDNA 181003M07 |
| 88 | Qscn6 | Rn.44920; quiescin Q6 |
| 89 | Cldn10_predicted | Rn.99994; claudin 10 |
| 90 | Spink3 | Rn.144683; serine protease inhibitor, Kazal type 3 |
| 91 | LOC498174 | Rn.163210; similar to NipSnap2 protein (glioblastoma amplified sequence) |
| 92 | Rn.140163 | Similar to methionine-tRNA synthetase |
| 93 | Cyr61 | Rn.22129; cysteine rich protein 61 |
| 94 | RGD1307736 | Rn.162140; Similar to KIAA0152 |
| 95 | Ddit3 | Rn.11183; DNA damage inducible transcript 3 |
| 96 | Reg1 | Rn.11332; regenerating islet derived 1 |
| 97 | Eif4b | Rn.95954; eukaryotic translation initiation factor 4B |
| 98 | Rnase4 | Rn.1742; ribonuclease, RNase A family 4 |
| 99 | Cebpg | Rn.10332; CCAAT/enhancer binding protein (C/EBP), gamma |
| 100 | siat7D | Rn.195322; alpha-2,6-sialyltransferase ST6GalNAc IV |
| 101 | Herpud1 | Rn.4028; homocysteine-inducible, ubiquitin-like domain member 1 |
| 102 | Unknown rat cDNA | |
| 103 | Gcat | Rn.43940; glycine C-acetyltransferase (2-amino-3-ketobutyrate-coenzyme A ligase) |
| 104 | RGD1562860 | Rn.75246; similar to RIKEN cDNA 2310045A20 |
| 105 | pre-mtHSP70 | Rn.7535; 70 kD heat shock protein precursor; Hspa9a_predicted; heat shock 70 kD protein 9A |
| 106 | Dbt | Rn.198610; dihydrolipoamide branched chain transacylase E2 |
| 107 | Bspry | Rn.53996; B-box and SPRY domain containing |
| 108 | Fut1 | Rn.11382; fucosyltransferase 1 |
| 109 | Rpl3 | Rn.107726; ribosomal protein L3 |
| 110 | Rn.22481 | Similar to NP_083520.1 acylphosphatase 2, muscle type |
| 111 | Vldlr | Rn.9975; very low density lipoprotein receptor |
| 112 | RGD1311937 | Rn.33652; similar to MGC17299 |
| 113 | RGD1563144 | Rn.14702; Similar to EMeg32 protein |
| 114 | Rn.43268 | |
| 115 | Ddah1 | Rn.7398; dimethylarginine dimethylaminohydrolase 1 |
| 116 | RAMP4 | Rn.2119; ribosome associated membrane protein 4 |
| 117 | Rn.169405 | |
| 118 | Ccbe1_predicted | Rn.199045; collagen and calcium binding EGF domains 1 |
| 119 | Dnajc3 | Rn.162234; DnaJ (Hsp40) homolog, subfamily C, member 3 |
| 120 | Mtac2d1 | Rn.43919; membrane targeting (tandem)C2 domain containing 1 |
| 121 | RGD1563461 | Rn.199308 |
| 122 | Gimap4 | Rn.198155; GTPase, IMAP family member 4 |
| 123 | Klf2_predicted | Rn.92653; Kruppel-like factor 2 (lung) |
| 124 | RGD1309561 | Rn.102005; similar to FLH31951 |
| 125 | NAP22 | Rn.163581 |
| 126 | Sfrs3_predicted | Rn.9002; splicing factor, arginine/serine-rich 3 (SRp30) |
| 127 | Rn.6731 | |
| 128 | Cd53 | Rn.31988; CD53 antigen |
| 129 | RGD1561419 | Rn.131539; similar to RIKEN cDNA 6030405P05 gene; ARHGAP30; Hs.389374; Rho GTPase activating protein |
| 130 | Il2rg | Rn.14508; interleukin 2 receptor, gamma |
| 131 | LOC361346 | Rn.31250; similar to chromosome 18 open reading frame 54 |

TABLE 1-continued

T2DBMARKERS

| T2DBMARKER | Common Name | Alternative Name |
|---|---|---|
| 132 | Plac8_predicted | Rn.2649; placenta-specific 8 |
| 133 | LOC498335 | Rn.6917; similar to small inducible cytokine B13 precursor (CXCL13) |
| 134 | Igfbp3 | Rn.26369; insulin-like growth factor binding protein 3 |
| 135 | Ptprc | Rn.90166; Hs.192039; protein tyrosine phosphatase, receptor type C; CD45 |
| 136 | RT1-Aw2 | Rn.40130; RT1 class Ib, locus Aw2 |
| 137 | Rac2 | Rn.2863; RAS-related C3 botulinum substrate 2 |
| 138 | Rn.9461 | |
| 139 | Fos | Rn.103750; FBJ murine osteosarcoma viral oncogene homolog |
| 140 | Sgne1 | Rn.6173; secretory granule neuroendocrine protein 1 |
| 141 | Fcgr2b | Rn.33323; Fc receptor, IgG, low affinity IIb |
| 142 | Slfn8 | Rn.137139; Schlafen 8 |
| 143 | Rab8b | Rn.10995; RAB8B, member RAS oncogene family |
| 144 | Rn.4287 | |
| 145 | RGD1306939 | Rn.95357; similar to mKIAA0386 protein |
| 146 | Tnfrsf26_predicted | Rn.162508; tumor necrosis factor receptor superfamily, member 26 |
| 147 | Ythdf2_predicted | Rn.21737; YTH domain family 2 |
| 148 | RGD1359202 | Rn.10956; similar to immunoglobulin heavy chain 6 (Igh-6); IGHG1 in humans; immunoglobulin heavy constant gamma 1 |
| 149 | RGD1562855 | Rn.117926; similar to Ig kappa chain |
| 150 | Igha_mapped | Rn.109625; immunoglobulin heavy chain (alpha polypeptide) (mapped) |
| 151 | Ccl21b | Rn.39658; chemokine (C-C motif) ligand 21b (serine) |
| 152 | IGHM | Rn.201760; Hs.510635; IGHM; immunoglobulin heavy constant mu |
| 153 | LCK | Rn.22791; Hs.470627; lymphocyte protein tyrosine kinase |
| 154 | ARHGDIB | Rn.15842; Hs. 507877; Rho GDP dissociation inhibitor (GDI) beta |
| 155 | CD38 | Rn.11414; Hs.479214; CD38 antigen |
| 156 | S100B | Rn.8937; Hs.422181; S100 calcium binding protein B, beta polypeptide |
| 157 | RGD1306952 | Rn.64439; Similar to Ab2-225 |
| 158 | Dmrt2 | Rn.11448; Doublesex and mab-3 related transcription factor 2 (predicted) |
| 159 | AA819893 | Rn.148042; unknown cDNA |
| 160 | Gpr176 | Rn.44656; G-protein coupled receptor 176 |
| 161 | Tmem45b | Rn.42073; transmembrane protein 45b |
| 162 | Nfkbil1 | Rn.38632; nuclear factor of kappa light polypeptide gene enhancer in B-cells inhibitor-like 1 |
| 163 | Dctn2 | Rn.101923; Dynactin 2 |
| 164 | Itpkc | Rn.85907; Inositol 1,4,5-trisphosphate 3-kinase C |
| 165 | BM389613 | Rn.171826; unknown cDNA |
| 166 | Prodh2 | Rn.4247; proline dehydrogenase (oxidase) 2 |
| 167 | BF288777 | Rn.28947; unknown cDNA |
| 168 | Abi3 | Rn.95169; ABI gene family, member 3 |
| 169 | AW531966 | Rn.8606; unknown cDNA |
| 170 | RGD1560732 | Rn.100399; Similar to LIM and senescent cell antigen-like domains 1 (predicted) |
| 171 | Oxsr1 | Rn.21097; oxidative-stress responsive 1 (predicted) |
| 172 | MGC114531 | Rn.39247; unknown cDNA |
| 173 | BF418465 | Rn.123735; unknown cDNA |
| 174 | LOC690911 | Rn.25022; similar to Msx2-interacting protein (SPEN homolog) |
| 175 | Pex6 | Rn.10675; Peroxisomal biogenesis factor 6 |
| 176 | RGD1311424 | Rn.57800; similar to hypothetical protein FLJ38348 (predicted) |
| 177 | AI013238 | Rn.135595; unknown cDNA |
| 178 | BI288719 | Rn.45106; unknown cDNA |
| 179 | Evp1 | Rn.19832; envoplakin (predicted) |
| 180 | SERPINE2 | Rn.2271; Hs.38449; serine (or cysteine) proteinase inhibitor clade E member 2 |
| 181 | C20orf160 | Rn.6807; Hs.382157; C20orf160 predicted; cystein type endopeptidase |
| 182 | AI072137 | Rn.33396; Transcribed locus |
| 183 | LOC338328 | Rn.7294; Hs.426410; high density lipoprotein binding protein; RGD1564237_predicted |
| 184 | PTPRR | Rn.6277; Hs.506076; protein tyrosine phosphatase receptor type R |
| 185 | LYPLA3 | Rn.93631; Hs.632199; Lysophospholipase 3 |
| 186 | CYYR1 | Rn.1528; Hs.37445; cysteine-tyrosine-rich 1 membrane associated protein |

TABLE 1-continued

T2DBMARKERS

| T2DBMARKER | Common Name | Alternative Name |
|---|---|---|
| 187 | SOX17 | Rn.7884; Hs.98367; SRY-box gene 17 |
| 188 | LY6H | Rn.40119 |
| 189 | SEMA3G | Rn.32183; HS.59729; Semaphorin 3G |
| 190 | C1QTNF1 | Rn.53880; Hs.201398; C1q and tumor necrosis factor related protein 1 |
| 191 | ADCY4 | Rn.1904; Hs.443428; adenylate cyclase 4 |
| 192 | RBP7 | Rn.13092; Hs.422688; retinol binding protein 7; RGD1562168_predicted |
| 193 | ADRB3 | Rn.10100; Hs.2549; adrenergic receptor beta-3 |
| 194 | NR1H3 | Rn.11209; Hs.438863; nuclear receptor subfamily, group H, member 3 |
| 195 | TMEFF1 | Rn.162809; Hs.657066; transmembrane protein with EGF-like and two follistatin-like domains 1 |
| 196 | TIMP-4 | Rn.155651; Hs.591665; Tissue inhibitor of metalloproteinase 4 |
| 197 | CYP4F8 (human) | Rn.10170; Hs.268554; cytochrome P450, family 4, subfamily F, polypeptide 8 |
| 198 | FOLR1 | Rn.6912; Hs.73769; folate receptor 1 |
| 199 | SCD2 | Rn.83595; Hs.558396; stearoyl-CoA desaturase 2 |
| 200 | KIAA2022 | Rn.62924; Hs.124128; DNA polymerase activity |
| 201 | GK | Rn.44654; Hs.1466; glycerol kinase; Gyk |
| 202 | OCLN | Rn.31429; Hs.592605; occluding |
| 203 | SPINT2 | Rn.3857; Hs.31439; serine peptidase inhibitor, Kunitz type, 2 |
| 204 | RBM24 | Rn.164640; Hs.519904; RNA binding motif protein 24 |
| 205 | SLC25A13 | Rn.14686; Hs.489190; solute carrier family 25, member 13 (citrin) |
| 206 | TPMT | Rn.112598; Hs.444319; thiopurine S-methyltransferase |
| 207 | KRT18 | Rn.103924; Hs.406013; keratin 18; keratin complex 1, acidic, gene 18; Krt1-18 |
| 208 | Unknown | Rn.153497 |
| 209 | C2orf40 | Rn.16593; Hs.43125; chromosome 2 open reading frame 40 |
| 210 | LOC440335 | Rn.137175; Hs.390599; hypothetical gene supported by BC022385; RGD1563547; RGE1563547 (predicted) |
| 211 | BEXL1 | Rn.9287; Hs.184736; brain expressed X-linked-like 1; BI289546; brain expressed X-linked 4 |
| 212 | CYB561 | Rn.14673; Hs.355264; cytochrome b-561 |
| 213 | AMOT | Rn.149241; Hs.528051; angiomotin |
| 214 | SQLE | Rn.33239; Hs.71465; squalene epoxidase |
| 215 | ANKRD6 | Rn.45844; Hs.656539; ankyrin repeat domain 6 |
| 216 | CCDC8 | Rn.171055; Hs.97876; coiled-coil domain containing 8 |
| 217 | KRT8 | Rn.11083; Hs.533782; keratin 8 |
| 218 | WWC1 (*Mus musculus*) | Rn.101912; Hs.484047; WW and C2 domain containing 1; RGD1308329; similar to KIAA0869 protein (predicted) |
| 219 | PFKP | Rn.2278; Hs.26010; phosphofructokinase |
| 220 | PEBP1 | Rn.29745; Hs.433863; phosphatidylethanolamine binding protein 1 |
| 221 | SLC7A1 | Rn.9439; Hs.14846; solute carrier family 7 (cationic amino acid transport, y+ system), member 1 |
| 222 | GSTM1 | Rn.625; Hs.301961; glutathione S-transferase M1; glutathione metabolism, mu 1 |
| 223 | CCL5 | Rn.8019; Hs.514821; chemokine (C-C motif) ligand 5 |
| 224 | STEAP1 | Rn.51773; Hs.61635; six transmembrane epithelial antigen of the prostate 1 |
| 225 | IAH1 | Rn.8209; HS.656852; isoamyl acetate-hydrolyzing esterase 1 homolog (S. cerevisiae) |
| 226 | GNA14 | Rn.35127; Hs.657795; guanine nucleotide binding protein (G protein), alpha 14 |
| 227 | TMEM64 | Rn.164935; Hs.567759; transmembrane protein 64 |
| 228 | CCL11 | Rn.10632; Hs.54460; chemokine (C-C motif) ligand 11 |
| 229 | CNN1 | Rn.31788; Hs.465929; Calponin 1 |
| 230 | GGH | Rn.10260; Hs.78619; gamma-glutamyl hydrolase |
| 231 | TPM3 | Rn.17580; Hs.645521; tropomyosin 3 |
| 232 | PCDH7 | Rn.25383; Hs.570785; protocadherin 7 |
| 233 | FHL2 | Rn.3849; Hs.443687; Four and a half LIM domains 2 |
| 234 | COL11A1 | Rn.260; Hs.523446; Collagen, type XI, alpha 1 |
| 235 | EMB | Rn.16221; Hs.645309; Embigin homolog (mouse) |
| 236 | ISG15 | Rn.198318; Hs.458485; ISG15 ubiquitin-like modifier |
| 237 | CRYAB | Rn.98208; Hs.408767; crystalline, alpha B |
| 238 | ACADSB | Rn.44423; Hs.81934; Acyl-Coenzyme A dehydrogenase |
| 239 | Unknown | Rn.7699; Rn.7699; IMAGE clone BC086433 |
| 240 | ABCA1 | Rn.3724; Hs.429294; ATP-binding cassette, subfamily A (ABC1), member 1 |

TABLE 1-continued

T2DBMARKERS

| T2DBMARKER | Common Name | Alternative Name |
|---|---|---|
| 241 | ACSM3 | Rn.88644; Hs.653192; Acyl-CoA synthetase medium-chain family member 3 |
| 242 | ACTA2 | Rn.195319; Hs.500483; Actin, alpha 2, smooth muscle, aorta |
| 243 | RAMP3 | Rn.48672; Hs.25691; receptor (G-protein coupled; calcitonin) activity modifying protein 3 |
| 244 | DDEF1 | Rn.63466; Hs.655552; development and differentiation enhancing factor 1 |
| 245 | NIPSNAP3A | Rn.8287; Hs.591897; Nipsnap homolog 3A (C. elegans) |
| 246 | Unknown | Rn.9546 |
| 247 | GPR64 | Rn.57243; Hs.146978; G protein-coupled receptor 64 |
| 248 | SGCB | Rn.98258; Hs.428953; sarcoglycan, beta; AI413058; 43 kDa dystrophin-associated glycoprotein (43DAG) |
| 249 | BM389408 | Rn.146540; Transcribed locus |
| 250 | RGD1310037_predicted | Rn.199679; Transcribed locus |
| 251 | CALML3 | Rn.105124; Hs.239600; calmodulin-like 3 |
| 252 | LOC645638 | Rn.41321; Hs.463652; similar to WDNM1-like protein |
| 253 | Upk3b_predicted | Rn.6638; transcribed locus |
| 254 | SCEL | Rn.34468; Hs.534699; sciellin |
| 255 | BNC1 | Rn.26595; Hs.459153; Basonuclin 1; BF411725 |
| 256 | FGL2 | Rn.64635; Hs.520989; fibrinogen-like 2 |
| 257 | UPK1B | Rn.9134; Hs.271580; uroplakin 1B |
| 258 | CTDSPL | Rn.37030; Hs.475963; CTD (carboxy-terminal domain, RNA polymerase II, polypeptide A) small phosphatase-like |
| 259 | PIK3R1 | Rn.163585; Hs.132225; phosphoinositide-3-kinase, regulatory subunit (p85 alpha) |
| 260 | POLA2 | Rn.153998; Hs.201897; polymerase (DNA directed), alpha 2 (70 kD subunit); AI175779 |
| 261 | SPTBN1 | Rn.93208; Hs.659362; spectrin, beta, non-erythrocytic 1 |
| 262 | RTEL1 | Rn.98315; Hs.434878; regulator of telomere elongation helicase 1 |
| 263 | MSLN | Rn.18607; Hs.08488; mesothelin |
| 264 | ARVCF | Rn.220; Hs.655877; armadillo repeat gene deleted in velocardiofacial syndrome; Comt; catechol-O-methyltransferase |
| 265 | ALB | Rn.9174; Hs.418167; albumin |
| 266 | SLC6A4 | Rn.1663; Hs.591192; solute carrier family 6 (neurotransmitter transporter, serotonin), member 4 |
| 267 | Unknown | Rn.26537 |
| 268 | BI302615 | Rn.44072; Transcribed locus |
| 269 | Unknown | Rn.199355 |
| 270 | MRPL4 | Rn.13113 |
| 271 | GPR109A | Rn.79620; Hs.524812; G protein-coupled receptor 109A; BI296811 |
| 272 | THBS1 | Rn.185771; Hs.164226; thrombospondin 1 |
| 273 | ANGPTL4 | Rn.119611; Hs.9613; angiopoietin-like 4 |
| 274 | THBS2 | Rn.165619; Hs.371147; thrombospondin 2 |
| 275 | PCK1 | Rn.104376; Hs.1872; phosphoenolpyruvate carboxykinase 1 |
| 276 | UCP3 | Rn.9902; Hs.101337; uncoupling protein 3 |
| 277 | CYFIP2 | Rn.44008; Hs.519702; cytoplasmic FMR1 interacting protein 2 |
| 278 | LOC646851 | Rn.199989; hypothetical protein |
| 279 | DSP | Rn.54711; Hs.519873; desmoplakin |
| 280 | RNF128 | Rn.7002; Hs.496542; ring finger protein 128 |
| 281 | WDR78 | Rn.22852; Hs.49421; WD repeat domain 78 |
| 282 | SLC16A12 | Rn.166976; Hs.530338; solute carrier family 16, member 12 |
| 283 | GRAMD1B | Rn.18035; Hs.144725; GRAM domain containing 1B |
| 284 | HPN | Rn.11139; Hs.182385; hepsin (transmembrane protease, serine 1) |
| 285 | RRAGD | Rn.66516; Hs.485938; Ras-related GTP binding D |
| 286 | MDF1 | Rn.43395; Hs.520119; MyoD family inhibitor |
| 287 | LTB4DH | Rn.10656; Hs.584864; leukotriene B4 12-hydroxydehydrogenase |
| 288 | CELSR2 | Rn.2912; Hs.57652; cadherin, EGF LAG seven-pass G-type receptor 2 |
| 289 | LRP4 | Rn.21381; Hs.4930; low density lipoprotein receptor-related protein 4 |
| 290 | TPCN2 | Rn.138237; Hs.131851; two pore calcium channel protein 2 |
| 291 | TMOD1 | Rn.1646; Hs.494595; tropomodulin 1 |
| 292 | USP2 | Rn.92548; Hs.524085; ubiquitin specific peptidase 2 |
| 293 | SLC16A6 | Rn.54795; Hs.42645; solute carrier family 16, member 6 |

TABLE 1-continued

T2DBMARKERS

| T2DBMARKER | Common Name | Alternative Name |
|---|---|---|
| 294 | ATP1A1 | Rn.2992; Hs.371889; ATPase, Na+/K+ transporting, alpha 1 polypeptide |
| 295 | CSRP2 | Rn.94754; Hs.530904; cysteine and glycine-rich protein 2 |
| 296 | Unknown | Rn.144632 |
| 297 | SLC19A2 | Rn.19386; Hs.30246; solute carrier family 19 (thiamine transporter), member 2 |
| 298 | HRSP12 | Rn.6987; Hs.18426; heat-responsive protein 12 |
| 299 | Fkbp11 | Rn.100569; RK506 binding protein 11 |
| 300 | Ace | Rn.10149; angiotensin I converting enzyme (peptidyl-dipeptidase A) I |
| 301 | Cyp4f4 (rat) | Rn.10170; cytochrome P450, family 5, subfamily 4, polypeptide 4 |
| 302 | BI274837 | Rn.101798; transcribed locus |
| 303 | Hyou1 | Rn.10542; hypoxia up-regulated 1 |
| 304 | Ml15 | Rn.106040; myeloid/lymphoid or mixed-lineage leukemia 5 (trithorax homolog, Drosophila) |
| 305 | Tcf7 | Rn.106335; transcription factor 7, T-cell specific (predicted) |
| 306 | Arf3 | Rn.106440; ADP-ribosylation factor 3 |
| 307 | Mia1 | Rn.10660; melanoma inhibitory activity 1 |
| 308 | Sat | Rn.107986; spermidine/spermine N1-acetyl transferase (mapped) |
| 309 | Mpg | Rn.11241; N-methylpurine-DNA glycosylase |
| 310 | BE115368 | Rn.118708; transcribed locus |
| 311 | BI281874 | Rn.125724; Kelch-like 23 (Drosophila) (predicted) |
| 312 | Lcp1 | Rn.14256; lymphocyte cytosolic protein 1 |
| 313 | RGD1306682 | Rn.143893; similar to RIKEN cDNA 1810046J19 (predicted) |
| 314 | AI502114 | RN.148916; ATP-binding cassette, sub-family A (ABC1), member 1 |
| 315 | AA899202 | Rn.14907; transcribed locus |
| 316 | BI275261 | Rn.157564; transcribed locus |
| 317 | AW532939 | Rn.158403; transcribed locus |
| 318 | Isg20 | Rn.16103; interferon stimulated exonuclease 20 |
| 319 | AI137294 | Rn.161824; similar to Mkrn1protein |
| 320 | BE107848 | Rn.162933; similar to FYVE, RhoGEF and PH domain containing 6 (predicted) |
| 321 | BM390584 | Rn.163173; cDNA clone IMAGE: 7455180, containing frame-shift errors |
| 322 | Slc25a15 | Rn.163331; solute carrier family 25 (mitochondrial carrier; ornithine transporter) member 15 |
| 323 | AA848795 | Rn.163635; transcribed locus |
| 324 | AI103213 | Rn.164935; transcribed locus |
| 325 | Nans | Rn.17006; N-acetylneuraminic acid synthase (sialic acid synthase) (predicted) |
| 326 | BE108415 | Rn.171133; transcribed locus |
| 327 | Pfn2 | Rn.17153; profilin 2 |
| 328 | Ube2n | Rn.177520; ubiquitin-conjugating enzyme E2N |
| 329 | BM384251 | Rn.177573; transcribed locus |
| 330 | Gga2 | Rn.18248; Golgi associated, gamma adaptin ear containing, ARF binding protein 2 |
| 331 | BE106888 | Rn.19198; cysteine-rich with EGF-like domains 2 |
| 332 | AI070306 | Rn.19710; transcribed locus |
| 333 | Reln | Rn.198116; reelin |
| 334 | Glp2 | Rn.1998318; interferon, alpha-inducible protein (clone IFI-15K) (predicted) |
| 335 | Gpc4 | Rn.19945; glypican 4 |
| 336 | BF567145 | Rn.200155; transcribed locus |
| 337 | Manba | Rn.20578; mannosidase, beta A, lysosomal |
| 338 | BM386110 | Rn.223; proliferating cell nuclear antigen |
| 339 | RGD1562142 | Rn.23219; similar to homeotic protein Hox 2.2 - mouse (predicted) |
| 340 | BG378045 | Rn.23614; transcribed locus |
| 341 | AI146051 | Rn.24020; transcribed locus |
| 342 | AI102873 | Rn.2721; transcribed locus |
| 343 | Rdx | Rn.27421; radixin |
| 344 | Dnase1l3 | Rn.29996; deoxyribonuclease I-like 3 |
| 345 | Hexb | Rn.3021; hexosaminidase B |
| 346 | Pls3 | Rn.32103; plastin 3 (T-isoform) |
| 347 | RGD1566102_predicted | Rn.34703; transcribed locus |
| 348 | AI535113 | Rn.34745; transcribed locus |
| 349 | Pdia4 | Rn.39305; protein disulfide isomerase associated 4 |
| 350 | AW529628 | Rn.43319; transcribed locus |
| 351 | BI292232 | Rn.43415; transcribed locus |
| 352 | Kcne3 | Rn.44843; potassium voltage-gated channel, Isk-related subfamily, member 3 |

TABLE 1-continued

T2DBMARKERS

| T2DBMARKER | Common Name | Alternative Name |
|---|---|---|
| 353 | St14 | Rn.49170; suppression of tumorigenicity 14 (colon carcinoma) |
| 354 | Mt1a | Rn.54397; metallothionein 1a |
| 355 | St6gal1 | Rn.54567; betagalactoside alpha 2,6 sialyltransferase 1 |
| 356 | Alcam | Rn.5789; activated leukocyte cell adhesion molecule |
| 357 | Maob | Rn.6656; monoamine oxidase B |
| 358 | AA891161 | Rn.7257; transcribed locus |
| 359 | Slc17a5 | Rn.74591; solute carrier family 17 (anion/sugar transporter), member 5 |
| 360 | RGD1306766 | Rn.7655; similar to hypothetical protein FLJ23514 |
| 361 | Gja5 | Rn.88300; gap junction membrane channel protein alpha 5 |
| 362 | RGD1566265_predicted | Rn.8881; similar to RIKEN cDNA 2610002M06 (predicted) |
| 363 | AI136703 | Rn.92818; transcribed locus |
| 364 | Mta3_predicted | Rn.94848; metastasis associated 3 (predicted) |
| 365 | Pctp | Rn.9487; phosphatidylcholine transfer protein |
| 366 | Map1b | Rn.98152; microtubule-associated protein 1b |
| 367 | Tspan5 | Rn.98240; tetraspanin 5 |
| 368 | Got2 | Rn.98650; glutamate oxaloacetate transaminase 2, mitochondrial |
| 369 | BI285489 | Rn.98850; similar to myo-inositol 1-phosphate synthase A1 |
| 370 | Zfp423 | Rn.9981; Zinc finger protein 423 |
| 371 | Slc6a6 | Rn.9968; solute carrier family 6 (neurotransmitter transporter, taurine), member 6 |
| 372 | Agtr1a | Rn.9814; angiotensin II receptor, type 1 (AT1A) |
| 373 | Ppp1r1a | Rn.9756; protein phosphatase 1, regulatory (inhibitor) subunit 1A |
| 374 | Plin | Rn.9737; perilipin |
| 375 | Dgat2 | Rn.9523; diacylglycerol O-acyltransferase homolog 2 (mouse) |
| 376 | Pcsk6 | Rn.950; proprotein convertase subtilisin/kexin type 6 |
| 377 | BI281177 | Rn.9403; transcribed locus |
| 378 | AI599621 | Rn.92531; Wilms tumor 1 |
| 379 | Ceacam1 | Rn.91235; CEA-related cell adhesion molecule 1 |
| 380 | Gng11 | Rn.892; guanine nucleotide binding protein (G protein), gamma 11 |
| 381 | Cdh11 | Rn.8900; cadherin 11 |
| 382 | Fmo1 | Rn.867; flavin containing monooxygenase 1 |
| 383 | Cbr3_predicted | Rn.8624; carbonyl reductase 3 (predicted) |
| 384 | BE113281 | Rn.85462; quaking homolog, KH domain RNA binding (mouse) |
| 385 | Cidea_predicted | Rn.8171; cell death-inducing DNA fragmentation factor, alpha subunit-like effector A (predicted) |
| 386 | Cav2 | Rn.81070; caveolin 2 |
| 387 | BI273836 | Rn.79933; transcribed locus |
| 388 | Mmrn2_predicted | Rn.7966; multimerin 2 (predicted) |
| 389 | Agtrl | Rn.7965; angiotensin receptor-like 1 |
| 390 | Gypc | Rn.7693; Glycophorin C (Gerbich blood group) |
| 391 | RGD1305719_predicted | Rn.76732; similar to putative N-acetyltransferase Camello 2 (predicted) |
| 392 | AI171656 | Rn.7615; RGD1564859 (predicted) |
| 393 | Spsb1_predicted | Rn.75037; SplA/ryanodine receptor domain and SOCS box containing 1 (predicted) |
| 394 | Bcar3_predicted | Rn.7383; breast cancer anti-estrogen resistance 3 (predicted) |
| 395 | BE115406 | Rn.7282; similar to expressed sequence AA408877 |
| 396 | Dlc1 | Rn.7255; deleted in liver cancer 1 |
| 397 | AW915115 | Rn.65477; transcribed locus |
| 398 | Cdkn2c | Rn.63865; cyclin-dependent kinase inhibitor 2C (p18, inhibits CDK4) |
| 399 | BF387865 | Rn.63789; Transcribed locus |
| 400 | Tst | Rn.6360; Thiosulfate sulfurtransferase |
| 401 | Mbp | Rn.63285; Myelin basic protein |
| 402 | RGD1311474 | Rn.6288; Similar to transmembrane protein induced by tumor necrosis factor alpha |
| 403 | Pfk1 | Rn.59431; Mesoderm specific transcript |
| 404 | BI297693 | Rn.57310; Similar to protein of unknown function (predicted) |
| 405 | Agpat2_predicted | Rn.55456; 1-acylglycerol-3-phosphate O-acyltransferase 2 (lysophosphatidic acid acyltransferase, beta) (predicted) |
| 406 | Ilvb1_predicted | Rn.54315; Synapse defective 1, Rho GTPase, homolog 1 (C. elegans) (predicted) |

TABLE 1-continued

T2DBMARKERS

| T2DBMARKER | Common Name | Alternative Name |
|---|---|---|
| 407 | Ptpns1 | Rn.53971; Protein tyrosine phosphatase, non-receptor type substrate 1 |
| 408 | Col4a1 | Rn.53801; Procollagen, type IV, alpha 1 |
| 409 | Ccl2 | Rn.4772; Chemokine (C-C motif) ligand 2 |
| 410 | Gprc5b_predicted | Rn.47330; G protein-coupled receptor, family C, group 5, member B (predicted) |
| 411 | AI071994 | Rn.44861; Dickkopf homolog 4 (*Xenopus laevis*) (predicted) |
| 412 | BF414285 | Rn.44465; Chemokine-like receptor 1 |
| 413 | Gpd1 | Rn.44452; Glycerol-3-phosphate dehydrogenase 1 (soluble) |
| 414 | Acacb | Rn.44359; Transcribed locus |
| 415 | AI412164 | Rn.44086; Transcribed locus |
| 416 | BF283694 | Rn.44024; Transcribed locus |
| 417 | Ankrd5_predicted | Rn.44014; Ankyrin repeat domain 5 (predicted) |
| 418 | AI144739 | Rn.43251; Similar to KIAA0303 (predicted) |
| 419 | BG661061 | Rn.41321; WDNM1 homolog |
| 420 | Prkar2b | Rn.4075; Protein kinase, cAMP dependent regulatory, type II beta |
| 421 | BI290794 | Rn.40729; Transcribed locus |
| 422 | BM384701 | Rn.40541; PE responsive protein c64 |
| 423 | RGD1565118_predicted | Rn.39037; Similar to mKIAA0843 protein (predicted) |
| 424 | Cd248_predicted | Rn.38806; CD248 antigen, endosialin (predicted) |
| 425 | Acaa2 | Rn.3786; Acetyl-Coenzyme A acyltransferase 2 (mitochondrial 3-oxoacyl-Coenzyme A thiolase) |
| 426 | BM390128 | Rn.36545; Tenascin XA |
| 427 | RGD1309578 | Rn.35367; Similar to Aa2-174 |
| 428 | Inhbb | Rn.35074; Inhibin beta-B |
| 429 | AA943681 | Rn.3504; Response gene to complement 32 |
| 430 | BI274428 | Rn.34454; Transcribed locus |
| 431 | Gpm6a | Rn.34370; Glycoprotein m6a |
| 432 | Cbr1 | Rn.3425; Carbonyl reductase 1 |
| 433 | Slc1a3 | Rn.34134; Solute carrier family 1 (glial high affinity glutamate transporter), member 3 |
| 434 | AI179450 | Rn.34019; Transcribed locus |
| 435 | RGD1560062_predicted | Rn.32891; Similar to Laminin alpha-4 chain precursor (predicted) |
| 436 | Phyhd1 | Rn.32623; Phytanoyl-CoA dioxygenase domain containing 1 |
| 437 | Rgl1_predicted | Rn.28005; Ral guanine nucleotide dissociation stimulator,-like 1 (predicted) |
| 438 | Grifin | Rn.26894; Galectin-related inter-fiber protein |
| 439 | BG381647 | Rn.26832; Transcribed locus |
| 440 | Ccl7 | Rn.26815; Chemokine (C-C motif) ligand 7 |
| 441 | AI548615 | Rn.26537; Transcribed locus |
| 442 | Per2 | Rn.25935; Period homolog 2 (*Drosophila*) |
| 443 | Dgat1 | Rn.252; Diacylglycerol O-acyltransferase 1 |
| 444 | Gda | Rn.24783; Transcribed locus |
| 445 | Psme1 | Rn.2472; Proteasome (prosome, macropain) 28 subunit, alpha |
| 446 | Tm4sf1_predicted | Rn.24712; Transmembrane 4 superfamily member 1 (predicted) |
| 447 | Slc22a3 | Rn.24231; Solute carrier family 22, member 3 |
| 448 | AI228291 | Rn.2361; Similar to CG3740-PA |
| 449 | Rasip1_predicted | Rn.23451; Ras interacting protein 1 (predicted) |
| 450 | Pparg | Rn.23443; Peroxisome proliferator activated receptor gamma |
| 451 | BG378238 | Rn.23273; Transcribed locus |
| 452 | Abca8a_predicted | Rn.22789; ATP-binding cassette, sub-family A (ABC1), member 8a (predicted) |
| 453 | BF290937 | Rn.22733; Transcribed locus |
| 454 | Sox18 | Rn.22446; SRY-box containing gene 18 |
| 455 | AI230554 | Rn.22441; Carbonic anhydrase VB, mitochondrial |
| 456 | Col4a2_predicted | Rn.2237; Procollagen, type IV, alpha 2 (predicted) |
| 457 | BF547294 | Rn.22135; Protein tyrosine phosphatase, receptor type, M |
| 458 | Id1 | Rn.2113; Inhibitor of DNA binding 1 |
| 459 | Sulf1 | Rn.20664; Transcribed locus |
| 460 | AI411941 | Rn.20633; Fibronectin type III domain containing 1 |
| 461 | AI385260 | Rn.20514; Unknown (protein for MGC: 72614) |
| 462 | RGD1562428_predicted | Rn.199567; Transcribed locus |
| 463 | Aoc3 | Rn.198327; Amine oxidase, copper containing 3 |
| 464 | AI599365 | Rn.19608; Transcribed locus |
| 465 | RGD1305061 | Rn.196026; Similar to RIKEN cDNA 2700055K07 |
| 466 | BF282889 | Rn.19393; Transcribed locus |
| 467 | RGD1311800 | Rn.1935; Similar to genethonin 1 |
| 468 | Daf1 | Rn.18841; decay accelerating factor 1 |

TABLE 1-continued

T2DBMARKERS

| T2DBMARKER | Common Name | Alternative Name |
|---|---|---|
| 469 | AI030806 | Rn.18599; Transcribed locus |
| 470 | BM386662 | Rn.18571; Tumor suppressor candidate 5 |
| 471 | BF283405 | Rn.18479; Transcribed locus |
| 472 | BI277619 | Rn.18388; Transcribed locus |
| 473 | Anxa1 | Rn.1792; Annexin A1 |
| 474 | Phlda3 | Rn.17905; Pleckstrin homology-like domain, family A, member 3 |
| 475 | Zdhhc2 | Rn.17310; Zinc finger, DHHC domain containing 2 |
| 476 | AI101500 | Rn.17209; Transcribed locus |
| 477 | AW525722 | Rn.168623; Transcribed locus Transcribed locus |
| 478 | AI600020 | Rn.168403; Transcribed locus |
| 479 | Hdgfrp2 | Rn.167154; Transcribed locus |
| 480 | Degs1 | Rn.167052; Transcribed locus |
| 481 | BM389225 | Rn.1664; Transcribed locus |
| 482 | AI407050 | Rn.165854; Transcribed locus |
| 483 | BF291140 | Rn.165750; Transcribed locus |
| 484 | AI176379 | Rn.165711; Transcribed locus |
| 485 | BF403558 | Rn.165637; Transcribed locus |
| 486 | AI008140 | Rn.165579; Transcribed locus |
| 487 | AW536030 | Rn.165356; Similar to liver-specific bHLH-Zip transcription factor |
| 488 | Sdpr | Rn.165134; Transcribed locus |
| 489 | AI385201 | Rn.164647; Transcribed locus |
| 490 | Tgfbr2 | Rn.164421; Transcribed locus |
| 491 | AW535515 | Rn.164403; Transcribed locus |
| 492 | Gata6 | Rn.164357; Transcribed locus |
| 493 | RGD1566234_predicted | Rn.164243; Transcribed locus |
| 494 | Acaca | Rn.163753; Acetyl-coenzyme A carboxylase alpha |
| 495 | RGD1311037 | Rn.163715; Transcribed locus |
| 496 | AA926305 | Rn.163580; Transcribed locus |
| 497 | Efemp1 | Rn.163265; Epidermal growth factor-containing fibulin-like extracellular matrix protein 1 |
| 498 | Aps | Rn.163202; Adaptor protein with pleckstrin homology and src homology 2 domains |
| 499 | Vnn1 | Rn.16319; Vanin 1 |
| 500 | Lpin1 | Rn.162853; Lipin 1 |
| 501 | Ppp1r3c | Rn.162528; Protein phosphatase 1, regulatory (inhibitor) subunit 3C |
| 502 | Twist1 | Rn.161904; Twist gene homolog 1 (*Drosophila*) |
| 503 | C6 | Rn.16145; Complement component 6 |
| 504 | Cabc1 | Rn.160865; Chaperone, ABC1 activity of bc1 complex like (S. pombe) |
| 505 | Vegfb | Rn.160277; Transcribed locus |
| 506 | Ehd2 | Rn.16016; EH-domain containing 2 |
| 507 | Dpyd | Rn.158382; Dihydropyrimidine dehydrogenase |
| 508 | Nnmt_predicted | Rn.15755; Nicotinamide N-methyltransferase (predicted) |
| 509 | BI289692 | Rn.15749; Transcribed locus |
| 510 | Chpt1 | Rn.154718; Choline phosphotransferase 1 |
| 511 | BI295900 | Rn.15413; Dihydrolipoamide S-acetyltransferase (E2 component of pyruvate dehydrogenase complex) |
| 512 | AW917217 | Rn.153603; CCAAT/enhancer binding protein (C/EBP), alpha |
| 513 | AA942745 | Rn.149118; Transcribed locus |
| 514 | BI283648 | Rn.148951; Hypothetical protein LOC691485 |
| 515 | BF393275 | Rn.148773; Transcribed locus |
| 516 | AI555775 | Rn.147356; Transcribed locus |
| 517 | Tgif | Rn.144418; Transcribed locus |
| 518 | Cldn15_predicted | Rn.144007; Transcribed locus |
| 519 | AI578098 | Rn.137828; Similar to CD209 antigen |
| 520 | Cyp2e1 | Rn.1372; Cytochrome P450, family 2, subfamily e, polypeptide 1 |
| 521 | Tm4sf2_mapped | Rn.13685; Transmembrane 4 superfamily member 2 (mapped) |
| 522 | Mdh1 | Rn.13492; Malate dehydrogenase 1, NAD (soluble) |
| 523 | Slc2a4 | Rn.1314; Solute carrier family 2 (facilitated glucose transporter), member 4 |
| 524 | Cmkor1 | Rn.12959; Chemokine orphan receptor 1 |
| 525 | AW528864 | Rn.129539; Transcribed locus |
| 526 | Dnd1 | Rn.12947; Similar to KIAA0564 protein (predicted) |
| 527 | AW528112 | Rn.119594; Transcribed locus |
| 528 | BF397229 | Rn.11817; Transcribed locus |
| 529 | Sfxn1 | Rn.115752; Sideroflexin 1 |
| 530 | Hrasls3 | Rn.11377; HRAS like suppressor 3 |
| 531 | Pla2g2a | Rn.11346; Phospholipase A2, group IIA (platelets, synovial fluid) |

TABLE 1-continued

T2DBMARKERS

| T2DBMARKER | Common Name | Alternative Name |
|---|---|---|
| 532 | Ebf1 | Rn.11257; Early B-cell factor 1 |
| 533 | Sdc2 | Rn.11127; Syndecan 2 |
| 534 | Aqp7 | Rn.11111; Aquaporin 7 |
| 535 | Pc | Rn.11094; Pyruvate carboxylase |
| 536 | Bhlhb3 | Rn.10784; Basic helix-loop-helix domain containing, class B3 |
| 537 | AI602542 | Rn.107412; Transcribed locus |
| 538 | Maf | Rn.10726; V-maf musculoaponeurotic fibrosarcoma oncogene homolog (avian) |
| 539 | Cpa3 | Rn.10700; Carboxypeptidase A3 |
| 540 | Mcpt1 | Rn.10698; Mast cell protease 1 |
| 541 | RGD1309821_predicted | Rn.106115; Similar to KIAA1161 protein (predicted) |
| 542 | Acvr1c | Rn.10580; Activin A receptor, type IC |
| 543 | Ppp2r5a_predicted | Rn.104461; Protein phosphatase 2, regulatory subunit B (B56), alpha isoform (predicted) |
| 544 | Pde3b | Rn.10322; Phosphodiesterase 3B |
| 545 | Pxmp2 | Rn.10292; Peroxisomal membrane protein 2 |
| 546 | P2rx5 | Rn.10257; Purinergic receptor P2X, ligand-gated ion channel, 5 |
| 547 | Cma1 | Rn.10182; Chymase 1, mast cell |
| 548 | Pfkfb1 | Rn.10115; 6-phosphofructo-2-kinase/fructose-2,6-biphosphatase 1 |

From among the 548 T2DBMARKERS discovered to date, the present inventors have discovered one particular T2DBMARKER, a peptide fragment from the Cohen diabetic (CD) rat model having a molecular weight of about 4.2 kD, that is homologous to human SERPINA1 and SERPINA3, and which may exhibit activity as an anti-diabetic agent (SEQ ID NO: 1). In the CD rat model, the sensitive strain (CDs) develops Diabetes within 30 days when maintained on a high sucrose/copper-poor diet (HSD), whereas the resistant strain (CDr) retains normal blood glucose levels. When maintained indefinitely on regular rodent diet (RD), neither strain develop symptoms of T2D. The peptide fragment was found in the serum of CDr-RD and CDr-HSD, but not in the serum of CDs-RD or CDs-HSD (Example 1), suggesting that the peptide is only found in rats that have not progressed to a diabetic phenotype. The present inventors have further studied this peptide and found that the peptide exhibits strong kinase inhibitory activity. Other preferred T2DBMARKERS include any of the peptide sequences described herein, such as, for example, SEQ ID NO: 2, and SEQ ID NO: 3, or any sequences derived from human serpin proteins, e.g., SERPINA1 and SERPINA3 and which have been determined to be peptide inhibitors of kinases implicated in Diabetes. These, too, are considered to be "T2DBMARKERS" in the context of the present invention.

Serpins are a superfamily of proteins classified into 16 clades designated "A-P". The systematic name of each serpin is, "SERPINXy," where X is the clade and y is the number within the clade. To date, thirty-six (36) serpins have been identified in humans. While serpins are named for their ability to inhibit serine proteases of the chymotrypsin family, some are capable of cross-class inhibition of proteases from the subtilisin, papain and caspase families. In addition, some serpins lack protease inhibitory activity and serve other roles, such as hormone transporters, molecular chaperones or catalysts for DNA condensation. Serpins are typically composed of 330-500 amino acids, but can have large N-, C-terminal or internal insertion loops. Serpins can also be post-translationally modified by glycosylation, sulfation, phosphorylation and oxidation to alter their function. Despite a low overall primary sequence identity for the family, serpins share a highly conserved three-dimensional fold comprised of a bundle of 9 α-helices, a β-sandwich composed of three β-sheets, and a reactive site loop (RSL) composed of 20 amino acids (Rau, J. C. et al. (2007) J. Thromb. Hemostasis 5 (Suppl. 1): 102-115).

In the normal native state of a serpin, the RSL is exposed, however, this state is not the most stable. An increase in thermodynamic stability is achieved through the incorporation of the RSL into one of the β-sheets, triggered either through strand extension to form the "latent" state, or through proteolytic nicking anywhere near a scissile bond (the cleaved state). This metastability of the native serpin is critical for protease inhibition. A minimalist kinetic scheme is composed of two steps: the formation of the encounter complex (also known as the Michaelis complex) where the sequence of the RSL is recognized by the protease as a substrate; and the formation of a final covalent complex, where the protease is trapped in an inactive state. The rates of formation and dissociation of the reversible Michaelis complex, along with co-localization in tissues, determines the specificity of the serpin-protease interaction. While the obligate RSL-active site contacts contribute significantly to the formation of the Michaelis complexes, exosite interactions may also be involved.

Over 70 serpin structures have been determined, and these data, along with a large amount of biochemical and biophysical information, reveal that inhibitory serpins are 'suicide' or 'single use' inhibitors that use a unique and extensive conformational change to inhibit proteases. This conformational mobility renders serpins heat-labile and vulnerable to mutations that promote misfolding, spontaneous conformational change, formation of inactive serpin polymers and serpin deficiency. In humans, several conformational diseases or 'serpinopathies' linked to serpin polymerization have been identified, including emphysema (SERPINA1 (antitrypsin) deficiency) (Lomas, D. A. et al. (1992) Nature 357: 605-607), thrombosis (SERPINC1 (antithrombin) deficiency) (Bruce, D. et al. (1994) J. Clin. Invest. 94: 2265-2274) and angioedema (SERPING1 (C1 esterase inhibitor) deficiency) (Aulak, K. S. et al., (1988) Biochem. J. 253: 615-618). Accumulation of serpin polymers in the endoplasmic reticulum of serpin-secreting cells can also result in disease, most notably cirrhosis (SERPINA1 polymerization) (Lomas, D. A. et al.

(1992) Nature 357: 605-607) and familial dementia (SERPINI1 (neuroserpin) polymerization) (Davis, R. L. et al., (1999) Nature 401: 376-379). Other serpin-related diseases are caused by null mutations or (rarely) point mutations. In humans, the majority (27 out of the 36 heretofore identified) of serpins are inhibitory. Clade A serpins include inflammatory response molecules such as SERPINA1 (antitrypsin) and SERPINA3 (antichymotrypsin) as well as the non-inhibitory hormone-transport molecules SERPINA6 (corticosteroid-binding globulin) and SERPINA7 (thyroxine-binding globulin). Clade B includes inhibitory molecules that function to prevent inappropriate activity of cytotoxic apoptotic proteases (SERPINB6, also called PI6, and SERPINB9, also called PI9) and inhibit papain-like enzymes (SERPINB3, squamous cell carcinoma antigen-1) as well as the non-inhibitory molecule SERPINB5 (maspin). SERPINB5 does not undergo the characteristic serpin-like conformational change and functions to prevent metastasis in breast cancer and other cancers through an incompletely characterized mechanism.

The present invention is based in part on the discovery that peptides derived from human SERPINA1 and SERPINA3 may serve as inhibitors of kinases believed to be implicated in type 2 Diabetes Mellitus. Thus, the present invention is directed to peptide inhibitors of kinases and useful implications of these peptides in the treatment of type 2 Diabetes Mellitus, pre-diabetic conditions, and other diabetes-related conditions disclosed herein. The peptide inhibitors of the invention include the amino acid sequences disclosed herein, containing one or more of the motifs "FNRPFL" (SEQ ID NO: 6), "FMS/GKVT/VNP" (SEQ ID NO: 7), "R[S/K]XXPP" or "SXXPP" where F=phenylalanine, N=asparagine, R=arginine, P=proline, L=leucine, M=methionine, S=serine, G=glycine, K=lysine, V=valine, and X=any amino acid. The peptides of the invention have been shown to inhibit kinases in vitro and in vivo.

Protein kinases are enzymes that phosphorylate protein substrates and are key players in signal transduction events from outside the cell to the cytoplasm. Protein kinases are involved in many events relating to the life and death of cells, including mitosis, differentiation, and apoptosis. As such, protein kinases have been considered as favorable drug targets. However, inhibition of many kinases could lead to cell death or other manifestations of cell abnormalities, because their activity is so crucial to the well-being of the cell. Although this is a desirable effect for anticancer drugs, it is a major drawback for most other therapeutics. The present invention relates in part to peptide inhibitors of protein kinases implicated in Diabetes, such as, without limitation, members of the mitogen-actived protein kinase (MAPK) family, such as p70S6K, protein kinase B isoforms, such as PKBβ, protein kinase C isoforms, such as PKCζ, and serum and glucocorticoid induced protein kinase (SGK).

The peptide inhibitors of the invention can be used to inhibit the activity of kinases involved in type 2 Diabetes Mellitus, pre-diabetic conditions (such as, for example, metabolic syndrome, impaired glucose tolerance, insulin resistance, or impaired fasting glycemia), or complications relating to type 2 Diabetes Mellitus. The peptide inhibitors are useful for treating type 2 Diabetes Mellitus or a pre-diabetic condition in a subject or preventing type 2 diabetes or pre-diabetic conditions in a subject. The peptide inhibitors are also useful therapeutic or research tools in the areas of immunology, hematologic deficiencies and malignancies, metabolism, or any field of study where serpins have been shown to be important.

Methods of Detecting Biomarkers

Levels of T2DBMARKERS can be determined at the protein or nucleic acid level using any method known in the art. T2DBMARKER amounts can be detected, inter alia, electrophoretically (such as by agarose gel electrophoresis, sodium dodecyl sulfate-polyacrylamide gel electrophoresis (SDS-PAGE), Tris-HCl polyacrylamide gels, non-denaturing protein gels, two-dimensional gel electrophoresis (2DE), and the like), immunochemically (i.e., radioimmunoassay, immunoblotting, immunoprecipitation, immunofluorescence, enzyme-linked immunosorbent assay), by "proteomics technology", or by "genomic analysis." For example, at the nucleic acid level, Northern and Southern hybridization analysis, as well as ribonuclease protection assays using probes which specifically recognize one or more of these sequences can be used to determine gene expression. Alternatively, expression can be measured using reverse-transcription-based PCR assays (RT-PCR), e.g., using primers specific for the differentially expressed sequence of genes. Expression can also be determined at the protein level, e.g., by measuring the levels of peptides encoded by the gene products described herein, or activities thereof. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the marker genes according to the activity of each protein analyzed.

"Proteomics technology" includes, but is not limited to, surface enhanced laser desorption ionization (SELDI), matrix-assisted laser desorption ionization-time of flight (MALDI-TOF), high performance liquid chromatography (HPLC), liquid chromatography with or without mass spectrometry (LC/MS), tandem LC/MS, protein arrays, peptide arrays, and antibody arrays.

"Genome analysis" can comprise, for example, polymerase chain reaction (PCR), real-time PCR (such as by Light Cycler®, available from Roche Applied Sciences), serial analysis of gene expression (SAGE), Northern blot analysis, and Southern blot analysis.

Microarray technology can be used as a tool for analyzing gene or protein expression, comprising a small membrane or solid support (such as but not limited to microscope glass slides, plastic supports, silicon chips or wafers with or without fiber optic detection means, and membranes including nitrocellulose, nylon, or polyvinylidene fluoride). The solid support can be chemically (such as silanes, streptavidin, and numerous other examples) or physically derivatized (for example, photolithography) to enable binding of the analyte of interest, usually nucleic acids, proteins, or metabolites or fragments thereof. The nucleic acid or protein can be printed (i.e., inkjet printing), spotted, or synthesized in situ. Deposition of the nucleic acid or protein of interest can be achieved by xyz robotic microarrayers, which utilize automated spotting devices with very precise movement controls on the x-, y-, and z-axes, in combination with pin technology to provide accurate, reproducible spots on the arrays. The analytes of interest are placed on the solid support in an orderly or fixed arrangement so as to facilitate easy identification of a particularly desired analyte. A number of microarray formats are commercially available from, inter alia, Affymetrix, ArrayIt, Agilent Technologies, Asper Biotech, BioMicro, CombiMatrix, GenePix, Nanogen, and Roche Diagnostics.

The nucleic acid or protein of interest can be synthesized in the presence of nucleotides or amino acids tagged with one or more detectable labels. Such labels include, for example, fluorescent dyes and chemiluminescent labels. In particular, for microarray detection, fluorescent dyes such as but not limited to rhodamine, fluorescein, phycoerythrin, cyanine dyes like Cy3 and Cy5, and conjugates like streptavidin-phycoerythrin (when nucleic acids or proteins are tagged with biotin) are frequently used.

Detection of fluorescent signals and image acquisition are typically achieved using confocal fluorescence laser scanning or photomultiplier tube, which provide relative signal intensities and ratios of analyte abundance for the nucleic acids or proteins represented on the array. A wide variety of different scanning instruments are available, and a number of image acquisition and quantification packages are associated with them, which allow for numerical evaluation of combined selection criteria to define optimal scanning conditions, such as median value, inter-quartile range (IQR), count of saturated spots, and linear regression between pair-wise scans ($r^2$ and P). Reproducibility of the scans, as well as optimization of scanning conditions, background correction, and normalization, are assessed prior to data analysis.

Normalization refers to a collection of processes that are used to adjust data means or variances for effects resulting from systematic non-biological differences between arrays, subarrays (or print-tip groups), and dye-label channels. An array is defined as the entire set of target probes on the chip or solid support. A subarray or print-tip group refers to a subset of those target probes deposited by the same print-tip, which can be identified as distinct, smaller arrays of proves within the full array. The dye-label channel refers to the fluorescence frequency of the target sample hybridized to the chip. Experiments where two differently dye-labeled samples are mixed and hybridized to the same chip are referred to in the art as "dual-dye experiments", which result in a relative, rather than absolute, expression value for each target on the array, often represented as the log of the ratio between "red" channel and "green channel." Normalization can be performed according to ratiometric or absolute value methods. Ratiometric analyses are mainly employed in dual-dye experiments where one channel or array is considered in relation to a common reference. A ratio of expression for each target probe is calculated between test and reference sample, followed by a transformation of the ratio into $\log_2$ (ratio) to symmetrically represent relative changes. Absolute value methods are used frequently in single-dye experiments or dual-dye experiments where there is no suitable reference for a channel or array. Relevant "hits" are defined as expression levels or amounts that characterize a specific experimental condition. Usually, these are nucleic acids or proteins in which the expression levels differ significantly between different experimental conditions, usually by comparison of the expression levels of a nucleic acid or protein in the different conditions and analyzing the relative expression ("fold change") of the nucleic acid or protein and the ratio of its expression level in one set of samples to its expression in another set.

Data obtained from microarray experiments can be analyzed by any one of numerous statistical analyses, such as clustering methods and scoring methods. Clustering methods attempt to identify targets (such as nucleic acids and/or proteins) that behave similarly across a range of conditions or samples. The motivation to find such targets is driven by the assumption that targets that demonstrate similar patterns of expression share common characteristics, such as common regulatory elements, common functions, or common cellular origins.

Hierarchical clustering is an agglomerative process in which single-member clusters are fused to bigger and bigger clusters. The procedure begins by computing a pairwise distance matrix between all the target molecules, the distance matrix is explored for the nearest genes, and they are defined as a cluster. After a new cluster is formed by agglomeration of two clusters, the distance matrix is updated to reflect its distance from all other clusters. Then, the procedure searches for the nearest pair of clusters to agglomerate, and so on. This procedure results in a hierarchical dendrogram in which multiple clusters are fused to nodes according to their similarity, resulting in a single hierarchical tree. Hierarchical clustering software algorithms include Cluster and Treeview.

K-means clustering is an iterative procedure that searches for clusters that are defined in terms of their "center" points or means. Once a set of cluster centers is defined, each target molecule is assigned to the cluster it is closest to. The clustering algorithm then adjusts the center of each cluster of genes to minimize the sum of distances of target molecules in each cluster to the center. This results in a new choice of cluster centers, and target molecules can be reassigned to clusters. These iterations are applied until convergence is observed. Self-organizing maps (SOMs) are related in part to the k-means procedure, in that the data is assigned to a predetermined set of clusters. However, unlike k-means, what follows is an iterative process in which gene expression vectors in each cluster are "trained" to find the best distinctions between the different clusters. In other words, a partial structure is imposed on the data and then this structure is iteratively modified according to the data. SOM is included in many software packages, such as, for instance, GeneCluster. Other clustering methods include graph-theoretic clustering, which utilizes graph-theoretic and statistical techniques to identify tight groups of highly similar elements (kernels), which are likely to belong to the same true cluster. Several heuristic procedures are then used to expand the kernels into the full clustering. An example of software utilizing graph-theoretic clustering includes CLICK in combination with the Expander visualization tool.

Data obtained from high-throughput expression analyses can be scored using statistical methods such as parametric and non-parametric methods. Parametric approaches model expression profiles within a parametric representation and ask how different the parameters of the experimental groups are. Examples of parametric methods include, without limitation, t-tests, separation scores, and Bayesian t-tests. Non-parametric methods involve analysis of the data, wherein no a priori assumptions are made about the distribution of expression profiles in the data, and the degree to which the two groups of expression measurements are distinguished is directly examined. Another method uses the TNOM, or the threshold number of misclassifications, which measures the success in separation two groups of samples by a simple threshold over the expression values.

SAGE (serial analysis of gene expression) can also be used to systematically determine the levels of gene expression. In SAGE, short sequence tags within a defined position containing sufficient information to uniquely identify a transcript are used, followed by concatenation of tags in a serial fashion. See, for example, Velculescu V. E. et al, (1995) Science 270: 484-487. Polyadenylated RNA is isolated by oligo-dT priming, and cDNA is then synthesized using a biotin-labeled primer. The cDNA is subsequently cleaved with an anchoring restriction endonucleases, and the 3'-terminal cDNA fragments are bound to streptavidin-coated beads. An oligonucleotide linker containing recognition sites for a tagging enzyme is linked to the bound cDNA. The tagging enzyme can be a class II restriction endonucleases that cleaves the DNA at a constant number of bases 3' to the recognition site, resulting in the release of a short tag and the linker from the beads after digestion with the enzyme. The 3' ends of the released tags plus linkers are then blunt-ended and ligated to one another to form linked ditags that are approximately 100 base pairs in length. The ditags are then subjected to PCR amplification, after which the linkers and tags are released by digestion with the anchoring restriction endonucleases. Thereafter, the tags (usually ranging in size from 25-30-mers) are gel purified, concatenated, and cloned into a sequence vector. Sequencing the concatemers enables individual tags to be identified and the abundance of the transcripts for a given cell or tissue type can be determined.

The T2DBMARKER proteins, polypeptides (including the peptide inhibitors of the invention), mutations, and polymorphisms thereof can be detected in any manner known to those skilled in the art. Of particular utility are two-dimensional gel electrophoresis, which separates a mixture of proteins (such as found in biological samples such as serum) in one dimension according to the isoelectric point (such as, for example, a pH range from 5-8), and according to molecular weight in a second dimension. Two-dimensional liquid chromatography is also advantageously used to identify or detect T2DBMARKER proteins, polypeptides, mutations, and polymorphisms of the invention, and one specific example, the ProteomeLab PF 2D Protein Fractionation System is detailed in the Examples. The PF 2D system resolves proteins in one dimension by isoelectric point and by hydrophobicity in the second dimension. Another advantageous method of detecting proteins, polypeptides, mutations, and polymorphisms include SELDI (disclosed herein) and other high-throughput proteomic arrays.

T2DBMARKER proteins, polypeptides, mutations, and polymorphisms can be typically detected by contacting a sample from the subject with an antibody which binds the T2DBMARKER protein, polypeptide, mutation, or polymorphism and then detecting the presence or absence of a reaction product. The antibody may be monoclonal, polyclonal, chimeric, or a fragment of the foregoing, as discussed in detail herein, and the step of detecting the reaction product may be carried out with any suitable immunoassay. In a particularly preferred embodiment, the T2DBMARKER proteins, polypeptides, mutations, and polymorphisms can be detected with an isolated antibody of the present invention, as disclosed elsewhere in this disclosure. The isolated antibody provided by the invention can comprise, for example, a human constant region (as defined herein) and an antigen-binding region that binds to one or more T2DBMARKERS set forth in Table 1, preferably at least one, preferably two, three, four, five, six, seven, eight, nine, ten or more amino acid residues of SEQ ID NO: 1, SEQ ID NO: 2, or SEQ ID NO: 3. The sample from the subject is typically a biological fluid as described above, and may be the same sample of biological fluid used to conduct the method described above.

Immunoassays carried out in accordance with the present invention may be homogeneous assays or heterogeneous assays. In a homogeneous assay, the immunological reaction usually involves the specific antibody (e.g., anti-T2DBMARKER protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A agarose, protein G agarose, latex, polystyrene, magnetic or paramagnetic beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunoprecipitation, immunofluorescence methods, chemiluminescence methods, electrochemiluminescence or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies, such as those provided by the present invention, can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I, $^{131}$I), enzyme labels (e.g., horseradish peroxidase, alkaline phosphatase), and fluorescent labels (e.g., fluorescein, Alexa, green fluorescent protein) in accordance with known techniques.

Antibodies can also be useful for detecting post-translational modifications of T2DBMARKER proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For T2DBMARKER proteins, polypeptides, mutations, and polymorphisms known to have enzymatic activity, the activities can be determined in vitro using enzyme assays known in the art. Such assays include, without limitation, kinase assays (such as those exemplified in Example 5 herein), phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

Using sequence information provided by the database entries for the T2DBMARKER sequences, expression of the T2DBMARKER sequences can be detected (if present) and measured using techniques well known to one of ordinary skill in the art. For example, sequences within the sequence database entries corresponding to T2DBMARKER sequences, or within the sequences disclosed herein, can be used to construct probes for detecting T2DBMARKER RNA sequences in, e.g., Northern blot hybridization analyses or methods which specifically, and, preferably, quantitatively amplify specific nucleic acid sequences. As another example, the sequences can be used to construct primers for specifically amplifying the T2DBMARKER sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences.

Alternatively, T2DBMARKER protein and nucleic acid metabolites or fragments can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, surface-enhanced laser desorption ionization (SELDI), ion spray spectroscopy combined with mass spectrometry, capillary electrophoresis, NMR and IR detection. (See, WO 04/056456 and WO 04/088309, each of which are hereby incorporated by reference in their entireties) In this regard, other T2DBMARKER analytes can be measured using the above-mentioned detection methods, or other methods known to the skilled artisan.

Kits

The invention also includes a T2DBMARKER-detection reagent, e.g., nucleic acids that specifically identify one or more T2DBMARKER nucleic acids by having homologous nucleic acid sequences, such as oligonucleotide sequences, complementary to a portion of the T2DBMARKER nucleic acids or antibodies to proteins encoded by the T2DBMARKER nucleic acids packaged together in the form of a kit. The kits of the present invention allow one of skill in the art to generate the reference and subject expression profiles disclosed herein. The kits of the invention can also be used to advantageously carry out any of the methods provided in this disclosure. The oligonucleotides can be fragments of the T2DBMARKER genes. For example the oligonucleotides can be 200, 150, 100, 50, 25, 10 or less nucleotides in length. The T2DBMARKER-detection reagents can also comprise, inter alia, antibodies or fragments of antibodies, and aptamers. The kit may contain in separate containers a nucleic acid or antibody (either already bound to a solid matrix or packaged separately with reagents for binding them to the matrix), control formulations (positive and/or negative), and/or a detectable label. Instructions (e.g., written, tape, VCR, CD-ROM, etc.) for carrying out the assay detecting one or more T2DBMARKERS of the invention may be included in the kit. The assay may for example be in the form of a Northern blot hybridization or a sandwich ELISA as known in the art. Alternatively, the kit can be in the form of a microarray as known in the art.

Diagnostic kits for carrying out the methods described herein are produced in a number of ways. Preferably, the kits of the present invention comprise a control (or reference) sample derived from a subject having normal glucose levels. Alternatively, the kits can comprise a control sample derived from a subject who has been diagnosed with or identified as suffering from type 2 Diabetes or a pre-diabetic condition. In one embodiment, the diagnostic kit comprises (a) an antibody (e.g., fibrinogen αC domain peptide) conjugated to a solid support and (b) a second antibody of the invention conjugated to a detectable group. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. Alternatively, a test kit contains (a) an antibody of the invention, and (b) a specific binding partner for the antibody conjugated to a detectable group. The test kit may be packaged in any suitable manner, typically with all elements in a single container, optionally with a sheet of printed instructions for carrying out the test.

For example, T2DBMARKER detection reagents can be immobilized on a solid matrix such as a porous strip to form at least one T2DBMARKER detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of T2DBMARKERS present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by T2DBMARKERS 1-548. In various embodiments, the expression of 2, 3, 4, 5, 6, 7, 8, 9, 10, 15, 20, 25, 30, 40, 50, or more of the T2DBMARKERS 1-548 can be identified by virtue of binding to the array. The substrate array can be on, e.g., a solid substrate, e.g., a "chip"

as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.).

The skilled artisan can routinely make antibodies, nucleic acid probes, e.g., oligonucleotides, aptamers, siRNAs, antisense oligonucleotides, against any of the T2DBMARKERS in Table 1. The Examples presented herein describe generation of monoclonal antibodies in mice, as well as generation of polyclonal hyperimmune serum from rabbits. Such techniques are well-known to those of ordinary skill in the art.

Peptides, Proteins, and Nucleic Acids of the Invention

As used herein, a "protein," "polypeptide," or "peptide" generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein.

The size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

The peptides of the invention can be isolated, synthetic, or recombinant peptides that can be about 7 to 100 amino acids in length, comprising one or more of the motifs "FNRPFL" (SEQ ID NO: 6), "FMS/GKVT/VNP" (SEQ ID NO: 7), "R[S/K]XXPP" or "SXXPP", preferably of 100 amino acids or less. Peptide inhibitors of about 7-100 amino acid residues or greater are believed to be sufficient to inhibit kinase activity. A peptide of the invention may be 50, 30, 20, 10 or 5 amino acids or less, including all intervening peptide lengths. The peptide may comprise 4, 5, 6, 7, 8, 9, 10, 11, 12, 13, 14, 15, 16, 17, or 18 contiguous amino acids of one or more peptide sequences identified herein. The peptide inhibitors can be about 10-85 amino acid residues in length. Inhibitors of 12-60 amino acid residues in length are preferred, with a length of 12-50 amino acids being more preferred, and 12-40 amino acids most preferred.

A peptide inhibitor of the invention may include, but is not limited to, one or more of the amino acid sequences provided in SEQ ID NO:1, SEQ ID NO:2, and SEQ ID NO:3. The peptide inhibitors of the present invention have been shown to strongly inhibit kinases implicated in Diabetes (including, without limitation, mitogen activated protein (MAP) kinases such as p70S6K, protein kinase B isoforms such as PKBβ, protein kinase C isoforms such as PKCζ, and SGK) with $IC_{50}$ values ranging from 0.3 to 2 μM, as measured by in vitro kinase assay (see Example 6).

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moiety. In particular embodiments, the sequence of residues of the protein or peptide may be interrupted by one or more non-amino acid moieties.

Accordingly, the term "protein, polypeptide, or peptide" encompasses amino acid sequences comprising at least one of the 20 common amino acids found in naturally occurring proteins, or at least one modified or unusual amino acid, including but not limited to Aad, 2-Aminoadipic acid; EtAsn, N-Ethylasparagine; Baad, 3-Aminoadipic acid, Hyl, Hydroxylysine; Bala, β-alanine, β-Amino-propionic acid; AHyl, allo-Hydroxylysine; Abu, 2-Aminobutyric acid; 3Hyp, 3-Hydroxyproline; 4Abu, 4-Aminobutyric acid, piperidinic acid; 4Hyp, 4-Hydroxyproline; Acp, 6-Aminocaproic acid, Ide, Isodesmosine; Ahe, 2-Aminoheptanoic acid; AIle, allo-Isoleucine; Aib, 2-Aminoisobutyric acid; MeGly, N-Methylglycine, sarcosine; Baib, 3-Aminoisobutyric acid; MeIle, N-Methylisoleucine; Apm, 2-Aminopimelic acid; MeLys, 6-N-Methyllysine; Dbu, 2,4-Diaminobutyric acid; MeVal, N-Methylvaline; Des, Desmosine; Nva, Norvaline; Dpm, 2,2'-Diaminopimelic acid; Nle, Norleucine; Dpr, 2,3-Diaminopropionic acid; Orn, Ornithine; and EtGly, N-Ethylglycine.

The amino acid residues described herein are preferably in the "L" isomeric form. However, residues in the "D" isomeric form can be substituted for any L-amino acid residue, as long as the peptide inhibitors retain the ability to inhibit kinases. This definition includes, unless otherwise specifically indicated, chemically-modified amino acids, including amino acid analogs (such as penicillamine, 3-mercapto-D-valine), naturally-occurring non-proteogenic amino acids (such as norleucine), and chemically-synthesized compounds that have properties known in the art to be characteristic of an amino acid. The term "proteogenic" indicates that the amino acid can be incorporated into a protein in a cell through metabolic pathways well-known to those skilled in the art.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases, which are well known to those skilled in the art. The coding regions for known genes may be amplified and/or expressed using the techniques disclosed herein or as would be know to those of ordinary skill in the art. Alternatively, various commercial preparations of proteins, polypeptides and peptides are known to those of skill in the art.

The peptide can be a peptide "mimetic". Thus, one aspect of the present invention provides for peptidomimetics which mimic the structural features of the critical amino acid motif "FNRPFL" (SEQ ID NO: 6), "FMS/GKVT/VNP" (SEQ ID NO: 7), "R[S/K]XXPP" or "SXXPP". Although most kinase inhibitors are expected to be peptides, other non-peptide inhibitors of kinases can be identified. The peptidomimetics that are non-peptide in nature can be designed and synthesized by standard organic chemical methods. The peptidomimetics that are non-peptide in nature can be even more advantageous in therapeutic use, by displaying properties such as resistance to degradation, cell permeability, and the ability to be formulated for oral administration.

Peptidomimetics are small molecules that can bind to proteins by mimicking certain structural aspects of peptides and proteins. See, for example, Johnson et al., 1993, incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics. They are used extensively as agonists and antagonists of protein and peptide ligands of cellular receptors and as substrates and substrate analogs for enzymes. Some examples include, without limitation, morphine alkaloids (such as, for example, naturally-occurring endorphin analogs), penicillins (semi-synthetic), and HIV protease inhibitors (synthetic). Such compounds can comprise structural features that mimic a peptide or a protein and as such are recognized and bound by other proteins. Binding the peptidomimetic either induces the binding protein to carry out the normal function caused by such binding (agonist) or disrupts such function (antagonist, inhibitor).

One goal in the design of peptide mimetics has been to reduce the susceptibility of mimetics to cleavage and inactivation by peptidases. In one approach, such as disclosed by Sherman et al (1990), one or more amide bonds have been replaced in an essentially isosteric manner by a variety of chemical functional groups. This stepwise approach has met with some success in that active analogs have been obtained. In some instances, these analogs have been shown to possess longer biological half-lives than their naturally-occurring counterparts. In another approach, a variety of uncoded or modified amino acids, such as D-amino acids and N-methyl amino acids, have been used to modify peptides. In yet other approaches, a presumed bioactive conformation can be stabilized by a covalent modification, such as cyclization or by incorporation of γ-lactam or other types of bridges. See, e.g., Veber et al (1978) and Thorsett et al (1983). Another approach by Rich (1986) involves designing peptide mimics through the application of the transition state analog concept in enzyme inhibitor design. For example, it is known that the secondary alcohol of statine mimics the tetrahedral transition state of the sessile amide bond of the pepsin substrate. Nicolaou et al (1990) disclosed non-peptide somatostatin mimics.

U.S. Pat. No. 5,552,534 discloses non-peptide compounds that can mimic or inhibit the chemical and/or biological activity of a variety of peptides. These non-peptide compounds can be produced by appending to certain core species, such as the tetrahydropyranyl ring, chemical functional groups which cause the compounds to be at least partially crossreactive with the peptide. Compounds which mimic or inhibit peptides can be, in varying degrees, crossreactive with each other. Other techniques for preparing peptidomimetics are disclosed in, without limitation, U.S. Pat. Nos. 5,550,251 and 5,288,707.

Protein phosphorylation plays a crucial part in the biochemical control of cellular activity. Phosphorylation usually means formation of a phosphate ester bond between a phosphate ($PO_4$) group and an amino acid containing a hydroxyl (OH) group (such as tyrosine, serine and threonine). Many phosphorylation sites in proteins act as recognition elements for binding to other proteins, and those binding events activate or deactivate signaling and other pathways. Protein phosphorylation thus acts as a switch to turn biochemical signaling on and off. Phosphopeptide mimetics are a subclass of peptidomimetics that contain analogs of phosphorylated tyrosine, serine and threonine. Phosphate esters may be hydrolyzed by various enzymes, thus turning off a phosphorylation signal. Phosphopeptide mimetics, however, usually contain non-hydrolyzable analogs to prevent inactivation (Burke et al, 1994a; Burke et al, 1996a; Chen et al, 1995; Wiemann et al, 2000; Shapiro et al, 1997; Otaka et al, 1995; Otaka et al, 2000). General examples of phosphopeptide mimetics in the art include SH2 domain analogs (Burke et al, 1994a; Fu et al, 1998; Gao et al, 2000; Mikol et al, 1995; Ye et al, 1995), transcription factor NF-(kappa)B analog (McKinsey et al, 1997), P53 analog (Higashimoto et al, 2000) and protein-tyrosine phosphatase inhibitors (Burke et al, 1994b; Burke et al, 1996b; Groves et al, 1998; Kole et al, 1995; Kole et al, 1997; Roller et al, 1998).

Commercially available software packages can be used to design small peptides and/or peptidomimetics containing, phosphoserine or phosphothreonine analogs, preferably non-hydrolyzable analogs, as specific antagonists/inhibitors. Suitable commercially available software for analyzing crystal structure, designing and optimizing small peptides and peptidomimetics include, but are not limited to: Macromolecular X-ray Crystallography QUANTA Environment (Molecular Simulations, Inc.); TeXsan, BioteX, and SQUASH (Molecular Structure Corporation); and Crystallographica (Oxford Cryostsystems).

The peptide inhibitors of the present invention also include salts and chemical derivatives of the peptides. "Chemical derivative" can refer to a peptide of the invention having one or more residues chemically derivatized by reaction of a functional side group. Such derivatized molecules can include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The chemical derivatization does not comprehend changes in functional groups which change one amino acid to another.

Some useful modifications are designed to increase the stability of the peptide inhibitor in solution and, therefore, serve to prolong the half-life of the peptide inhibitor in solutions, particularly biological fluids, such as blood, plasma or serum, by blocking proteolytic activity in the blood. A peptide inhibitor can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using a "L" amino acid in place of a "D" amino acid at the termini, cyclization of the peptide inhibitor, and amide rather than amino or carboxy termini to inhibit exopeptidase activity.

A peptide inhibitor of the invention may or may not be glycosylated. The peptide inhibitors are not glycosylated, for example, when produced directly by peptide synthesis techniques or are produced in a prokaryotic cell transformed with a recombinant polynucleotide. Peptide molecules produced in eukaryotic expression systems (such as, for example, *Saccharomyces cerevisiae*-based expression systems, baculovirus-based expression systems utilizing for example, Sf9 insect cells, and mammalian expression systems) are typically glycosylated.

The peptide inhibitors of the invention can be produced by well known chemical procedures, such as solution or solid-phase peptide synthesis, or semi-synthesis in solution beginning with protein fragments coupled through conventional solution methods, as described by Dugas et al (1981). Alternatively, a peptide inhibitor of the invention can be synthesized by using well known methods, including recombinant methods and chemical synthesis.

A peptide inhibitor of the invention can be chemically synthesized, for example, by the solid phase peptide synthesis of Merrifield et al (1964). Alternatively, a peptide inhibitor of the invention can be synthesized using standard solution methods (see, for example, Bodanszky, 1984). Newly synthesized peptides can be purified, for example, by high performance liquid chromatography (HPLC), and can be characterized using, for example, mass spectrometry or amino acid sequence analysis.

The peptide inhibitors of the invention can be particularly useful when they are maintained in a constrained secondary conformation. The terms "constrained secondary structure," "stabilized" and "conformationally stabilized" indicate that the peptide bonds comprising the peptide are not able to rotate freely but instead are maintained in a relatively fixed structure. A method for constraining the secondary structure of a newly synthesized linear peptide is to cyclize the peptide using any of various methods well known in the art. For example, a cyclized peptide inhibitor of the invention can be prepared by forming a peptide bond between non-adjacent amino acid residues as described, for example, by Schiller et al (1985). Peptides can be synthesized on the Merrifield resin by assembling the linear peptide chain using N α-Fmoc-amino acids and Boc and tertiary-butyl proteins. Following the release of the peptide from the resin, a peptide bond can be formed between the amino and carboxy termini.

A newly synthesized linear peptide can also be cyclized by the formation of a bond between reactive amino acid side chains. For example, a peptide containing a cysteine-pair can be synthesized, with a disulfide bridge, can be formed by oxidizing a dilute aqueous solution of the peptide with $K_3Fe(CN)_6$. Alternatively, a lactam such as an ∈-(γ-glutamyl)-lysine bond can be formed between lysine and glutamic acid residues, a lysinonorleucine bond can be formed between lysine and leucine residues or a dityrosine bond can be formed between two tyrosine residues. Cyclic peptides can be constructed to contain, for example, four lysine residues, which can form the heterocyclic structure of desmosine (see, for example, Devlin, 1997). Methods for forming these and other bonds are well known in the art and are based on well-known rules of chemical reactivity (Morrison et al, 1992).

Alternatively, the peptide inhibitor of the invention can be produced recombinantly. Systems for cloning and expressing polypeptide of the invention include various microorganisms and cells that are well known in recombinant technology. These include, for example, various strains of *E. coli, Bacillus, Streptomyces*, and *Saccharomyces*, as well as mammalian, yeast and insect cells. The peptide inhibitor of the invention can be produced as a peptide or fusion protein. Suitable vectors for producing the peptide inhibitor are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

The isolated, synthetic, or recombinant peptide may be attached to a macromolecular complex. The macromolecular complex can be, without limitation, a virus, a bacteriophage, a bacterium, a liposome, a microparticle, a nanoparticle (e.g., a gold nanoparticle), a magnetic bead, a yeast cell, a mammalian cell, a cell or a microdevice. These are representative examples only and macromolecular complexes within the scope of the present invention can include virtually any complex that can be attached to a peptide inhibitor and administered to a subject. The isolated, synthetic, or recombinant peptide may also be attached to a eukaryotic expression vector, more preferably a gene therapy vector.

The isolated peptide can be attached to a solid support, such as, for example, magnetic beads, Sepharose beads, agarose beads, a nitrocellulose membrane, a nylon membrane, a column chromatography matrix, a high performance liquid chromatography (HPLC) matrix or a fast performance liquid chromatography (FPLC) matrix.

Other embodiments concern fusion proteins. These molecules generally have all or a substantial portion of the peptides of the invention, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as, for example, active sites from enzymes, glycosylation domains, cellular targeting signals or transmembrane regions.

The fusion proteins of the instant invention can comprise a peptide of the invention linked to a therapeutic protein or peptide. Examples of proteins or peptides that may be incorporated into a fusion protein include, but are not limited to, cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually any protein or peptide could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

In certain embodiments, it may be desirable to couple specific bioactive agents to one or more targeting moieties for targeted delivery to an organ, tissue or cell type. Such agents include, but are not limited to, cytokines, chemokines, pro-apoptosis factors and anti-angiogenic factors. The term "cytokine" is a generic term for proteins released by one cell population that act on another cell as intercellular mediators.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -.β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines.

In certain embodiments, the targeting moieties of the present invention may be attached to imaging agents of use for imaging and diagnosis of various diseased organs, tissues or cell types. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include $^{211}$astatine, $^{14}$carbon, $^{51}$chromium, $^{36}$chlorine, $^{57}$cobalt, $^{58}$cobalt, $^{67}$copper, $^{152}$Eu, $^{67}$gallium, $^{3}$hydrogen, $^{123}$iodine, $^{125}$iodine, $^{131}$iodine, $^{111}$indium, $^{59}$iron, $^{32}$phosphorus, $^{186}$rhenium, $^{188}$rhenium, $^{75}$selenium, $^{35}$sulphur, $^{99m}$technicium and $^{90}$yttrium. $^{125}$I is often being preferred for use in certain embodiments, and $^{99m}$technicium and $^{111}$indium are also often preferred due to their low energy and suitability for long range detection.

Radioactively labeled proteins or peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides according to the invention may be labeled with technetium-99m by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA). Also contemplated for use are fluorescent labels, including rhodamine, fluorescein isothiocyanate and renographin.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

In still further embodiments, a targeting moiety may be operatively coupled to a nanoparticle. Nanoparticles include, but are not limited to colloidal gold and silver nanoparticles. Metal nanoparticles exhibit colors in the visible spectral region. It is believed that these colors are the result of excitation of surface plasmon resonances in the metal particles and are extremely sensitive to particle size, shape, and aggregation state; dielectric properties of the surrounding medium; adsorption of ions on the surface of the particles (For examples, see U.S. Patent Application Publication No. 20040023415, which is incorporated herein by reference).

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. Nos. 5,603,872 and 5,401,511, each specifically incorporated herein by reference in its entirety. Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar vesicles (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites are dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups.

In certain embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulfate, polyethylene glycol (PEG), antibodies and the like, or by heat denaturation, followed by: centrifugation; chromatography steps such as ion exchange, gel filtration, reverse phase, hydroxyapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

The invention also concerns isolated nucleic acids encoding the peptide inhibitors described herein. A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide. Nucleic acids according to the present invention may encode a peptide/peptide inhibitor, a targeting antibody, a therapeutic polypeptide a fusion protein or other protein or peptide. The nucleic acid may be derived from genomic DNA, complementary DNA (cDNA) or synthetic DNA.

In certain aspects, the nucleic acids may be 300 nucleotides or less in length. In still further embodiments the nucleic acids may be 270, 240, 210, 180, 150, 120, 90, 60, 30 or even 9 nucleotides in length. Exemplary non-limiting nucleic acid sequences include those that encode the peptides provided in SEQ ID NO:1, SEQ ID NO:2, or SEQ ID NO:3.

It is contemplated that the peptides, antibodies, and fusion proteins of the invention may be encoded by any nucleic acid sequence that encodes the appropriate amino acid sequence. The design and production of nucleic acids encoding a desired amino acid sequence is well known to those of skill in the art, using standardized codon tables. In preferred embodiments, the codons selected for encoding each amino acid may be modified to optimize expression of the nucleic acid in the host cell of interest.

There are a number of ways in which gene therapy vectors may introduced into cells. One or more isolated nucleic acid can be incorporated into a eukaryotic or a prokaryotic expression vector. The vector can be, without limitation, a plasmid, a cosmid, a yeast artificial chromosome (YAC), a bacterial artificial chromosome (BAC), a virus or a bacteriophage. The isolated nucleic acid can also be operatively linked to a leader sequence that localizes the expressed peptide to the extracellular surface of a host cell, or to a specific organelle within the host cell (such as, for example, localization to the nucleus of a cell, via a nuclear localization sequence, or NLS). In certain embodiments of the invention, the gene therapy vector comprises a virus. The ability of certain viruses to enter cells via receptor-mediated endocytosis, to integrate into host cell genome or be maintained episomally, and express viral genes stably and efficiently have made them attractive candidates for the transfer of foreign genes into mammalian cells (Ridgeway, 1988; Nicolas and Rubinstein, 1988.; Baichwal and Sugden, 1986; Temin, 1986). Preferred gene therapy vectors are generally viral vectors. DNA viruses used as gene therapy vectors include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986).

Other gene transfer vectors may be constructed from retroviruses. (Coffin, 1990.) In order to construct a retroviral vector, a nucleic acid encoding protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., 1975).

Other viral vectors may be employed as targeted gene therapy vectors. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984), and herpes viruses may be employed.

In a further embodiment of the invention, gene therapy construct may be entrapped in a liposome. Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa, and hepatoma cells. Nicolau et al., (1987.) accomplished successful liposome-mediated gene transfer in rats after intravenous injection.

Gene therapy vectors of the invention may comprise various transgenes, which are typically encoded DNA or RNA of an expression vector. DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An anti-sense polynucleotide is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15-50 base pairs and preferably 21-25 base pairs and having a nucleotide sequence identical or nearly identical to an expressed target gene or RNA within the cell. Interference may result in suppression of expression. The polynucleotide can also be a sequence whose presence or expression in a cell alters the expression or function of cellular genes or RNA. In addition, DNA and RNA may be single, double, triple, or quadruple stranded.

Antibodies

The present invention also provides antibodies that are capable of binding to one or more T2DBMARKERS presented in Table 1, such as the peptide inhibitors of the invention, and preferably, antibodies that are capable of binding to one or more amino acids of SEQ ID NO: 1, 2, or 3. The term "antibody" as used in the context of the present invention includes polyclonal antibodies, monoclonal antibodies (mAbs), chimeric antibodies, anti-idiotypic (anti-Id) antibodies, that can be labeled in soluble or bound form, as well as fragments, regions, or derivatives thereof, provided by any known technique, such as, but not limited to, enzymatic cleavage, peptide synthesis, or recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be human, murine, monkey, rat, hamster, rabbit, or chicken in origin and obtained by methods known to those skilled in the art. See, for example Kohler and Milstein, Nature 256:495-497 (1975); U.S. Pat. No. 4,376,110; Ausubel et al., eds., Current Protocols in Molecular Biology, Greene Publishing Assoc. and Wiley Interscience, N.Y., (1987, 1992); and Harlow and Lane ANTIBODIES. A Laboratory Manual Cold Spring Harbor Laboratory (1988); Colligan et al., eds., Current Protocols in Immunology, Greene Publishing Assoc. and Wiley Interscience, N.Y., (1992, 1993), the contents of which references are incorporated entirely herein by reference.

Such antibodies may be of any immunoglobulin class including IgG, IgM, IgE, IgD, IgA, GILD and any subclass thereof. A hybridoma producing a mAb of the present invention may be cultivated in vitro, in situ or in vivo. Production of high titers of mAbs in vivo or in situ makes this a preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mabs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:3273-3277 (1984); Morrison et al., Proc. Natl. Acad. Sci. USA 81:6851-6855 (1984); Boulianne et al., Nature 312:643-646 (1984); Cabilly et al., European Patent Application 125023 (published Nov. 14, 1984); Neuberger et al., Nature 314:268-270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066-1074 (1986); Robinson et al., International Patent Publication No. PCT/US86/02269 (published 7 May 1987); Liu et al., Proc. Natl. Acad. Sci. USA 84:3439-3443 (1987); Sun et al., Proc. Natl. Acad. Sci. USA 84:214-218 (1987); Better et al., Science 240:1041-1043 (1988); and Harlow and Lane Antibodies: a Laboratory Manual Cold Spring Harbor Laboratory (1988)). These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Antibodies of the present invention can include at least one of a heavy chain constant region ($H_c$), a heavy chain variable region ($H_v$), a light chain variable region ($L_v$) and a light chain constant region ($L_c$), wherein a polyclonal Ab, monoclonal Ab, fragment and/or regions thereof include at least one heavy chain variable region ($H_v$) or light chain variable region ($L_v$) which binds a portion of SEQ ID NO: 1, SEQ ID NO: 2, or SEQ ID NO: 3.

Preferred methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference.

The techniques to raise antibodies of the present invention to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues.

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chieric antibody is tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ chain).

Murine and chimeric antibodies, fragments and regions of the present invention comprise individual heavy (H) and/or light (L) immunoglobulin chains. A chimeric H chain comprises an antigen binding region derived from the H chain of a non-human antibody specific for one or more T2DBMARKERS or preferably, SEQ ID NO: 1, SEQ ID NO: 2, or SEQ ID NO: 3, which is linked to at least a portion of a human H chain C region ($C_H$), such as $CH_1$ or $CH_2$.

A chimeric L chain according to the present invention, comprises an antigen binding region derived from the L chain of a non-human antibody specific for one or more T2DBMARKERS or preferably, SEQ ID NO: 1, 2, or 3, linked to at least a portion of a human L chain C region ($C_L$). Antibodies, fragments or derivatives having chimeric H chains and L chains of the same or different variable region binding specificity, can also be prepared by appropriate association of the individual polypeptide chains, according to known method steps, e.g., according to Ausubel, Harlow, and Colligan, the contents of which references are incorporated entirely herein by reference. With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

The hybrid cells are formed by the fusion of a non-human anti-T2DBMARKER or anti-SEQ ID NO: 1 (e.g., anti-D3 as disclosed in the Examples) antibody-producing cell, typically a spleen cell of an animal immunized against either natural or recombinant T2DBMARKERS or SEQ ID NO: 1, 2, or 3, or a peptide fragment of any one or more of the T2DBMARKERS or SEQ ID NO:1, 2, or 3. Alternatively, the non-human antibody-producing cell can be a B lymphocyte obtained from the blood, spleen, lymph nodes or other tissue of an animal immunized with one or more T2DBMARKERS, or the full or partial amino acid sequence of SEQ ID NO: 1, SEQ ID NO: 2, or SEQ ID NO: 3.

The second fusion partner, which provides the immortalizing function, can be a lymphoblastoid cell or a plasmacytoma or myeloma cell, which is not itself an antibody producing cell, but is malignant. Preferred fusion partner cells include the hybridoma SP2/0-Ag14, abbreviated as SP2/0 (ATCC CRL1581) and the myeloma P3X63Ag8 (ATCC TIB9), or its derivatives. See, e.g, Ausubel, Harlow, and Colligan, the contents of which are incorporated entirely herein by reference.

The antibody-producing cell contributing the nucleotide sequences encoding the antigen-binding region of the chimeric antibody of the present invention can also be produced by transformation of a non-human, such as a primate, or a human cell. For example, a B lymphocyte which produces an antibody of the invention can be infected and transformed with a virus such as Epstein-Barr virus to yield an immortal antibody producing cell (Kozbor et al., Immunol. Today 4:72-79 (1983)). Alternatively, the B lymphocyte can be transformed by providing a transforming gene or transforming gene product, as is well-known in the art. See, e.g, Ausubel infra, Harlow infra, and Colligan infra, the contents of which references are incorporated entirely herein by reference.

Monoclonal antibodies obtained by cell fusions and hybridomas are accomplished by standard procedures well known to those skilled in the field of immunology. Fusion partner cell lines and methods for fusing and selecting hybridomas and screening for mAbs are well known in the art. See, e.g, Ausubel, Harlow, and Colligan, the contents of which are incorporated entirely herein by reference.

The mAbs of the present invention can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

The invention also provides for "derivatives" of the murine or chimeric antibodies, fragments, regions or derivatives thereof, which term includes those proteins encoded by truncated or modified genes to yield molecular species functionally resembling the immunoglobulin fragments. The modifications include, but are not limited to, addition of genetic sequences coding for cytotoxic proteins such as plant and bacterial toxins. The fragments and derivatives can be produced from any of the hosts of this invention. Alternatively, antibodies, fragments and regions can be bound to cytotoxic proteins or compounds in vitro, to provide cytotoxic antibodies which would selectively kill cells having receptors corresponding to one or more T2DBMARKERS.

Fragments include, for example, Fab, Fab', F(ab')$_2$ and Fv. These fragments lack the Fc fragment of intact antibody, clear more rapidly from the circulation, and can have less non-specific tissue binding than an intact antibody (Wahl et al., J. Nucl. Med. 24:316-325 (1983)). These fragments are produced from intact antibodies using methods well known in the art, for example by proteolytic cleavage with enzymes such as papain (to produce Fab fragments) or pepsin (to produce F(ab')$_2$ fragments).

The identification of these antigen binding region and/or epitopes recognized by mAbs of the present invention provides the information necessary to generate additional monoclonal antibodies with similar binding characteristics and therapeutic or diagnostic utility that parallel the embodiments of this application.

Recombinant murine or chimeric murine-human or human-human antibodies that bind an epitope included in the amino acid sequences residues of SEQ ID NO:1, SEQ ID NO: 2, or SEQ ID NO: 3 can be provided according to the present invention using known techniques based on the teaching provided herein. See, e.g., Ausubel et al., eds. Current Protocols in Molecular Biology, Wiley Interscience, N.Y. (1987, 1992, 1993); and Sambrook et al. Molecular Cloning: A Laboratory Manual, Cold Spring Harbor Laboratory Press (1989), the entire contents of which are incorporated herein by reference.

The DNA encoding an antibody of the present invention can be genomic DNA or cDNA which encodes at least one of the heavy chain constant region ($H_c$), the heavy chain variable region ($H_v$), the light chain variable region ($L_v$) and the light chain constant regions ($L_c$). A convenient alternative to the use of chromosomal gene fragments as the source of DNA encoding the murine V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a murine V region antigen-binding segment capable of binding to one or more T2DBMARKERS, for example, SEQ ID NO: 1, 2, or 3, can be provided using known methods. Probes that bind a portion of a DNA sequence encoding the antibodies of the present invention can be used to isolate DNA from hybridomas expressing antibodies, fragments or regions, as presented herein, according to the present invention, by known methods.

Oligonucleotides representing a portion of the variable region are useful for screening for the presence of homologous genes and for the cloning of such genes encoding variable or constant regions of antibodies according to the invention. Such probes preferably bind to portions of sequences which encode light chain or heavy chain variable regions which bind an epitope of one or more T2DBMARKERS, especially an epitope of at least 5 amino acids of residues 1-38 of SEQ ID NO:1, or at least 5 amino acids of SEQ ID NOs 2 or 3. Such techniques for synthesizing such oligonucleotides are well known and disclosed by, for example, Wu, et al., Prog. Nucl. Acid. Res. Molec. Biol. 21:101-141 (1978), and Ausubel et al., eds. Current Protocols in Molecular Biology, Wiley Interscience (1987, 1993), the entire contents of which are herein incorporated by reference.

Because the genetic code is degenerate, more than one codon can be used to encode a particular amino acid (Watson, et al.). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody of the invention or a fragment thereof. Such "codon usage rules" are disclosed by Lathe, et al., J. Molec. Biol. 183:1-12 (1985). Using the "codon usage rules" of Lathe, a single oligonucleotide, or a set of oligonucleotides, that contains a theoretical "most probable" nucleotide sequence capable of encoding preferred variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an antibody of the present invention or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region gene (Sambrook et al., infra).

A suitable oligonucleotide, or set of oligonucleotides, which is capable of encoding a fragment of the variable or constant region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing antibodies or variable or constant regions thereof. Single stranded oligonucleotide molecules complementary to the "most probable" variable or constant anti-T2DBMARKER region peptide coding sequences can be synthesized using procedures which are well known to those of ordinary skill in the art (Belagaje, et al., J. Biol. Chem. 254:5765-5780 (1979); Maniatis, et al., In: Molecular Mechanisms in the Control of Gene Expression, Nierlich, et al., Eds., Acad. Press, NY (1976); Wu, et al., Prog. Nucl. Acid Res. Molec. Biol. 21:101-141 (1978); Khorana, Science 203: 614-625 (1979)). Additionally, DNA synthesis can be achieved through the use of automated synthesizers. Techniques of nucleic acid hybridization are disclosed by Sambrook et al. (infra), and by Haymes, et al. (In: Nucleic Acid Hybridization, A Practical Approach, IRL Press, Washington, D.C. (1985)), which references are herein incorporated by reference.

In an alternative way of cloning a polynucleotide encoding a variable or constant region, a library of expression vectors is prepared by cloning DNA or, more preferably, cDNA (from a cell capable of expressing an antibody or variable or constant region) into an expression vector. The library can then be screened for members capable of expressing a protein which competitively inhibits the binding of an antibody, and which has a nucleotide sequence that is capable of encoding polypeptides that have the same amino acid sequence as the antibodies of the present invention or fragments thereof. In this embodiment, DNA, or more preferably cDNA, is extracted and purified from a cell which is capable of expressing an antibody or fragment. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, Harlow, Colligan; Nyyssonen et al. Bio/Technology 11:591-595 (Can 1993); Marks et al., Bio/Technology 11:1145-1149 (October 1993). Once a nucleic acid encoding such variable or constant regions is isolated, the nucleic acid can be appropriately expressed in a host cell, along with other constant or variable heavy or light chain encoding nucleic acid, in order to provide recombinant MAbs that bind one or more T2DBMARKERS with inhibitory activity. Such antibodies preferably include a murine or human variable region which contains a framework residue having complementarity determining residues which are responsible for antigen binding. Preferably, a variable light or heavy chain encoded by a nucleic acid as described above binds an epitope of at least 5 amino acids included within residues 1-38 of SEQ ID NO: 1, or an epitope of at least 5 amino acids of SEQ ID NOs 2 or 3.

Human genes which encode the constant (C) regions of the murine and chimeric antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including γ, μ, α, δ or ∈, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or μ (IgM). The human $C_L$ region can be derived from either human L chain isotype, kappa (κ) or lambda (λ).

Genes encoding human immunoglobulin C regions are obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the $CH_1$ domain and hinge region of the H chain, followed by a translational stop codon to yield the truncated molecule.

Generally, the murine, human or murine and chimeric antibodies, fragments and regions of the present invention are produced by cloning DNA segments encoding the H and L chain antigen-binding regions of an antibody, and joining these DNA segments to DNA segments encoding $C_H$ and $C_L$ regions, respectively, to produce murine, human or chimeric immunoglobulin-encoding genes.

A fused chimeric gene can be created which comprises a first DNA segment that encodes at least the antigen-binding region of non-human origin, such as a functionally rearranged V region with joining (J) segment, linked to a second DNA segment encoding at least a part of a human C region. Therefore, cDNA encoding the antibody V and C regions, the method of producing the chimeric antibody according to the present invention involves several steps, involving isolation of messenger RNA (mRNA) from the cell line producing an antibody of the invention and from optional additional antibodies supplying heavy and light constant regions; cloning and cDNA production therefrom; preparation of a full length cDNA library from purified mRNA from which the appropriate V and/or C region gene segments of the L and H chain genes can be identified with appropriate probes, sequenced, and made compatible with a C or V gene segment from another antibody for a chimeric antibody; constructing complete H or L chain coding sequences by linkage of the cloned specific V region gene segments to cloned C region gene; expressing and producing L and H chains in selected hosts, including prokaryotic and eukaryotic cells to provide murine-murine, human-murine, human-human or human murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region ($C_{\gamma 1}$). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human $C_{\gamma 1}$ region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors, which are used for carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions.

A nucleic acid sequence encoding at least one antibody or Ab fragment of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel, infra, Sambrook, infra, entirely incorporated herein by reference, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression of antibodies or Ab fragments in recoverable amounts. The precise nature of the regulatory regions needed for gene expression may vary from organism to organism, as is well known in the analogous art. See, e.g., Sambrook, supra and Ausubel supra.

The present invention accordingly encompasses the expression of antibodies or Ab fragments, in either prokaryotic or eukaryotic cells, although eukaryotic expression is preferred. Preferred hosts are bacterial or eukaryotic hosts including bacteria, yeast, insects, fungi, bird and mammalian cells either in vivo, or in situ, or host cells of mammalian, insect, bird or yeast origin. It is preferable that the mammalian cell or tissue is of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins can be achieved. The fusion proteins produced thereby may be processed in vivo or purified and processed in vitro, allowing synthesis of an antibody or Ab fragment of the present invention with a specified amino terminus sequence. Moreover, problems associated with retention of initiation codon-derived methionine residues in direct yeast (or bacterial) expression may be avoided. Sabin et al., Bio/Technol. 7(7): 705-709 (1989); Miller et al., Bio/Technol. 7(7):698-704 (1989).

Any of a series of yeast gene expression systems incorporating promoter and termination elements from the actively expressed genes coding for glycolytic enzymes produced in large quantities when yeast are grown in mediums rich in glucose can be utilized to obtain the antibodies or Ab fragments of the present invention. Known glycolytic genes can also provide very efficient transcriptional control signals. For example, the promoter and terminator signals of the phosphoglycerate kinase gene can be utilized.

Production of antibodies or Ab fragments or functional derivatives thereof in insects can be achieved, for example, by infecting the insect host with a baculovirus engineered to express a transmembrane polypeptide by methods known to those of skill. See Ausubel et al., eds. Current Protocols in Molecular Biology Wiley Interscience, 16.8-16.11 (1987, 1993).

In a preferred embodiment, the introduced nucleotide sequence will be incorporated into a plasmid or viral vector capable of autonomous replication in the recipient host. Any of a wide variety of vectors may be employed for this purpose. See, e.g., Ausubel et al., sections 1.5, 1.10, 7.1, 7.3, 8.1, 9.6, 9.7, 13.4, 16.2, 16.6, and 16.8-16.11. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors known in the art include plasmids such as those capable of replication in *E. coli* (such as, for example, pBR322, ColE1, pSC101, pACYC 184, .pi.VX). Such plasmids are, for example, disclosed by Maniatis, T., et al. (Molecular Cloning, A Laboratory Manual, Second Edition, Cold Spring Harbor Press, Cold Spring Harbor, N.Y. (1989); Ausubel, infra. *Bacillus* plasmids include pC194, pC221, pT127, etc. Such plasmids are disclosed by Gryczan, T. (In: The Molecular Biology of the Bacilli, Academic Press, NY (1982), pp. 307-329). Suitable *Streptomyces* plasmids include pIJ101 (Kendall, K. J., et al., J. Bacteriol. 169:4177-4183 (1987)), and streptomyces bacteriophages such as .phi.C31 (Chater, K. F., et al., In: Sixth International Symposium on Actinomycetales Biology, Akademiai Kaido, Budapest, Hungary (1986), pp. 45-54). *Pseudomonas* plasmids are reviewed by John, J. F., et al. (Rev. Infect. Dis. 8:693-704 (1986)), and Izaki, K. (Jpn. J. Bacteriol. 33:729-742 (1978); and Ausubel et al., supra).

Alternatively, gene expression elements useful for the expression of cDNA encoding antibodies, antibody fragments, or peptides include, but are not limited to (a) viral transcription promoters and their enhancer elements, such as the SV40 early promoter (Okayama, et al., Mol. Cell. Biol. 3:280 (1983)), Rous sarcoma virus LTR (Gorman, et al., Proc. Natl. Acad. Sci., USA 79:6777 (1982)), and Moloney murine leukemia virus LTR (Grosschedl, et al., Cell 41:885 (1985)); (b) splice regions and polyadenylation sites such as those derived from the SV40 late region (Okayarea et al., infra); and (c) polyadenylation sites such as in SV40 (Okayama et al., infra).

Immunoglobulin cDNA genes can be expressed as described by Liu et al., infra, and Weidle et al., Gene 51:21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., Protein Engineering 1:499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences. For example, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. cDNA sequences encoding other proteins can also be combined with the above-recited expression elements to achieve expression of the proteins in mammalian cells.

Each fused gene can be assembled in, or inserted into, an expression vector. Recipient cells capable of expressing the chimeric immunoglobulin chain gene product are then transfected singly with the sequence encoding the antibody, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture. The fused genes encoding the antibodies or chimeric H and L chains, or portions thereof, can be assembled in separate expression vectors that are then used to co-transfect a recipient cell.

Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes.

Examples of selectable genes for use in a bacterial system are the gene that confers resistance to ampicillin and the gene that confers resistance to chloramphenicol. Preferred selectable genes for use in eukaryotic transfectants include the xanthine guanine phosphoribosyl transferase gene (designated gpt) and the phosphotransferase gens from Tn5 (designated neo). Selection of cells expressing gpt is based on the fact that the enzyme encoded by this gene utilizes xanthine as a substrate for purine nucleotide synthesis, whereas the analogous endogenous enzyme cannot. In a medium containing mycophenolic acid, which blocks the conversion of inosine monophosphate to xanthine monophosphate, and xanthine, only cells expressing the gpt gene can survive. The product of the neo blocks the inhibition of protein synthesis by the antibiotic G418 and other antibiotics of the neomycin class.

The two selection procedures can be used simultaneously or sequentially to select for the expression of immunoglobulin chain genes introduced on two different DNA vectors into a eukaryotic cell. It is not necessary to include different selectable markers for eukaryotic cells; an H and an L chain vector, each containing the same selectable marker can be co-transfected. After selection of the appropriately resistant cells, the majority of the clones will contain integrated copies of both H and L chain vectors and/or antibody fragments. Alternatively, the fused genes encoding the chimeric H and L chains can be assembled on the same expression vector.

For transfection of the expression vectors and production of the chimeric antibody, the preferred recipient cell line is a myeloma cell. Myeloma cells can synthesize, assemble and secrete immunoglobulins encoded by transfected immunoglobulin genes and possess the mechanism for glycosylation of the immunoglobulin. A particularly preferred recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies hetero-hybridoma cells.

The expression vector carrying a chimeric antibody construct, antibody, or antibody fragment of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment (Johnston et al., Science 240:1538 (1988)). A preferred way of introducing DNA into lymphoid cells is by electroporation (Potter et al., Proc. Natl. Acad. Sci. USA 81:7161 (1984); Yoshikawa, et al., Jpn. J. Cancer Res. 77:1122-1133). In this procedure, recipient cells are subjected to an electric pulse in the presence of the DNA to be incorporated. Typically, after transfection, cells are allowed to recover in complete medium for about 24 hours, and are then seeded in 96-well culture plates in the presence of the selective medium. G418 selection is performed using about 0.4 to 0.8 mg/ml G418. Mycophenolic acid selection utilizes about 6 μg/ml plus about 0.25 mg/ml xanthine. The electroporation technique is expected to yield transfection frequencies of about $10^{-5}$ to about $10^{-4}$ for Sp2/0 cells. In the protoplast fusion method, lysozyme is used to strip cell walls from catarrhal harboring the recombinant plasmid containing the chimeric antibody gene. The resulting spheroplasts can then be fused with myeloma cells with polyethylene glycol.

The immunoglobulin genes of the present invention can also be expressed in nonlymphoid mammalian cells or in other eukaryotic cells, such as yeast, or in prokaryotic cells, in particular bacteria. Yeast provides substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides) (Hitzman, et al., 11th International Conference on Yeast, Genetics and Molecular Biology, Montpelier, France, Sep. 13-17, 1982).

Yeast gene expression systems can be routinely evaluated for the levels of production, secretion and the stability of antibody and assembled murine and chimeric antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast (see Glover, ed., DNA Cloning, Vol. II, pp 45-66, IRL Press, 1985).

Bacterial strains can also be utilized as hosts for the production of antibody molecules or peptides described by this invention, E. coli K12 strains such as E. coli W3110 (ATCC 27325), and other enterobacteria such as Salmonella typh-imurium or Serratia marcescens, and various Pseudomonas species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine and chimeric antibodies, fragments and regions or antibody chains encoded by the cloned immunoglobulin cDNAs in bacteria (see Glover, ed., DNA Cloning, Vol. I, IRL Press, 1985, Ausubel, infra, Sambrook, infra, Colligan, infra).

Preferred hosts are mammalian cells, grown in vitro or in vivo. Mammalian cells provide post-translational modifications to immunoglobulin protein molecules including leader peptide removal, folding and assembly of H and L chains, glycosylation of the antibody molecules, and secretion of functional antibody protein. Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61).

Many vector systems are available for the expression of cloned antibodies, H and L chain genes, or antibody fragments in mammalian cells (see Glover, ed., DNA Cloning, Vol. II, pp 143-238, IRL Press, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies and/or antibodies and/or antibody fragments of the invention. The co-expression can occur by using either the same or different plasmids in the same host. Genes for both H and L chains and/or antibodies and/or antibody fragments can be placed into the same plasmid, which can then be transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies and/or $H_2L_2$ molecules and/or antibody fragments via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

In addition to monoclonal or chimeric antibodies, the present invention is also directed to an anti-idiotypic (anti-Id) antibody specific for the antibodies of the invention. An anti-Id antibody is an antibody which recognizes unique determinants generally associated with the antigen-binding region of another antibody. The antibody specific for one or more T2DBMARKERS, or any of SEQ ID NO: 1, 2, or 3 is termed the idiotypic or Id antibody. The anti-Id can be prepared by immunizing an animal of the same species and genetic type (e.g. mouse strain) as the source of the Id antibody with the Id antibody or the antigen-binding region thereof. The immunized animal will recognize and respond to the idiotypic determinants of the immunizing antibody and produce an anti-Id antibody. The anti-Id antibody can also be used as an "immunogen" to induce an immune response in yet another animal, producing a so-called anti-anti-Id antibody. The anti-anti-Id can be epitopically identical to the original antibody which induced the anti-Id. Thus, by using antibodies to the idiotypic determinants of a mAb, it is possible to identify other clones expressing antibodies of identical specificity.

Accordingly, mAbs generated against one or more T2DBMARKERS according to the present invention can be used to induce anti-Id antibodies in suitable animals, such as BALB/c mice. Spleen cells from such immunized mice can be used to produce anti-Id hybridomas secreting anti-Id mAbs. Further, the anti-Id InAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of a T2DBMARKER, or preferably, an epitope containing within amino acid residues 1-38 of SEQ ID NO: 1, or within SEQ ID NO: 2, or SEQ ID NO: 3.

Other aspects of the invention provide antibodies to T2DMARKER peptides, proteins, polypeptides or antibody idiotopes thereof that are linked to at least one agent to form an antibody conjugate. To increase the efficacy of antibody molecules as diagnostic or therapeutic agents, it is conventional to link or covalently bind or complex at least one desired molecule or moiety. A reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. An example of such a detectable label is gold nanoparticles. Another such example is the formation of a conjugate comprising an antibody linked to a cytotoxic or anti-cellular agent, and may be termed "immunotoxins".

Pharmaceutical Compositions and Methods of Treatment

The invention provides pharmaceutical compositions comprising an effective amount, or a therapeutically effective amount, of one or more T2DBMARKERS disclosed herein, preferably the peptide and kinase inhibitors of the invention in a pharmaceutically acceptable carrier or diluent, for administration to a subject, such as a human patient. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

The term "treating" or "treatment" in its various grammatical forms in relation to the present invention refers to preventing (i.e. chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessarily all symptoms) of a disease or attenuating the progression of a disease.

As used herein, the term "therapeutically effective amount" is intended to qualify the amount or amounts of T2DBMARKERS or other diabetes-modulating agents that will achieve a desired biological response. In the context of the present invention, the desired biological response can be partial or total inhibition, delay or prevention of the progression of type 2 Diabetes, pre-diabetic conditions, and complications associated with type 2 Diabetes or pre-diabetic conditions; inhibition, delay or prevention of the recurrence of type 2 Diabetes, pre-diabetic conditions, or complications associated with type 2 Diabetes or pre-diabetic conditions; or the prevention of the onset or development of type 2 Diabetes, pre-diabetic conditions, or complications associated with type 2 Diabetes or pre-diabetic conditions (chemoprevention) in a subject, for example a human.

Therapeutically effective amount" as used herein can also refer to an amount that is effective to obtain the desired therapeutic result. The term "an effective amount" of, for example, the peptide kinase inhibitors of the invention refers to an amount that is effective to induce an inhibition of kinase activity, which can be kinase activity from one or more kinases implicated in type 2 Diabetes Mellitus or pre-diabetic conditions as defined herein. The inhibitory amount may be determined directly by measuring the inhibition of kinase activity, or, for example, where the desired effect is an effect on an activity downstream of a particular kinase activity in a pathway that includes one or more kinases involved in Diabetes or a pre-diabetic condition, the inhibition may be measured by measuring a downstream effect. Thus, the inhibition of kinase activity will depend in part on the nature of the inhibited pathway or process that involves kinase activity, and on the effects that inhibition of kinase activity has in a given biological context.

The amount of the inhibitor that will constitute an inhibitory amount will vary depending on such parameters as the inhibitor and its potency, the half-life of the inhibitor in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the inhibitor or that will have an effect on kinase activity, or a pathway mediated by kinase activity. It is expected that the inhibitory amount will fall in a relatively broad range that can be determined through routine trials.

The T2DBMARKERS, preferably included as part of a pharmaceutical composition, can be administered by any known administration method known to a person skilled in the art. The mode of administration can depend on the disease condition or the injury being treated. In particular, the peptide inhibitors of the invention can be administered in an amount and by a route of administration that blocks about 50% or greater of kinase phosphorylation activity, as measured by in vitro kinase assay (see Example 5). Examples of routes of administration include but are not limited to oral, nasal, ophthalmic, parenteral, intraperitoneal, intravenous, intravascular, intraarterial, intraventricular, intraepidural, intratumor, intraorbital, intracapsule, intraperitoneal, intracistern, transdermal, topical, sublingual, intramuscular, rectal, transbuccal, intranasal, liposomal, via inhalation, vaginal, mucosal, intraoccular, via local delivery by catheter or stent, by depot injection, by erodible implants, subcutaneous, intraadiposal, intraarticular, intrathecal, or in a slow release dosage form. The T2DBMARKERS or pharmaceutical compositions comprising the T2DBMARKERS can be administered in accordance with any dose and dosing schedule that achieves a dose effective to treat disease.

As examples, T2DBMARKERS or pharmaceutical compositions comprising T2DBMARKERS of the invention can be administered in such oral forms as tablets, capsules (each of which includes sustained release or timed release formulations), pills, powders, granules, elixirs, tinctures, suspensions, syrups, and emulsions. Likewise, the T2DBMARKERS or pharmaceutical compositions comprising T2DBMARKERS can be administered by intravenous (e.g., bolus or infusion), intraperitoneal, subcutaneous, intramuscular, or other routes using forms well known to those of ordinary skill in the pharmaceutical arts.

T2DBMARKERS and pharmaceutical compositions comprising T2DBMARKERS can also be administered in the form of a depot injection or implant preparation, which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

T2DBMARKERS or pharmaceutical compositions comprising T2DBMARKERS can also be administered in the form of liposome delivery systems, such as small unilamellar vesicles, large unilamellar vesicles and multilamellar vesicles. Liposomes can be formed from a variety of phospholipids, such as cholesterol, stearylamine, phosphatidylethanolamines, or phosphatidylcholines. Liposomal preparations of diabetes-modulating agents may also be used in the methods of the invention.

T2DBMARKERS or pharmaceutical compositions comprising T2DBMARKERS can also be delivered by the use of monoclonal antibodies as individual carriers to which the compound molecules are coupled.

T2DBMARKERS or pharmaceutical compositions comprising T2DBMARKERS can also be prepared with soluble polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, T2DBMARKERS or pharmaceutical compositions comprising T2DBMARKERS can be prepared with biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The T2DBMARKERS or pharmaceutical compositions comprising T2DBMARKERS can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

Suitable pharmaceutically acceptable salts of the agents described herein and suitable for use in the method of the invention, are conventional non-toxic salts and can include a salt with a base or an acid addition salt such as a salt with an inorganic base, for example, an alkali metal salt (e.g., lithium salt, sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, methanesulfonate, benzenesulfonate, p-toluenesulfonate, etc.); a salt with a basic or acidic amino acid (e.g., arginine, aspartic acid, glutamic acid, etc.) and the like.

In addition, this invention also encompasses pharmaceutical compositions comprising any solid or liquid physical form of one or more of the T2DBMARKERS of the invention. For example, the T2DBMARKERS can be in a crystalline form, in amorphous form, and have any particle size. The T2DBMARKER particles may be micronized, or may be agglomerated, particulate granules, powders, oils, oily suspensions or any other form of solid or liquid physical form.

For oral administration, the pharmaceutical compositions can be liquid or solid. Suitable solid oral formulations include tablets, capsules, pills, granules, pellets, and the like. Suitable liquid oral formulations include solutions, suspensions, dispersions, emulsions, oils, and the like.

Any inert excipient that is commonly used as a carrier or diluent may be used in the formulations of the present invention, such as for example, a gum, a starch, a sugar, a cellulosic material, an acrylate, or mixtures thereof. The compositions may further comprise a disintegrating agent and a lubricant, and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

T2DBMARKERS can be administered as active ingredients in admixture with suitable pharmaceutical diluents, excipients or carriers (collectively referred to herein as "carrier" or "diluent" materials or "pharmaceutically acceptable carriers or diluents") suitably selected with respect to the intended form of administration. As used herein, "pharmaceutically acceptable carrier or diluent" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions, or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) comprised of neutral lipids, anionic lipids, cationic lipids, or mixtures thereof can also be used as pharmaceutically acceptable carriers. These can be prepared according to methods known to those skilled in the art, for example, as described in U.S. Pat. No. 4,522,811.

It is especially advantageous to formulate oral and intravenous compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration. A pharmaceutical composition typically contains an amount of at least 0.1 weight % of active ingredient, i.e., a peptide inhibitor or antibody of this invention, per weight of total pharmaceutical composition. A weight % is a ratio by weight of active ingredient to total composition. Thus, for example, 0.1 weight % is 0.1 grams of peptide inhibitor per 100 grams of total composition.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic, or oily solutions and the like as detailed above.

For intravenous administration, Glucuronic acid, L-lactic acid, acetic acid, citric acid or any pharmaceutically acceptable acid/conjugate base with reasonable buffering capacity in the pH range acceptable for intravenous administration can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12.

Subcutaneous formulations can be prepared according to procedures well known in the art at a pH in the range between about 5 and about 12, which include suitable buffers and isotonicity agents. They can be formulated to deliver a daily dose of the active agent in one or more daily subcutaneous administrations. The choice of appropriate buffer and pH of a formulation, depending on solubility of one or more T2DBMARKERS to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12.

The compositions of the present invention can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

"Co-administration" as used herein means administration of a pharmaceutical composition according to the invention in combination with a second therapeutic agent. The second therapeutic agent can be any therapeutic agent useful for treatment of the patient's condition. For example, inhibition of kinases with a diabetes-modulating drug as a second therapeutic agent used in conjunction with the peptide inhibitors of the present invention is contemplated. Additionally, for example, a first therapeutic agent can be a peptide inhibitor of the invention and a second therapeutic agent can be an antisense or ribozyme molecule against one or more kinases that, when administered in a viral or nonviral vector, will facilitate a transcriptional inhibition of that kinase and which will complement the inhibitory activity of the small molecule. Co-administration may be simultaneous, for example, by administering a mixture of the therapeutic agents, or may be accomplished by administration of the agents separately, such as within a short time period. Co-administration also includes successive administration of a peptide inhibitor of the invention and one or more of another therapeutic agent. The second therapeutic agent or agents may be administered before or after the peptide inhibitor. The second therapeutic agent may also be an inhibitor of kinases implicated in Diabetes or pre-diabetic conditions, which has particular advantages when administered with the first inhibitor. Dosage treatment may be a single dosing schedule or a multiple dosing schedule.

A therapeutic agent may be a drug, a chemotherapeutic agent, a radioisotope, a pro-apoptosis agent, an anti-angiogenic agent, a hormone, a cytokine, a cytotoxic agent, a cytocidal agent, a cytostatic agent, a peptide, a protein, an antibiotic, an antibody, a Fab fragment of an antibody, a hormone antagonist, a nucleic acid or an antigen. The anti-angiogenic agent is selected from the group consisting of thrombospondin, angiostatin 5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CMI 101, Marimastat, pentosan polysuiphate, angiopoietin 2 (Regeneron), interferon-alpha, herbimycin A, PNU 14515 6E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline. Whereas, the pro-apoptosis agent is selected from the group consisting of etoposide, ceramide sphingomyelin, Bax, Bid, Bik, Bad, caspase-3, caspase-8, caspase-9, fas, fas ligand, fadd, fap-1, tradd, faf, rip, reaper, apoptin, interleukin-2 converting enzyme or annexin V. Additional apoptotic agents include gramicidin, magainin, mellitin, defensin, or cecropin. Furthermore, a cytokine may be selected from the group consisting of interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor).

Examples of such therapeutics or agents frequently used in Diabetes treatments, and may modulate the symptoms or risk factors of Diabetes include, but are not limited to, sulfonylureas like glimepiride, glyburide (also known in the art as glibenclamide), glipizide, gliclazide; biguanides such as metformin; insulin (including inhaled formulations such as Exubera), and insulin analogs such as insulin lispro (Humalog), insulin glargine (Lantus), insulin detemir, and insulin glulisine; peroxisome proliferator-activated receptor-γ (PPAR-γ) agonists such as the thiazolidinediones including troglitazone (Rezulin), pioglitazone (Actos), rosiglitazone (Avandia), and isaglitzone (also known as netoglitazone); dual-acting PPAR agonists such as BMS-298585 and tesaglitazar; insulin secretagogues including metglitinides such as repaglinide and nateglinide; analogs of glucagon-like peptide-1 (GLP-1) such as exenatide (AC-2993) and liraglutide (insulinotropin); inhibitors of dipeptidyl peptidase IV like LAF-237; pancreatic lipase inhibitors such as orlistat; α-glucosidase inhibitors such as acarbose, miglitol, and voglibose; and combinations thereof, particularly metformin and glyburide (Glucovance), metformin and rosiglitazone (Avandamet), and metformin and glipizide (Metaglip). Such therapeutics or agents have been prescribed for subjects diagnosed with Diabetes, one or more complications related to Diabetes, or a pre-diabetic condition, and may modulate the symptoms or risk factors of Diabetes, one or more complications related to Diabetes, or a pre-diabetic condition (herein, "diabetes-modulating agents").

The precise effective amount or therapeutically effective amount of pharmaceutical compositions (including pharmaceutical compositions comprising the peptide inhibitors disclosed herein) applied or administered to humans can be determined by the ordinarily-skilled artisan with consideration of individual differences in age, weight, extent of cellular infiltration by inflammatory cells and condition of the patient. The pharmaceutical preparation of the invention should be administered to provide an effective concentration of 5-100 μM, preferably about 5 μM.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject. The total effective amount of a peptide inhibitor of the invention can be administered to a subject as a single dose, either as a bolus or by infusion over a relatively short period of time, or can be administered using a fractionated treatment protocol, in which the multiple doses are administered over a more prolonged period of time.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 μg/kg/body weight, about 5 μg/kg/body weight, about 10 μg/kg/body weight, about 50 μg/kg/body weight, about 100 μg/kg/body weight, about 200 μg/kg/body weight, about 350 μg/kg/body weight, about 500 μg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, can be administered, based on the numbers described above.

The peptide inhibitors of the invention can be used to treat a biological condition mediated by serpin activity. The biological condition mediated by serpin activity includes type 2 Diabetes Mellitus, also known in the art as non-insulin dependent Diabetes mellitus. The biological condition further includes abnormal bleeding, thrombosis and other coagulation disorders (such as, for example, thrombocytopenia), defects in hemostasis and fibrinolysis, inflammation and angiogenesis, cardiovascular disease (such as, without limitation, atherosclerosis, atherothrombosis, coronary artery disease, myocardial infarction), among others.

Potentiation of insulin signaling in vivo, which may result from administration of the pharmaceutical compositions comprising one or more peptide inhibitors of the invention, can be monitored as a clinical endpoint. In principle, a way to look at insulin potentiation in a patient is to perform an oral glucose tolerance test. After fasting, glucose is given to a patient and the rate of the disappearance of glucose from blood circulation (namely glucose uptake by cells) is measured by assays well known in the art. Slow rate (as compared to healthy subject) of glucose clearance will indicate insulin resistance. The administration of pharmaceutical compositions comprising one or more T2DBMARKERS, such as the peptide inhibitors of the invention, to an insulin-resistant subject increases the rate of glucose uptake as compared to a non-treated subject. Peptide inhibitors may be administered to an insulin resistant subject for a longer period of time, and the levels of insulin, glucose, and leptin in blood circulation (which are usually high) may be determined. Decrease in glucose levels will indicate that the peptide inhibitor potentiated insulin action. A decrease in insulin and leptin levels alone may not necessarily indicate potentiation of insulin action, but rather will indicate improvement of the disease condition by other mechanisms.

The peptide inhibitors of the invention can be used to therapeutically treat Diabetes or a pre-diabetic condition in a patient with type 2 Diabetes or a pre-diabetic condition as defined herein. A therapeutically effective amount of the inhibitor can be administered to the patient, and clinical markers, for example blood sugar level and/or IRS-1 phosphorylation, can be monitored. The peptide inhibitors of the invention can further be used to prevent type 2 Diabetes or a pre-diabetic condition in a subject.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

EXAMPLES

Example 1

Biomarker Identification in the Cohen Rat Model of Type 2 Diabetes

The Cohen diabetic (CD) rat is a well-known and versatile animal model of Type 2 Diabetes, and is comprised of 2 rodent strains that manifest many of the common features of Type 2 Diabetes (T2D) in humans. The sensitive strain (CDs) develops Diabetes within 30 days when maintained on a high sucrose/copper-poor diet (HSD), whereas the resistant strain (CDr) retains normal blood glucose levels. When maintained indefinitely on regular rodent diet (RD), neither strain develop symptoms of T2D.
Sample Preparation Serum, urine, and tissue samples (including splenic tissue, pancreatic tissue, and liver tissue) were obtained from both CDr and CDs rats that were fed either RD or HSD for 30 days. The samples were flash-frozen and stored at −80° C.

Whole protein extracts were prepared for each of the 4 experimental conditions, utilizing 10 individual organs per group. Pancreatic tissues were processing using a mechanical shearing device (Polytron). To preserve protein integrity in processed samples, tissues were kept on dry ice until processing commenced and all buffers and equipment were pre-chilled. Samples were also kept on ice during the homogenization process.

T-Per buffer (Pierce) was pre-chilled on ice and two tablets of Complete Protease Inhibitor (Roche Applied Sciences) were added per 50 ml of buffer prior to use. Once protease inhibitors were added, any unused buffer was discarded. T-Per buffer was used at 20 nil per gram of tissue. For each group, pancreatic samples were weighed and the amount of lysis buffer required was calculated and added to each tissue sample in a 50 nil tube. Each sample was homogenized on ice for 10 seconds, followed by a 30 second rest period to allow the sample to cool. If gross debris was still apparent, the cycle was repeated until the homogenate was smooth. The homogenization probe was inserted into the samples approximately 1 cm from the bottom of the tube to minimize foaming. When homogenization was complete, the extract was centrifuged at 10,000×g for 15 minutes at 4° C.

Following centrifugation, the supernatant was harvested and a bicinchoninic acid (BCA) assay was performed to determine the total protein content. Table 2 provides the mean protein content of the samples corresponding to CDr rats fed either RD or HSD, and CDs rats fed either RD or HSD.

TABLE 2

| Total Protein Content of Pancreatic Extracts from Cohen Diabetic Rats | | | | |
|---|---|---|---|---|
| | Mean Protein Content (µg/ml) | | | |
| Tissue | CDr-RD | CDr-HSD | CDs-RD | CDs-HSD |
| Pancreas | 7969.2 | 6061.9 | 6876.4 | 3387.8 |

Supernatants were dispensed into aliquots and stored at −80° C. Pelleted material was also kept and stored at −80° C.

Protein expression profiling of the CDr and CDs phenotypes was conducted on the pancreatic extracts using one-dimensional SDS-PAGE. A sample of each extract containing 6 µg of total protein was prepared in sample buffer and loaded onto a 4-12% acrylamide gel. Following completion of the electrophoretic run, the gel was soaked with Coomassie stain for 1 hour and destained in distilled water overnight. The resulting protein expression profile allowed an empirical visual comparison of each extract. These pancreatic extracts were then used for bi-directional immunological contrasting, disclosed herein.

Since albumin, immunoglobulin and other abundant proteins constitute about 95-97% of the total proteins in serum, the detection of less abundant proteins and peptides markers are masked if the whole serum were analyzed directly. Therefore, fractionation of serum samples was necessary to reduce masking of low abundance protein and to increase the number of peaks available for analysis.

To increase the detection of a larger number of peaks as well as to alleviate signal suppression effects on low abundance proteins from high abundant proteins such as albumin, immunoglobulin etc., the crude serum samples from CDr and CDs rats fed RD or HSD were fractionated into six fractions. The fractionation was carried out using anion exchange bead based serum fractionate kit purchased from Ciphergen (Fremont, Calif.). In brief, the serum samples were diluted with a 9M urea denaturant solution; the diluted samples were then loaded onto a 96-well filter microplate pre-filled with an anion exchange sorbent. Using this process, samples were allowed to bind to the active surface of the beads, and after 30 minutes incubation at 4° C., the samples were eluted using stepwise pH gradient buffers. The process allowed the collection of 6 fractions including pH 9, pH 7, pH 5, pH 4, pH 3 and an organic eluent. After the fractionation, the serum samples were analyzed in the following formats on SELDI chips.

SELDI (Surface Enhanced Laser Desorption Ionization)

SELDI Proteinchip® Technology (Ciphergen) is designed to perform mass spectrometric analysis of protein mixtures retained on chromatographic chip surfaces. The SELDI mass spectrometer produces spectra of complex protein mixtures based on the mass/charge ratio of the proteins in the mixture and their binding affinity to the chip surface. Differentially expressed proteins are determined from these protein profiles by comparing peak intensity. This technique utilizes aluminum-based supports, or chips, engineered with chemical modified surfaces (hydrophilic, hydrophobic, pre-activated, normal-phase, immobilized metal affinity, cationic or anionic), or biological (antibody, antigen binding fragments (e.g., scFv), DNA, enzyme, or receptor) bait surfaces. These varied chemical and biochemical surfaces allow differential capture of proteins based on the intrinsic properties of the proteins themselves. Tissue extractions or body fluids in volumes as small as 1 µl are directly applied to these surfaces, where proteins with affinities to the bait surface will bind. Following a series of washes to remove non-specifically or weakly bound proteins, the bound proteins are laser desorbed and ionized for MS analysis. Molecular weights of proteins ranging from small peptides to proteins (1000 Dalton to 200 kD) are measured. These mass spectral patterns are then used to differentiate one sample from another, and identify lead candidate markers for further analysis. Candidate marker have been identified by comparing the protein profiles of conditioned versus conditioned stem cell culture medium. Once candidate markers are identified, they are purified and sequenced.

The fractionated serum samples were applied to different chemically modified surface chips (cationic exchange, anionic exchange, metal-affinity binding, hydrophobic and normal phase) and profiled by SELDI, two-dimensional PAGE (2DE) and two-dimensional liquid chromatography (2D/LC).

Two-Dimensional Liquid Chromatography (2D/LC)

The ProteomeLab PF 2D Protein Fractionation System is a fully automated, two-dimensional fractionation system (in liquid phase) that resolves and collects proteins by isoelectric point (pI) in the first dimension and by hydrophobicity in the second dimension. The system visualizes the complex pattern with a two dimensional protein map that allows the direct comparison of protein profiling between different samples. Since all components are isolated and collected in liquid phase, it is ideal for downstream protein identification using mass spectrometry and/or protein extraction for antibody production.

The PF 2D system addresses many of the problems associated with traditional proteomics research, such as detection of low abundance proteins, run-to-run reproducibility, quantitation, detection of membrane or hydrophobic proteins, detection of basic proteins and detection of very low and very high molecular weight proteins. Since the dynamic range of proteins in serum spans over 10 orders of magnitude, and the relatively few abundant proteins make up over 95% of the total protein contents, this makes it very difficult to detect low abundant proteins that are candidate markers. In order to enrich and identify the less abundant proteins, the serum samples were partitioned using IgY-R7 rodent optimized partition column to separate the seven abundant proteins (Albumin, IgG, Transferrin, Fibrinogen, IgM, α1-Antitrypsin, Haptoglobin) from the less abundant ones.

The partitioned serum was applied to the PF-2D. The first dimensional chromatofocusing was performed on an HPCF column with a linear pH gradient generated using start buffer (pH 8.5) and eluent buffer (pH 4.0). The proteins were separated based on the pI. Fractions were collected and applied to a reverse-phase HPRP column for a second dimensional separation. The 2D map generated from each sample was then compared and differential peak patterns were identified. The fraction was subsequently selected and subjected to trypsin digestion. The digested samples were sequenced using LC/MS for protein identification.

2-D Gel Electrophoresis

Two-dimensional electrophoresis has the ability to resolve complex mixtures of thousands of proteins simultaneously in a single gel. In the first dimension, proteins are separated by pI, while in the second dimension, proteins are separated by MW. Applications of 2D gel electrophoresis include proteome analysis, cell differentiation, detection of disease markers, monitoring response to treatment etc.

The IgY partitioned serum samples were applied to immobilized pH gradient (IPG) strips with different pH gradients, pH 3-10, pH 3-6 and pH 5-8. After the first dimensional run, the IPG strip was laid on top of an 8-16% or 4-20% SDS-PAGE gradient gel for second dimensional separation.

Results

Figure 2:
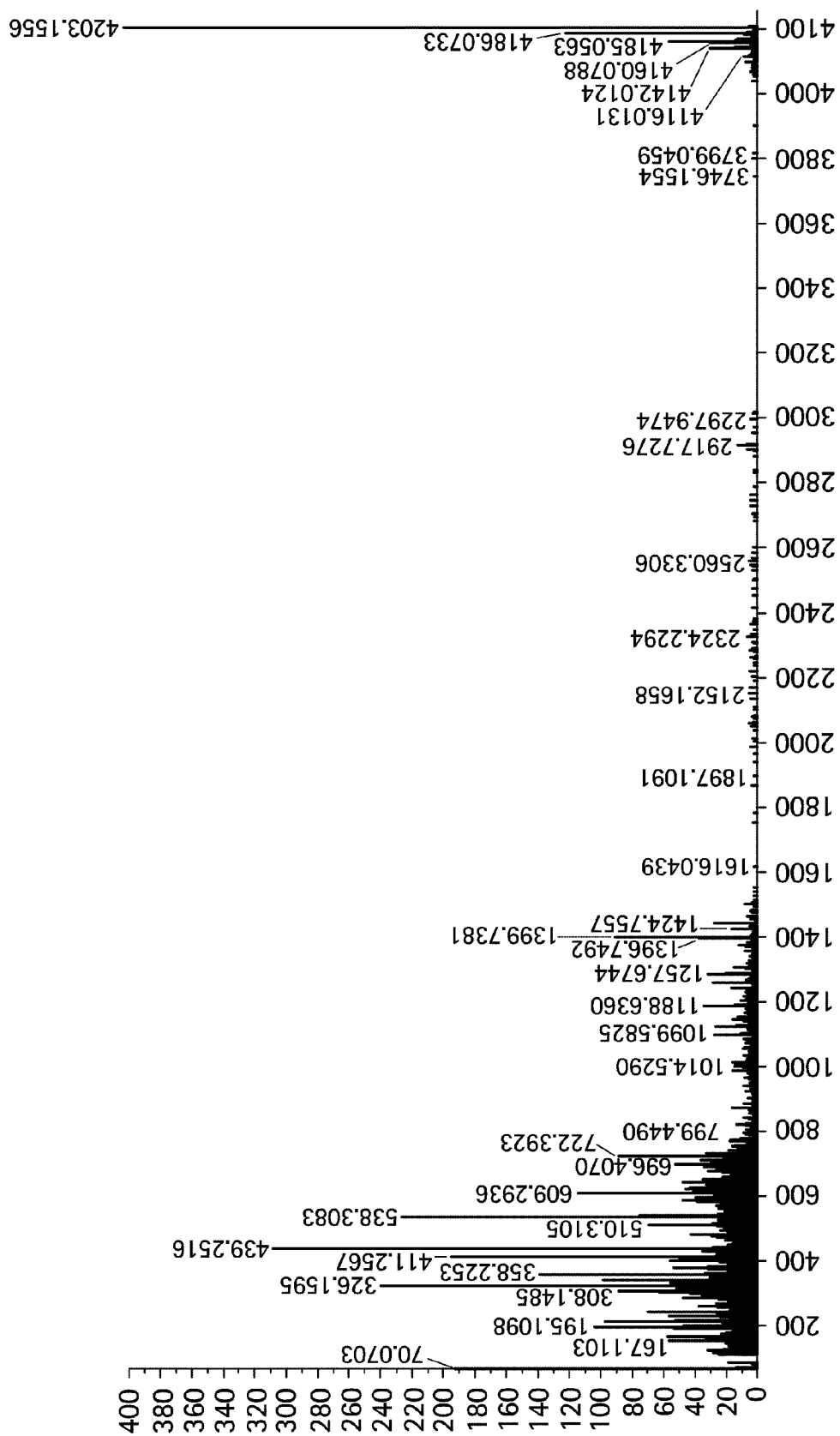
FIG. 2 is an MS/MS spectrum of the 4.2 kilodalton fragment identified by SELDI.

A peak protein of approximately 4200 daltons was present in the serum of CDr-RD and CDr-HSD, but not in the serum of CDs-RD or CDs-HSD, as shown in FIG. 1. FIG. 2 is a MS/MS spectrum of the 4200 dalton fragment. This protein was sequenced and following extensive database searches, was found to be a novel protein. The peptide was designed "D3" and its sequence was found to be SGRPP MIVWF NRPFL IAVSH THGQT ILFMA KVINP VGA (SEQ ID NO: 1). The D3 peptide is a 38-mer peptide sequence that corresponds to the first biomarker discovered in the Cohen diabetic rat. Sequence alignment using the BLAST algorithm available from the National Center for Biotechnology Information (NCBI) was performed and the 38-amino acid fragment was found to have sequence identity with at least ten different amino acid sequences. Notably, BLAST alignment revealed that the 38-amino acid D3 peptide contains conserved motifs corresponding to: "FNRPFL" (SEQ ID NO: 6) and "FMS/GKVT/VNP" (SEQ ID NO: 7). FIG. 3A shows the results of the BLAST alignment of amino acid sequences related to the D3 peptide fragment, and FIG. 3B shows the results of a BLAST alignment of nucleic acid sequences encoding the D3 peptide and the peptides identified by protein BLAST. Degenerate primers were designed to target the conserved motifs and comprise the following sequences: Forward primer (targeting regions containing the amino acid sequence "FNRPFL" (SEQ ID NO: 6): 5'-TTC AAC MRR CCY TTY ST-3' (SEQ ID NO: 4) and Reverse primer (targeting regions containing the sequence "FMS/GKVT/VNP" (SEQ ID NO: 7)): 5'-YVA CYT TKC YMA KRA AGA-3' (SEQ ID NO: 5); wherein M=A or C; R=A or G; Y=C or T; S=C or G; K=G or T; and V=A, C, or G. These degenerate primers were used in reverse-transcription polymerase chain reactions (RT-PCR) to amplify human SERPINA 3 in liver and pancreas. A 1.3 Kb fragment was identified in human liver and pancreas.

Table 3 below represents additional identified candidate markers identified by SELDI analysis.

| Array Type Sample M/Z | CM10 (Anion exchange) CDr-RD | CDs-RD | CDr-HSD | CDs-HSD |
|---|---|---|---|---|
| Fractioned Serum F1 | | | | |
| ~2156 | + | + | − | − |
| ~2270 | + | + | − | + |
| ~3875 | + | − | + | − |
| Fractioned Serum F3 | | | | |
| ~3408 | − | + | − | + |
| ~3422 | + | − | + | − |
| ~3848 | − | + | − | + |
| ~3861 | + | − | + | − |
| Fractioned Serum F4 | | | | |
| ~4202 | + | − | + | − |
| ~4423 | + | − | + | − |
| Fractioned Serum F5 | | | | |
| ~5377 | ++ | ++ | ++ | + |
| ~5790 | +/− | +/− | − | + |
| ~8813 | +/− | +/− | +/− | + |
| Fractioned Serum F6 | | | | |
| ~4200 | + | − | + | − |
| Whole Serum | | | | |
| ~6631 | − | + | − | − |
| ~7013 | − | − | + | + |
| ~7027 | + | + | − | − |
| ~7811 | − | + | − | − |

| Array Type Sample M/Z | Q10 CDr-RD | CDs-RD | CDr-HSD | CDs-HSD |
|---|---|---|---|---|
| Fractioned Serum F1 | | | | |
| ~2627 | + | − | + | − |
| ~2705 | + | − | + | − |
| ~4290 | + | + | ++ | + |
| ~5058 | − | − | + | − |
| ~5220 | + | ++ | + | + |
| ~5789 | − | − | + | − |
| ~8818 | + | +/− | ++ | ++ |
| Fractioned Serum F2 | | | | |
| ~2359 | + | +/− | − | − |
| ~2587 | + | + | − | +/− |
| ~2879 | + | + | − | +/− |
| ~2298 | − | + | − | − |
| Fractioned Serum F4 | | | | |
| ~4200 | + | − | + | − |
| ~2067 | − | − | + | + |
| ~2092 | − | − | + | + |
| ~2042 | − | − | + | + |
| ~8810 | − | − | + | + |
| ~8850 | + | + | − | − |
| Fractioned Serum F5 | | | | |
| ~3977 | + | − | + | − |
| ~4200 | + | − | + | − |
| ~2102 | + | − | + | − |
| ~4030 | + | ++ | + | ++ |
| Fractioned Serum F6 | | | | |
| ~4200 | + | − | + | − |
| ~17645 | + | − | + | − |
| Whole Serum | | | | |
| ~6632 | − | + | − | − |
| ~3419 | + | + | − | − |
| ~3435 | + | + | − | − |
| ~4074 | + | + | − | − |
| ~4090 | + | + | − | − |
| ~4200 | + | − | + | − |
| ~5152 | + | + | − | − |
| ~8915 | + | + | − | − |

| Array Type Sample M/Z | H50 CDr-RD | CDs-RD | CDr-HSD | CDs-HSD |
|---|---|---|---|---|
| Fractioned Serum F2 | | | | |
| ~5521 | − | + | − | − |
| Fractioned Serum F5 | | | | |
| ~34224 | − | − | − | + |

| Array Type Sample M/Z | IMAC CDr-RD | CDs-RD | CDr-HSD | CDs-HSD |
|---|---|---|---|---|
| Whole Serum | | | | |
| ~2714 | + | + | − | + |
| ~4330 | − | + | + | + |

Figure 4B:
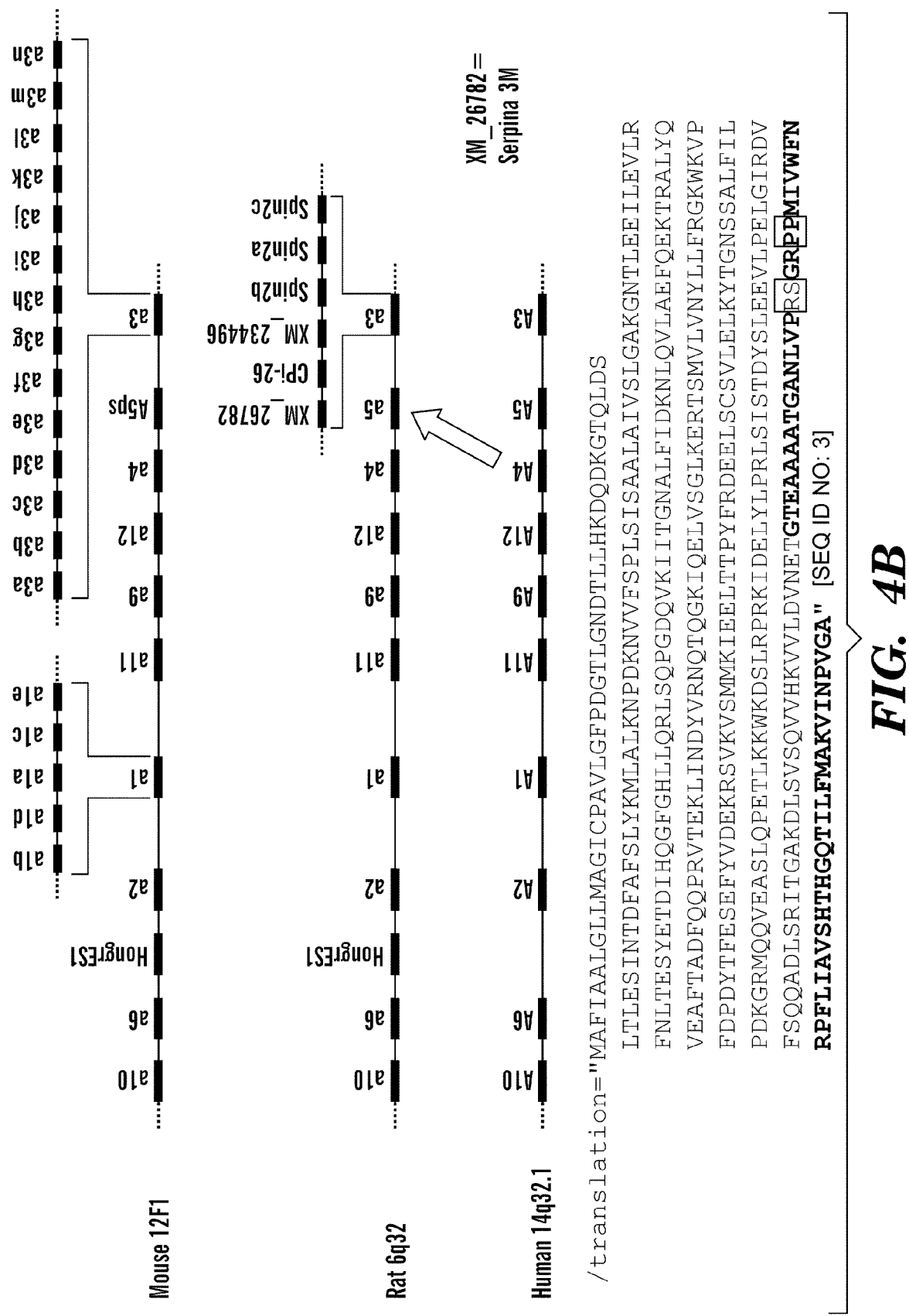
FIG. 4B shows the critical amino acid positions that may define the mechanism of action of the D3 peptide (SEQ ID NO: 3) and its inhibitory activity.
Figure 5:
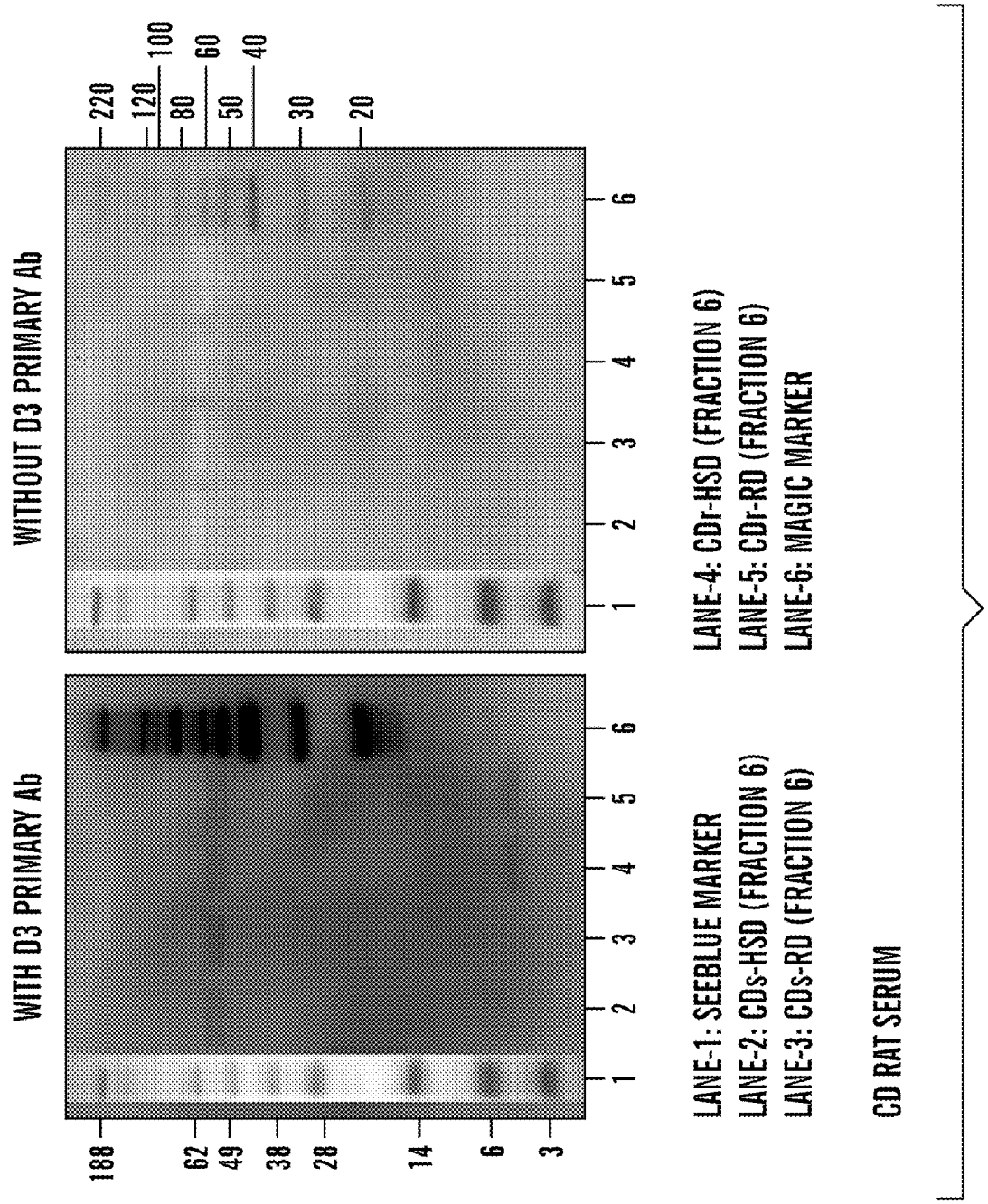
FIG. 5 is a photograph of Western blots depicting the reactivity of the D3-hyperimmune rabbit serum with the ~4 kD protein fragment present in CDr-RD and CDr-HSD rat serum. In the left photograph, a higher molecular weight doublet (in the range of 49 and 62 kD) also reacted with the hyperimmune sera, indicating that a parent protein (and a protein complex) is expressed by all strains under both RD and HSD treatment modalities, while the derivative of smaller size is differentially expressed only in the CDr strain. As a negative control, the right photograph shows a Western blot membrane incubated in the absence of the D3 hyperimmune rabbit serum.

The D3 peptide was used for the production of hyper-immune serum in rabbits. FIGS. 4A and 4B provide bioinformatic and sequence analysis of the D3 sequence. The D3 peptide was found to be homologous to *Rattus norvegicus* Serpin 3M. FIG. 5 depicts Western blots showing the reactivity of the D3 hyper-immune serum with a ~4 kD protein isolated from CDr-RD and CDr-HSD rat serum fraction 6. Fractionated CD rat serum samples were run on a 10% SDS-PAGE gel, then transferred to PVDF membranes. A higher molecular weight doublet (in the range of 49 and 62 kD) also reacted with the hyper-immune sera, indicated that a parent protein is expressed by all strains under treatment modalities RD or HSD, however a derivative of smaller size (~4 kD) corresponding to the D3 fragment is differentially expressed only in the CDr strain. These results are consistent with the results obtained by SELDI profiling. The concentration of the D3 fragment in CDr rat serum was subsequently analyzed by SELDI. A series of synthetic D3 peptide standards (0.1, 0.033, 0.011, 0.0037, 0.0012 and 0 mg/ml) and 10× diluted CDr-serum were spotted in duplicate on Q10 protein chip arrays. The peak intensity was plotted against the concentration of D3 peptide standards. Based on the plot, the linear range for concentration determination is from 0 to 0.01 mg/ml. Accordingly, the concentration of D3 in CDr-RD serum is around 0.04 mg/ml, based on the peak intensity of the CDr-RD serum sample.

Analysis of Serpina expression by Western blot analysis was performed in Cohen rat liver extracts using anti D3 rabbit serum (1:200) and secondary goat anti-rabbit IgG conjugated to HRP (1:25,000 dilution). Controls containing liver extracts (10 μg) and secondary goat anti-rabbit IgG antibodies conjugated to HRP (1:25,000 dilution), but no primary antibody were also analyzed. A cluster of proteins (41, 45 and 47 kD) were visualized following reaction of liver extracts with D3 hyper immune serum. The 41 and 45 kD proteins were expressed at approximately the same level while the 47 kD protein is not detected in the diabetic rat—i.e., CDs-HSD (diabetic).

Table 4 contains a summary of biomarker data obtained from CD rat serum samples.

TABLE 4

| | | | | | Differential profiling in Cohen Diabetic Rats Serum | |
|---|---|---|---|---|---|---|
| No. | Protein | Gene | Gi | MW (KD) | Calculated pI | CDr-RD | CDs-RD |
| 1 | C-terminal fragment of a predicted protein, similar to serine protease inhibitor 2.4 | Serpina 3M | 34867677 | 4.2 | 12.01 | + | − |
| 2 | unnamed protein product or Spin2a protein | Spin 2a | 57231 | 45 | 5.48 | + | − |
| | | | 56789860 | 46 | 5.48 | | |
| 3 | Fetuin beta or Fetub protein | Fetub | 17865327 | 42 | 6.71 | + | − |
| | | | 47682636 | 44 | 7.47 | − | + |
| 4 | Apolipoprotein C-III precursor | Apoc 3 | 91990 | 11 | 4.65 | + | + |
| 5 | Predicted protein, similar to Apolipoprotein C2 | Apoc 2 predicted | 27676424 | 11 | 4.57 | + | + |
| 6 | Aa2-066 or alpha-2-HS-glycoprotein or alpha-2-HS-glycoprotein | None Ahsg | 33086518 6978477 60552688 | 61 39 39 | 4.39 6.05 6.05 | + | − |
| 7 | T-kininogen II precursor | None | 57526868 | 49 | 5.94 | − | + |
| 8 | alpha-1-macroglobulin or pregnancy-zone protein | Pzp Pzp | 202857 21955142 | 168 | 6.46 | TBD + | + − |
| 9 | Serine/cysteine proteinase inhibitor, clade C, member 1 (predicted) | Serpinc1 | 56789738 | 53 | 6.18 | + | − |
| 10 | coagulation factor 2 | F2 | 12621076 | 72 | 6.28 | + | − |
| 11 | inter-alpha-inhibitor H4 heavy chain | ITIH4 | 9506819 59808074 | 104 | 6.08 | + + | − − |
| 12 | vitamin D binding protein prepeptide | Gc | 203927 | 55 | 5.65 | + | − |
| 13 | LMW T-kininogen I precursor or kininogen or major acute phase alpha-1 protein precursor | Map1 | 205085 56270334 68791 | 49 | 6.29 | + | ++ |
| 14 | preapolipoprotein A-1 or apolipoprotein A-1 | ApoA1 | 55747 59808388 | 30 | 5.52 | + + | + + |
| 15 | predicted protein, similar to apolipoprotein C-II precursor | Apoc2 | 109461385 | 11 | 4.57 | TBD | TBD |
| 16 | thrombin or prothrombin precursor | | 207304 56970 | 28 72 | 9.38 | TBD TBD | TBD TBD |
| 17 | Apolipoprotein E or Apolipoprotein E or Apolipoprotein E or ORF2 | ApoE | 37805241 55824759 20301954 202959 | 36 36 36 38 | 5.23 5.53 | + + + + | − − − ++ |
| 18 | Liver regeneration-related protein LRRG03 | Tf | 33187764 | 78 | 7.14 | + | + |
| 19 | Apolipoprotein A-IV | Apoa4 | 60552712 | 44 | 5.12 | + | − |
| 20 | LOC297568 protein or Alpha-1-inhibitor 3 precursor | | 71051724 112893 | 79 165 | 5.45 | + + | ++ ++ |
| 21 | hypothetical protein XP_579384 | | 62718654 | 188 | 6.06 | + | ++ |
| 22 | Histidine-rich glycoprotein | Hrg | 11066005 | 59 | 8.12 | + | ++ |
| 23 | unnamed protein product or predicted: hypothetical protein XP_579477 | None | 55562 62647940 | 167 167 | 5.68 | +++ +++ | ++ ++ |
| 24 | Complement component C9 precursor | C9 | 2499467 | 63 | 5.51 | +++ | ++ |
| 25 | Apolipoprotein H | ApoH | 57528174 | 40 | 8.58 | − | + |
| 26 | B-factor, properdin | Cfb | 56268879 | 86 | 6.57 | − | + |
| 27 | Hemopexin | Hpx | 16758014 | 52 | 7.58 | + | ++ |

TABLE 4-continued

T2DBMARKER Data Summary

| No. | Protein | Differential profiling in Cohen Diabetic Rats Serum | | Profiling technology | Human Homologues |
|---|---|---|---|---|---|
| | | CDr-HSD | CDs-HSD | | |
| 1 | C-terminal fragment of a predicted protein, similar to serine protease inhibitor 2.4 | + | − | SELDI | Serpina 3 |
| 2 | unnamed protein product or Spin2a protein | − | − | PF-2D | |
| 3 | Fetuin beta or Fetub protein | − | TBD | PF-2D result | Fetub_human |
| | | − | + | 2DE result | |
| 4 | Apolipoprotein C-III precursor | + | TBD | PF-2D | Apoc3_human |
| 5 | Predicted protein, similar to Apolipoprotein C2 | + | − | PF-2D | Apoc2_human |
| 6 | Aa2-066 | + | + | PF-2D | Alpha-2-HS-glycoprotein FetuA_Human |
| | or alpha-2-HS-glycoprotein or alpha-2-HS-glycoprotein | | | | |
| 7 | T-kininogen II precursor | − | TBD | PF-2D | |
| 8 | alpha-1-macroglobulin or pregnancy-zone protein | TBD − | TBD − | PF-2D result 2DE result | PZP_human and A2MG_human |
| 9 | Serine/cysteine proteinase inhibitor, clade C, member 1 (predicted) | + | − | PF-2D | |
| 10 | coagulation factor 2 | TBD | TBD | PF-2D | |
| 11 | inter-alpha-inhibitor H4 heavy chain | + + | TBD TBD | PF-2D | ITIH4_human |
| 12 | vitamin D binding protein prepeptide | TBD | TBD | PF-2D | VTDB_human |
| 13 | LMW T-kininogen I precursor or kininogen or major acute phase alpha-1 protein precursor | + | ++++ | PF-2D/2DE | |
| 14 | preapolipoprotein A-1 or apolipoprotein A-1 | + + | − − | PF-2D | ApoA1_human |
| 15 | predicted protein, similar to apolipoprotein C-II precursor | + | − | PF-2D | |
| 16 | thrombin or prothrombin precursor | + + | TBD TBD | PF-2D | THRB_human |
| 17 | Apolipoprotein E or Apolipoprotein E or Apolipoprotein E or ORF2 | − − − + | − − − ++ | 2DE | |
| 18 | Liver regeneration-related protein LRRG03 | ++++ | ++ | 2DE | |
| 19 | Apolipoprotein A-IV | − | − | 2DE | |
| 20 | LOC297568 protein or Alpha-1-inhibitor 3 precursor | + + | +++++ +++++ | 2DE | |
| 21 | hypothetical protein XP_579384 | + | +++ | 2DE | |
| 22 | Histidine-rich glycoprotein | + | +++ | 2DE | |
| 23 | unnamed protein product or predicted: hypothetical protein XP_579477 | ++ ++ | + + | 2DE 2DE | |
| 24 | Complement component C9 precursor | ++ | + | PF/2DE | |
| 25 | Apolipoprotein H | + | + | 2DE | |
| 26 | B-factor, properdin | + | + | 2DE | |
| 27 | Hemopexin | + | +++ | 2DE | Hemo_human |

Example 2

Bi-Directional Immunological Contrasting and Generation of Monoclonal Antibodies From the pancreatic extract protein profiles obtained by SDS-PAGE, obvious differences in the banding patterns were noted between CDr-HSD and CDs-HSD samples. Bi-directional immunological contrast was performed between these two samples. This technique involves injecting two pancreatic extracts from the Cohen diabetic rats to be contrasted separately into the footpads of an experimental animal (e.g. a Balb/c mouse). Following uptake and processing of the antigen at the site of injection by antigen presenting cells (APCs), the activated APCs migrate to the local lymph nodes (popliteal) to initiate an immune response. As these lymph nodes are located in each leg, they are anatomically separated from each other, which prevents mixing of antigen-specific lymphocytes at this point. Later in the immune response, these activated lymphocytes migrate from the local lymph nodes to the spleen where they become mixed, and from where they may circulate systemically.

Two weeks after footpad injection, the animals were boosted by injecting each footpad with the same antigen as before. This boost recalls antigen specific lymphocytes back to the site of injection, again subsequently draining to the popliteal lymph nodes. This technique uses the natural proliferation and cell migration processes as a filtering mechanism to separate and enrich specific lymphocytes in each lymph node, where they are anatomically segregated to minimize mixing of cells that are specific for antigen(s) expressed in only one of the extracts. Three days after boosting, the popliteal lymph nodes were removed and separated into pools derived from each side of the animals. When boosting, it is imperative not to switch the antigenic material, as this will cause specific lymphocytes to migrate to both sets of popliteal lymph nodes and the anatomical segregation of specific cells, and hence the advantage of the technique, will be lost.

Fifteen female Balb/c mice ages 6-8 weeks were ordered from Harlan. Each animal was injected with 25 μg of CDr-HSD pancreatic extract into the left hind footpad, and 25 μg of CDs-HSD pancreatic extract into the right hind footpad. Antigens were prepared in 20% Ribi adjuvant in a final volume of 50 μl as follows:

TABLE 5

|  | Right footpad | Left footpad |
| --- | --- | --- |
| 375 mg of CDs-HSD | 110 μl | — |
| 375 mg of CDr-HSD | — | 62 μl |
| PBS | 490 μl | 538 μl |
| Ribi adjuvant | 150 μl | 150 μl |

Ribi adjuvant was warmed to 37° C. and reconstituted with 1 nil of sterile PBS. The bottle was vortexed for at least 1 minute to fully reconstitute the material. The correct volume of Ribi adjuvant was then added to the antigen preparation, and the mixture was again vortexed for 1 minute. Any unused formulated material was discarded, and any unused Ribi adjuvant was stored at 4° C. and used to formulate booster injections. Animals were primed on day 1 and boosted on day 14. Animals were euthanized on day 17, when popliteal lymph nodes were excised post mortem and returned to the lab for processing.

Generation of Hybridomas

Hybridoma cell lines were created essentially as described by Kohler and Milstein (1975). Lymphocytes derived from immunized animals were fused with a murine myeloma cell line (Sp2/0) by incubation with polyethylene glycol (PEG). Following fusion, cells were maintained in selective medium containing hypoxanthine, aminopterin and thymidine (HAT medium) that facilitates only the outgrowth of chimeric fused cells.

On the day before the fusion, the fusion partner (Sp2/0x Ag14 cells in dividing stage with viability above 95%) was split at $1\times10^5$ viable cells/ml, 24 hours before the fusion. On the day of the fusion, the mice were sacrificed and the lymph nodes were excised and placed in a Petri dish containing pre-warmed room temperature DMEM supplemented with 10% fetal bovine serum (FBS). Using sterile microscope slides, the lymph nodes were placed between the 2 frosty sides of the slides and crushed into a single cell suspension. The cell suspension was then transferred to a 15 ml tube and centrifuged for 1 minute at 1000 rpm. The supernatant was removed by aspiration, and the cell pellet gently resuspended in 12 ml of serum-free DMEM, after which they were subjected to another round of centrifugation for 10 minutes at 1000 rpm. The process was repeated twice more to ensure that the serum was completely removed. After washing, the cells were resuspended in 5 ml of serum-free DMEM and counted under the microscope.

The fusion partner was collected by spinning in a centrifuge for 10 minutes at 1000 rpm. The cells were washed three times in serum-free DMEM, and finally resuspended in serum-free DMEM and counted. The number of fusion partner cells were calculated based on the number of lymph node cells. For every myeloma cell (fusion partner), 2 lymph nodes cells is needed (ratio 1:2 of myeloma to lymph node cells; e.g. for $10\times10^6$ lymph node cells, $5\times10^6$ fusion partner cells are needed). The appropriate number of myeloma cells to the LN cells were added and the total volume of cells was adjusted to 25 ml using serum free DMEM, and 25 ml of 3% dextran was then added to the cells. The mixture was spun for 10 minutes at 1000 rpm, and the supernatant aspirated as much as possible from the cell pellet. Once the lid was placed onto the tube containing the cells, the bottom of the tube was gently tapped the bottom of the tube to resuspend the cells and 1 ml of pre-warmed 50% (v/v) PEG was added to the tube. The agglutinated cells were allowed to sit for 1 minute, after which 20 ml of serum free DMEM, followed by 25 ml of 20% FBS, DMEM with 25 mM Hepes was added. The tube was inverted once to mix and then centrifuged for 10 minutes at 1000 rpm. The media was aspirated and the cells were gently resuspended by tapping. HAT selection media was added such that the cell suspension was either at $0.125\times10^6$ cells/ml or $0.0625\times10^6$ cells/ml. One hundred μl of cells per well were added to a 96-well flat bottom plate and incubated at 37° C. with $CO_2$ at 8.5%. After 2 days, the cells were fed with 100 μl of fresh HAT selection media. Cells were checked for colony growth after 7 days.

Hybridoma Screening

Once visible colonies were observed in the 96 well plates, 100 μl of conditioned supernatant was harvested from each colony for screening by ELISA. Supernatants were screened for the presence of detectable levels of antigen-specific IgG against both CDr-HSD and CDs-HSD extracts. Only colonies exhibiting a positive ELISA reaction against one of the two extracts with at least a 2-fold difference were selected for expansion and further characterization.

Pancreas extract at a concentration of 25 μg/ml to be tested was diluted in carbonate bicarbonate buffer (1 capsule of carbonate-bicarbonate was dissolved in 100 ml of deionized water). Two extra wells for the positive control and two extra wells for the negative control of a 96-well plate were reserved. The plate was then covered using adhesive film and incubated at 4° C. overnight.

The plate was washed once with 200 μl of PBS/Tween. The well content was removed by flicking the plate into a sink, and then gently tapping the plate against absorbent paper to remove remaining liquid. Approximately 200 μl of washing buffer (PBS/Tween) was added and subsequently discarded as previously described. The entire plate was then blocked for 1 hour at 37° C. in 200 μl of 5% powdered milk/PBS/Tween. The plate was then washed 3 times using PBS/Tween as previously described.

The fusion culture supernatant was diluted 1:1 in 0.5% milk/PBS/Tween and each sample added to the wells (50 μl; final volume is 100 μl per well) with 50 μl of anti-actin Ab (Sigma) at 20 μg/ml to well containing 50 μl of buffer. Fifty μl of buffer was added to the negative control well. The plate was covered and incubated overnight at 4° C. The plate was washed 3 times using PBS/Tween as previously described, and anti-HRP anti-mouse IgG in 0.5% milk/PBS/Tween at 1:20000 (100 μl) was added to each well. The plate was covered and incubated at 37° C. for two hours.

After incubation with secondary antibody, the plates were washed 4 to 5 times as previously described. On the last wash, the washing buffer was left on the plate for a couple of minutes before discarding it. One hundred μl of pre-warmed room temperature TMB (VWR; stored in the dark) was added to each well while minimizing the introduction of bubbles, until the color developed (20-30 minutes). The reaction was stopped by adding 50 μl of 2M sulfuric acid. The plate was read using a spectrophotometer at 450 nm.

Thirteen clones produced monoclonal antibodies (mAbs) that met the experimental criteria outlined above, 9 against CDs-HSD and 4 against CDr-HSD. The ELISA data for these colonies is summarized in Table 6 for monospecific CDr-HSD and CDs-HSD hybridomas. Absolute absorbance values, and fold difference at OD 450 nm is shown for each colony. To verify primary screening data, some clones were retested during expansion to confirm the experimental observations from the initial screen.

The composition of each mAb was defined by determining the class of heavy and light chains, as well as the molecular weight, of each component. Isotyping was performed using the Immunopure monoclonal antibody isotyping kit I (Pierce) according to the manufacturer's instructions. The molecular weight of heavy and light chains was determined using the Experion automated electrophoresis system from Bio-Rad. The Experion system automatically performs the multiple steps of gel-based electrophoresis: separation, staining, destaining, band detection, imaging, and data analysis. The results of these analyses are shown in Table 6, which shows the physical characterization of CDr-HSD and CDs-HSD specific monoclonal antibodies. Identification of both heavy and light chains was performed using the Immunopure monoclonal antibody isotyping kit I (Pierce), and molecular weights (in kD) were determined using the Experion automated electrophoresis system (Bio-Rad).

TABLE 6

| Clone ID Accession No. | Light chain | | Heavy chain | | Whole IgG Mol. Wt. |
|---|---|---|---|---|---|
| | Sub-type | Mol. Wt. | Sub-class | Mol. Wt. | |
| P1-5-F11 (Accession No.) | kappa | — | IgG2b | — | — |
| P1-14-A2 (Accession No.) | Kappa/ lambda | — | IgG1 | — | — |
| P1-17-E4 (Accession No.) | Kappa | — | IgG1 | — | — |
| P1-18-C12 (Accession No.) | Kappa | — | IgG2b | — | — |
| P1-20-B7 (Accession No.) | Kappa | — | IgG1 | — | — |
| P1-23-F7 (Accession No.) | Kappa | — | IgG2b | — | — |
| P2-1-E8 (Accession No.) | Kappa | — | IgG1 | — | — |
| P2-10-E3 (Accession No.) | Kappa | — | IgG2a | — | — |
| P2-14-C6 (Accession No.) | Kappa | — | IgG1 | — | — |
| P2-4-H5 (Accession No.) | Kappa | — | IgG2b | — | — |
| P2-8-A3 (Accession No.) | Kappa | — | IgG2b | — | — |
| P2-10-B8 (Accession No.) | Kappa | — | IgG2b | — | — |
| P2-13-A9 (Accession No.) | kappa | — | IgG1 | — | — |

Purification of the monoclonal antibodies and immunoprecipitation were conducted using standard protocols known in the art.

Figure 6:
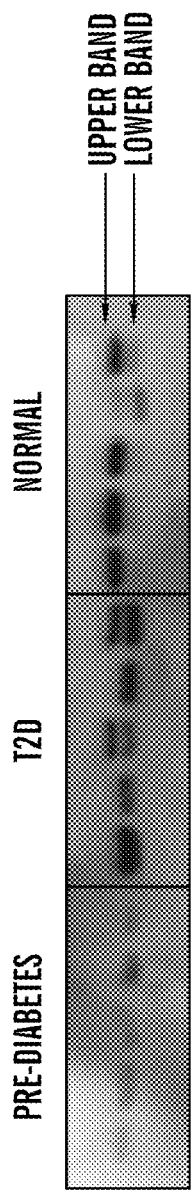
FIG. 6 depicts a Western blot of proteins identified using polyclonal anti-D3 antibodies and the relative abundance of the protein by quantification of band intensity.
Figure 7:
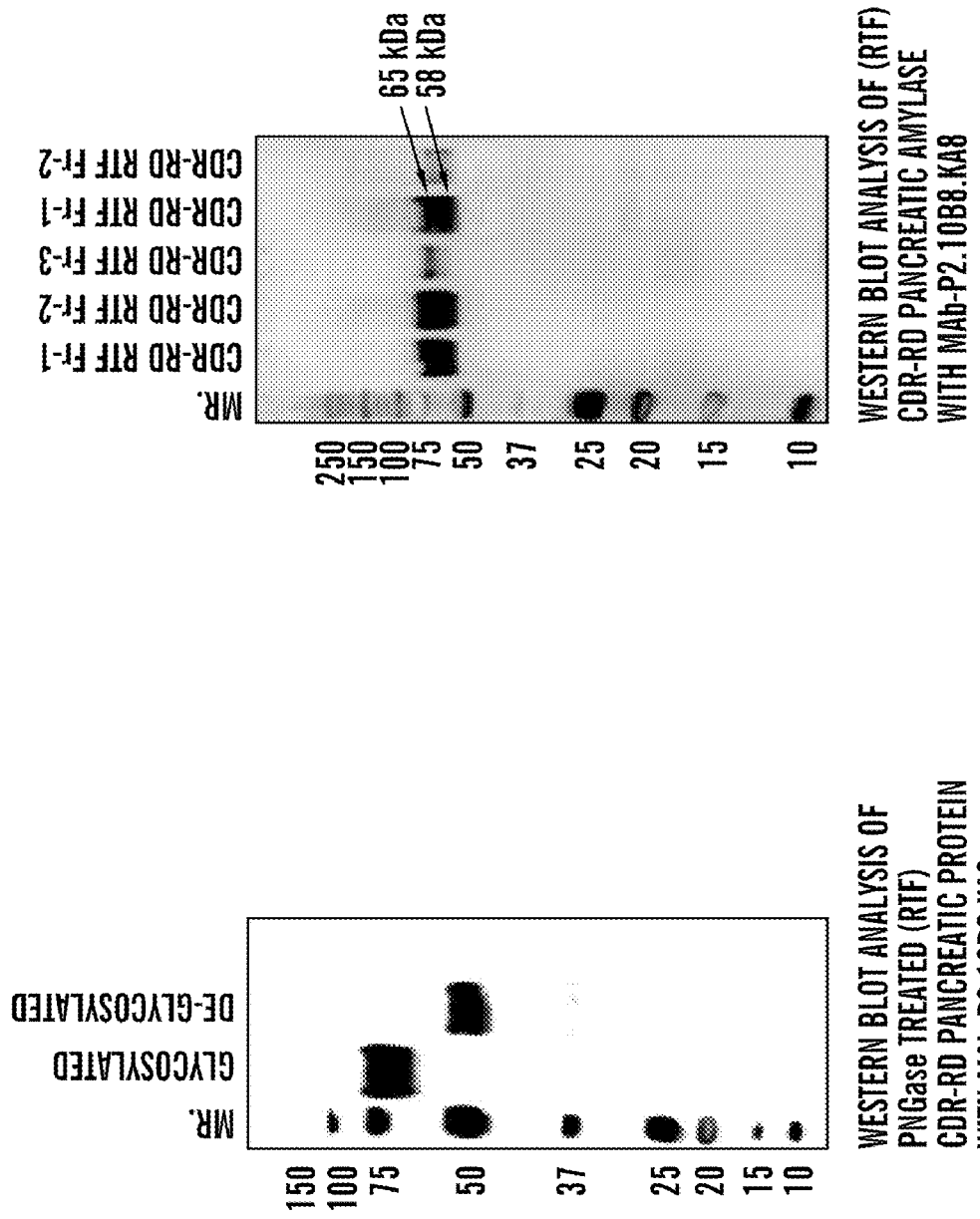
FIG. 7 depicts a Western blot of PNGase-treated (RTF) CDR-RD pancreatic protein and (RTF) CDR-CD pancreatic amylase with the monoclonal hybridoma clone MAb-P2.10B8.KA8.
Figure 8:
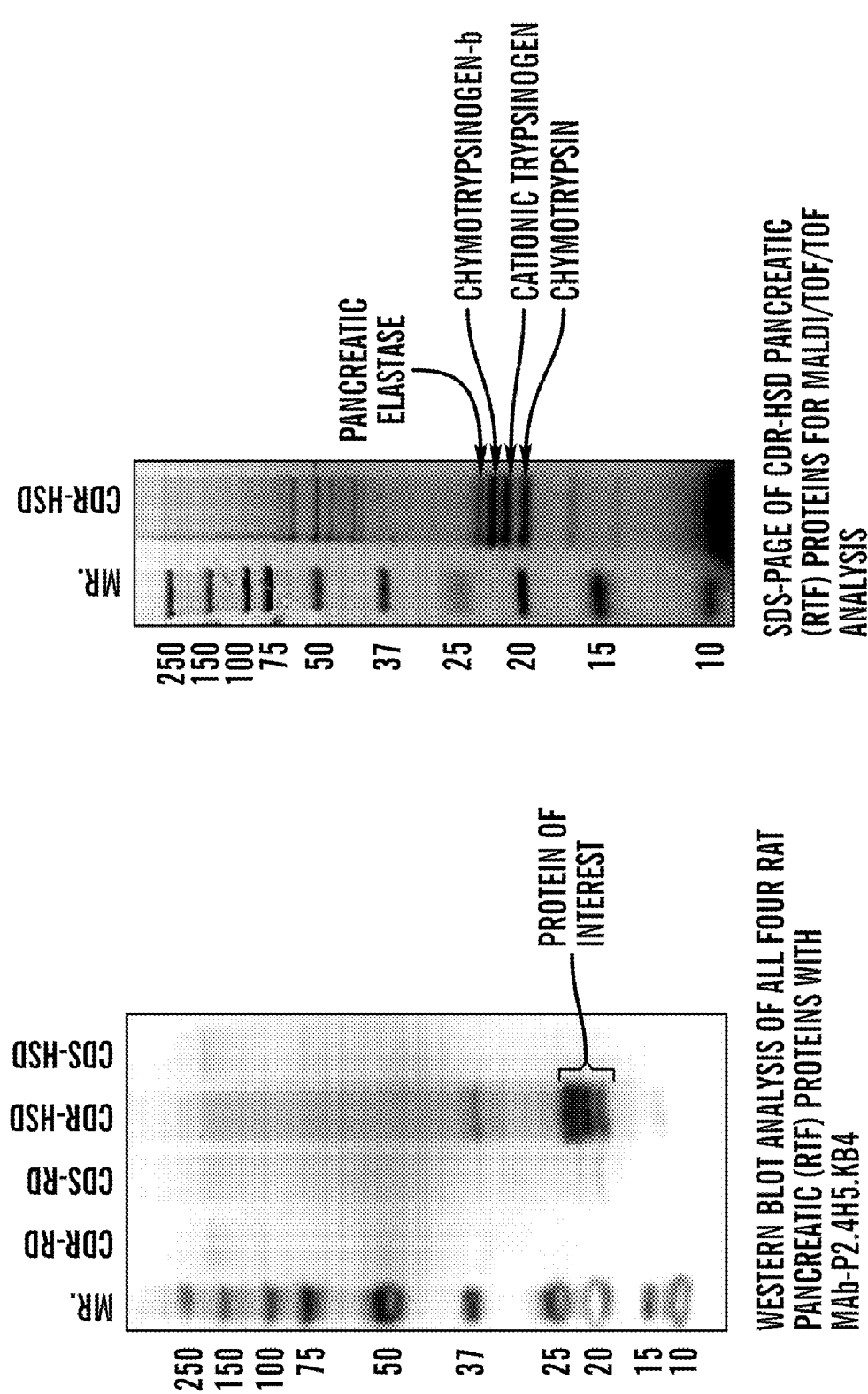
FIG. 8 shows a Western blot depicting the reactivity of MAb-P2-4-H5-K-B4 and an SDS-PAGE of CDR-HSD pancreatic proteins for MALDI/TOF/TOF analysis.

Following precipitation, several bands were visible on the gel after staining for total protein with Coomassie. A faint doublet band was observed in the molecular weight range of 70 to 80 kD. The doublet was confirmed to be the bands of interest by probing a Western Blot prepared from a similar gel with hybridoma clones MAb-P2.19B8.KA8 or P2-4-H %-K-B4 (FIGS. 6 and 7). The doublet bands were excised individually from the SDS-PAGE gel and submitted for identification by mass spectrometry (FIG. 8). An positive identification of the lower band as calnexin was made. Calnexin is a molecular chaperone associated with the endoplasmic reticulum.

Calnexin is a 90 kD integral protein of the endoplasmic reticulum (ER). It consists of a large (50 kD) N-terminal calcium-binding lumenal domain, a single transmembrane helix and a short (90 residues), acidic cytoplasmic tail. Calnexin belongs to a family of proteins known as "chaperones," which are characterized by their main function of assisting protein folding and quality control, ensuring that only properly folded and assembled proteins proceed further along the secretory pathway. The function of calnexin is to retain unfolded or unassembled N-linked glycoproteins in the endoplasmic reticulum. Calnexin binds only those N-glycoproteins that have GlcNAc2Man9Glc1 oligosaccharides. Oligosaccharides with three sequential glucose residues are added to asparagine residues of the nascent proteins in the ER. The monoglucosylated oligosaccharides that are recognized by calnexin result from the trimming of two glucose residues by the sequential action of two glucosidases, I and II. Glucosidase II can also remove the third and last glucose residue. If the glycoprotein is not properly folded, an enzyme called UGGT will add the glucose residue back onto the oligosaccharide thus regenerating the glycoprotein ability to bind to calnexin. The glycoprotein chain which for some reason has difficulty folding up properly thus loiters in the ER, risking the encounter with MNS1 (α-mannosidase), which eventually sentences the underperforming glycoprotein to degradation by removing its mannose residue. ATP and $Ca^{2+}$ are two of the cofactors involved in substrate binding for calnexin.

Example 3

Microarray Analysis of Gene Expression in Tissues from Cohen Type 2 Diabetic Rats The microarray data were analyzed through Phase I and Phase II analyses. Phase I is based on the processed data from Gene Logic. Phase II corresponds to data analysis using GeneSpring GX. Additional criteria including statistics, signaling pathways and clustering were used for the analyses.

The microarray results from Gene Logic (Phase I) that were derived from comparisons of pancreatic total RNA of Cohen Type 2 Diabetes rats (CDs-HSD, CDr-HSD) were analyzed using MAS5.0 software from Affymetrix, Inc. The global gene expression analysis showed that there were 1178 genes upregulated in CDr-HSD and 803 genes were downregulated in compared to CDs-HSD. Many of these transcripts are involved in several signaling pathways related to Type 2 Diabtes such as insulin signaling, beta-cell dysfunction and lipid and glucose metabolisms. Also, several serpin family members (serine proteinase inhibitors) are expressed differently in the two models.

Table 7 provides a summary of the data derived from Gene Logic, wherein changes greater than 3-fold were observed.

TABLE 7

| Signaling Pathways | Upregulated genes CDR-HS vs. CDS-HS | Downregulated genes CDR-HS vs. CDS-HS |
|---|---|---|
| Insulin signaling | 39 | 41 |
| β cell dysfunction (apoptosis, survival) | 17 | 6 |
| Inflammation and immune system | 5 | 92 |
| Mitochondrial dysfunction and reactive oxygen species | 20 | 8 |
| Lipid and glucose metabolisms | 17 | 13 |
| proteinase and proteinase inhibitors | 28 | 17 |
| Amino acid, nucleic acid transporters and metabolisms | 13 | 9 |
| Potassium channels | 3 | 6 |
| ER and Golgi body related genes | 8 | 8 |
| Other unclassified genes | 1028 | 603 |
| Total | 1178 | 803 |

Phase II data analysis was performed using GeneSpring GX, which used normalized data (ratio=transcript signal/control signal) to improve cross-chip comparison. GeneSpring GX allows for gene lists to be filtered according to genes exhibiting a 2-fold or 3-fold change in the expression levels. GeneSpring GX also comprises statistical algorithms, such as ANOVA, Post-Hoc Test, and Cross-Gene Error Modeling, as well as gene clustering algorithms like Gene Tree, K-mean clustering, and Self-Organizing Map (SOM) clustering. GeneSpring GX also has the ability to integrate with pathways that are published in the art, such as the Kyoto Encyclopedia of Genes and Genomes ("KEGG pathways") and Gen Map Annotator and Pathway Profiler (GenMAPP).

Microarray and quantitative PCR analyses were applied to identify the transcriptome changes in pancreatic and epididymal fat tissues of the two strains exposed to a regular diet (RD) or diabetogenic/high sucrose diet (HSD). Both pancreatic tissues and visceral fat tissue-epididymal fat tissue are deemed important primary tissues to study gene transcripts that may play a crucial role in the prediction, progression, and possibly prevention of the disease.

Total RNA was extracted from pancreatic and epididymal fat tissues from each of the strains (CDs, CDr) under regular diet (RD) and diabetogenic diet (HSD). The transcriptome was then analyzed using the Rat Expression Arrays (Affymetrix) set 230 which contains oligonucleotide probes for over 30,000 transcripts. Three to five rats from each groups (CDs-RD, CDs-HSD, CDr-RD and CDr-HSD) were used for data analyses. The results were analyzed using GeneSpring GX (Agilent, Calif.). Expression of several selected transcripts was also confirmed by real-time PCR.

Transcriptome changes of pancreatic tissue were first analyzed via microarray. For this experiment three animals from each of the following groups CDr-HSD and CDs-HSD were analyzed. In CDr-HSD and CDs-HSD rats, eighty-two (82) transcripts show a change of three fold or higher when the two groups are compared (see Tables 8 and 9); nineteen (19) transcripts are downregulated (expression in CDr-HSD is decreased 3 fold or more; Table 9), and sixty-three (63) transcripts were upregulated (expression in CDr-HSD is increased 3 fold or more; Table 8). Fourteen of these transcripts were selected and their changes in the expression levels were confirmed by quantitative PCR. The quantitative PCR analyses validated the changes of expression observed by micorarray analyses.

TABLE 8

Upregulated transcripts expressed 3-fold in CDr-HSD rats

| Name | UniGene (rat) | UniGene (human) | Description and Gene Ontology |
|---|---|---|---|
| REG3G | Rn.11222 | Hs.447084 | Regenerating islet-derived 3 gamma |
| SDF2L1 | Rn.1414 | Hs.303116 | Endoplasmic reticulum stress-inducible gene |
| REG3A | Rn.9727 | Hs.567312 | Regenerating islet-derived 3 alpha |
| MAT1A | Rn.10418 | Hs.282670 | Methionine adenosyltransferase |
| NUPR1 | Rn.11182 | Hs.513463 | Nuclear protein 1 |
| CHAC1 | Rn.23367 | Hs.155569 | Cation transport regulator-like 1 |
| SLC7A3 | Rn.9804 | Hs.175220 | Solute carrier family 7, member 3 |
| PRSS3 | Rn.13006 | Hs.128013 | Protease serine 3 (mesotrypsin) |
| BF415056 | Rn.47821 | n/a | Unknown cDNA |
| PABPC4 | Rn.199400 | Hs.169900 | Ploy A binding protein, cytoplasmic 4 |
| CYP2D6 | Rn.91355 | Hs.648256 | Cytochrome P450, 2D6 |
| AI044556 | Rn.17900 | n/a | unknown |
| PRSS4 | Rn.10387 | Hs.128013 | Mesotrypsin preproprotein |
| GLS2 | Rn.10202 | Hs.212606 | Glutaminase 2 (liver, mitochondrial) |

TABLE 8-continued

Upregulated transcripts expressed 3-fold in CDr-HSD rats

| Name | UniGene (rat) | UniGene (human) | Description and Gene Ontology |
|---|---|---|---|
| NME2 | Rn.927 | Hs.463456 | Nucleoside diphosphate kinase-B |
| P2RX1 | Rn.91176 | Hs.41735 | Purinergic receptor P2X, ligand-gated ion channel 1 |
| PDK4 | Rn.30070 | Hs.8364 | Pyruvate dehydrogenase kinase, isoenzyme 4 |
| AMY1A | Rn.116361 | Hs.484588 | Amylase 1A, 1B and 2A and 2B are closely related |
| CBS | Rn.87853 | Hs.533013 | Cytathionine beta synthase |
| MTE1 | Rn.37524 | Hs.446685 | Acyl-CoA thioesterase2 or mitochondrial acyl-CoA thioesterase |
| SPINK1 | Rn.9767 | Hs.407856 | Serine protease inhibitor, Kazal type 1, |
| GATM | Rn.17661 | Hs.75335 | Glycine amidinotransferase (L-arginine:glycine amidinotransferase) |
| TMED6 | Rn.19837 | Hs.130849 | Transmembrane emp24 protein transport domain containing 6 |
| TFF2 | Rn.34367 | Hs.2979 | Trefoil factor 2 (spasmolytic protein 1) |
| HSD17B13 | Rn.25104 | Hs.284414 | Hydroxysteriod (17-beta) dehydrogenase 13 |
| GNMT | Rn.11142 | Hs.144914 | Glycine N-methyltransferase |
| LRRGT00012 | Rn.11766 | n/a | unknown |
| PAH | Rn.1652 | Hs.652123 | Phenylalanine hydroxylase |
| SERPINI2 | Rn.54500 | Hs.445555 | Serine proteinase inhibitor clade I, member 2 |
| RGD1309615 | Rn.167687 | n/a | Similar to hypothetical protein XP_580018 |
| LRRC39 | Rn.79735 | Hs.44277 | Leucine repeat containing 39 |
| EPRS | Rn.21240 | Hs.497788 | Glutamyl-prolyl-tRNA synthetase |
| PCK2 | Rn.35508 | Hs.75812 | Phosphoenolpyruvate carboxykinase 2 (mitrochondria) |
| AA997640 | Rn.12530 | n/a | unknown |
| SERPINA10 | Rn.10502 | Hs.118620 | Serine peptidase inhibitor, clade A, member 10 |
| SLC30A2 | Rn.11135 | Hs.143545 | Solute carrier family 30 (zinc transporter), member 2 |
| CCKAR | Rn.10184 | Hs.129 | Cholecystokinin A receptor |
| BHLHB8 | Rn.9897 | Hs.511979 | Basic helix-loop-helix domain containing, class B, 8 |
| ANPEP | Rn.11132 | Hs.1239 | Alanyl aminopeptidase |
| ASNS | Rn.11172 | Hs.489207 | Asparagines synthetase |
| SLC7A5 | Rn.32261 | Hs.513797 | Solute carrier family 7 member 5 |
| PABPC4 | Rn.2995 | Hs.169900 | Poly (A) binding protein, cytoplasmic 4 (inducible) |
| KLK1 | Rn.11331 | Hs.123107 | Kallikrein 1 |
| ERP27 | Rn.16083 | Hs.162143 | Endoplasmic reticulum protein 27 KDa |
| QSCN6 | Rn.44920 | Hs.518374 | Quiescin 6 |
| CLDN10 | Rn.99994 | Hs.534377 | Claudin10 |
| MARS | Rn.140163 | Hs.632707 | Methonine-tRNA synthetase |
| EIF4B | Rn.95954 | Hs.292063 | Eukaryotic translation initiation factor 4B |
| RNASE4 | Rn.1742 | Hs.283749 | Ribonuclease, Rnase A family 4 |
| ST6GALNAC4 | Rn.195322 | Hs.3972 | Alpha-2,6-sialytransferase ST6GALNAC 4 |
| HERPUD1 | Rn.4028 | Hs.146393 | Homocysteine-inducible, endoplasmic reticulum stress-inducible, ubiquitin-like domain member 1 |
| DBT | Rn.198610 | Hs.653216 | Dihydrolipoamide branched chain transferase E2 |
| FUT1 | Rn.11382 | Hs.69747 | Fucosyltransferase 1 |
| AL170755 | Rn.22481 | n/a | unknown |
| VLDLR | Rn.9975 | Hs.370422 | Very low density lipoprotein receptor |
| GNPNAT1 | Rn.14702 | Hs.478025 | Glucosamine phosphate N-acetyltransferase 1 |
| DDAH1 | Rn.7398 | Hs.379858 | Dimethylarginine dimethylaminohydrolase 1 |
| HSPA9 | Rn.7535 | Hs.184233 | Heat shock 70 Kda protein 9 |
| PTGER3 | Rn.10361 | Hs.445000 | Prostaglandin E receptor 3 |
| AW523490 | Rn.169405 | n/a | Unknown cNDA |
| RAMP4 | Rn.2119 | Hs.518326 | Ribosome associated membrane |
| MTAC2D1 | Rn.43919 | Hs.510262 | Membrane targeting 9tandem) C2 domain containing 1 |
| DNAJC3 | Rn.162234 | Hs.591209 | DnaJ homolog, subfamily C, member 3 |

TABLE 9

Downregulated transcripts showing 3-fold reduced in expression in CDr-HSD rats

| Name | UniGene (rat) | UniGene (human) | Description and Gene Ontology |
|---|---|---|---|
| CCL21 | Rn.39658 | Hs.57907 | chemokine (C-C motif) ligand 21b |
| IGHG1 | Rn.10956 | Hs.510635 | IGHG1 in human: immunoglobulin heavy constant gamma 1 |
| IGHM | Rn.201760 | Hs.510635 | IGHM: immunoglobulin heavy constant mu |
| Tnfrsf26 | Rn.162508 | n/a | Tumor necrosis factor receptor superfamily, member 26 |
| RGD1306939 | Rn.95357 | n/a | Unknown |

TABLE 9-continued

Downregulated transcripts showing 3-fold reduced in expression in CDr-HSD rats

| Name | UniGene (rat) | UniGene (human) | Description and Gene Ontology |
| --- | --- | --- | --- |
| CD32 | Rn.33323 | Hs.352642 | Fc receptor, IgG, low affinity IIb |
| LCK | Rn.22791 | Hs.470627 | Lymphocyte protein tyrosine kinase |
| SCG5 | Rn.6173 | Hs.156540 | Secretogranin V |
| ARHGD1B | Rn.15842 | Hs.504877 | Rho GDP dissociation inhibitor (GDI) beta |
| RAC2 | Rn.2863 | Hs.517601 | RAS-related C3 botulinum toxin substrate 2 |
| CD45 | Rn.90166 | Hs.192039 | Protein tyrosine phosphatase, receptor type |
| BAT3 | Rn.40130 | Hs.440900 | HLA-B associated transcript 3 |
| CD38 | Rn.11414 | Hs.479214 | CD38 antigen |
| CD132 | Rn.14508 | Hs.84 | Interleukin 2 receptor, gamma |
| ARHGAP30 | Rn.131539 | Hs.389374 | Rho GTPase activating protein 30 |
| CD53 | Rn.31988 | Hs.443057 | CD53 antigen |
| S100B | Rn.8937 | Hs.422181 | S100 calcium binding protein B |
| GIMAP4 | Rn.198155 | Hs.647101 | GTPase, IMAP family member4 |
| RGD1563461 | Rn.199308 | n/a | Unknown |

Given the changes observed in the pancreatic tissue and their consistency by both methods microarray analyses and quantitative PCR, changes in transcriptome levels in epidydimal fat tissue for all four groups of Cohen Diabetic rats were also analyzed. Comparisons among groups may lead to discovery of biomarkers used for either predisposition, progression, and resistance of Type 2 Diabetes. For example, CDr-RD versus CDs-RD comparisons may indicate predisposition for Type 2 Diabetes, while CDs-RD versus CDs-HSD comparisons may serve as a model for progression of the disease, and CDr-HSD versus CDs-HSD comparisons may be used as a model for resistance against development of Type 2 Diabetes.

Tissue samples from five animals from each of the above-mentioned groups were analyzed and the results are summarized herein. Two hundred (200) transcripts, eighty (80) known transcripts and one hundred and twenty (120) unknown transcripts were expressed only in CDs-HSD group, the group that develops Type 2 Diabetes. Twenty-five (25) transcripts with signal strengths (arbitrary fluorescence units) significantly greater than the background noise are listed in Table 10.

TABLE 10

Transcripts Expressed Only in CDs-HSD Rats

| Name | UniGene (rat) | Description and Gene Ontology |
| --- | --- | --- |
| RGD1306952 | Rn.64439 | Similar to Ab2-225 |
| Dmrt2 | Rn.11448 | Doublesex and mab-3 related transcription factor 2 (predicted) |
| AA819893 | Rn.148042 | unknown cDNA |
| Gpr176 | Rn.44656 | G protein-coupled receptor 176 |
| Tmem45b | Rn.42073 | Transmembrane protein 45b |
| Nfkbil1 | Rn.38632 | Nuclear factor of kappa light polypeptide gene enhancer in B-cells inhibitor-like 1 |
| Dctn2 | Rn.101923 | Dynactin 2 |
| Itpkc | Rn.85907 | Inositol 1,4,5-trisphosphate 3-kinase C |
| BM389613 | Rn.171826 | unknown cDNA |
| Prodh2 | Rn.4247 | Proline dehydrogenase (oxidase) 2 |
| BF288777 | Rn.28947 | unknown cDNA |
| Abi3 | Rn.95169 | ABI gene family, member 3 |
| Ring1 | Rn.116589 | Ring finger protein 1 |
| Adrbk1 | Rn.13010 | Adrenergic receptor kinase, beta 1 |
| AW531966 | Rn.8608 | unknown cDNA |
| RGD1560732 | Rn.100399 | Similar to LIM and senescent cell antigen-like domains 1 (predicted) |
| Oxsr1 | Rn.21097 | Oxidative-stress responsive 1 (predicted) |
| MGC114531 | Rn.39247 | unknown cDNA |
| BF418465 | Rn.123735 | unknown cDNA |
| LOC690911 | Rn.25022 | Similar to Msx2-interacting protein (SPEN homolog) |
| Pex6 | Rn.10675 | Peroxisomal biogenesis factor 6 |
| RGD1311424 | Rn.57800 | Similar to hypothetical protein FLJ38348 (predicted) |
| AI013238 | Rn.135595 | unknown cDNA |
| BI288719 | Rn.45106 | unknown cDNA |
| Evpl | Rn.19832 | Envoplakin (predicted) |

The results of comparisons among the three groups are presented in Table 11 below. Among the genes differentially expressed for each of the models, there are several common transcripts.

Table 12 summarizes the results of common and unique transcripts differentially expressed in the resistance and progression models.

TABLE 11

Results of microarray analyses in epididymal fat tissue.

| | Comparisons | | |
|---|---|---|---|
| | CDr-HSD vs. CDs-HSD | CDs-HSD vs. CDs-RD | CDr-RD vs. CDs-RD |
| | | Type of model | |
| | Resistance | Progression | Predisposition |
| >2 fold increase | 140 | 79 | 288 |
| >2 fold decrease | 150 | 98 | 610 |
| >3 fold increase | 26 | 6 | 94 |
| >3 fold decrease | 27 | 22 | 203 |

TABLE 12

Common and Unique transcripts differentially expressed for each model

| Comparisons | Type of model | Common transcripts for both models | Unique transcripts for each model |
|---|---|---|---|
| CDr-HSD vs. CDs-HSD | Resistance | 48 | 242 |
| CDs-HSD vs. CDs-RD | Progression | | 138 |

Figure 9:
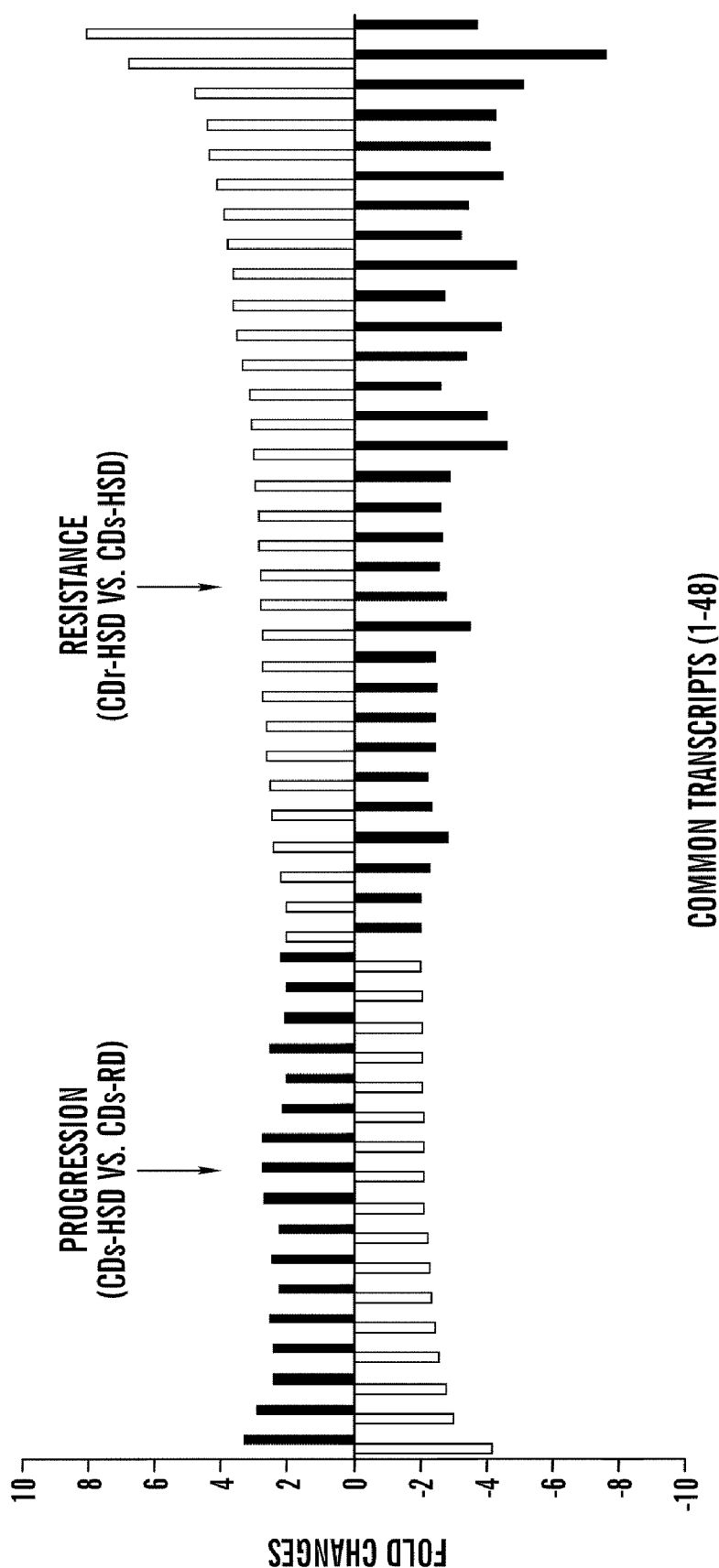
FIG. 9 is a graph depicting the fold changes in expression of 48 markers common to models of progression of Diabetes and models of resistance to Diabetes.

The 48 common transcripts for these two models are listed in Table 13. FIG. 9 is a graph depicting the fold changes in the 48 markers common to these two models.

TABLE 13

Common Transcripts Differentially Expressed in Progression and Resistance Models

| Name | UniGene (rat) | UniGene (human) | Description and Gene Ontology |
|---|---|---|---|
| SERPINE2 | Rn.2271 | Hs.38449 | Serine proteinase inhibitor clade E member 2 |
| C20orf160 | Rn.6807 | Hs.382157 | C20orf160 predicted Cystein type endopeptidase |
| Unknown | Rn.33396 | n/a | unknown |
| LOC338328 | Rn.7294 | Hs.426410 | High density lipoprotein binding protein |
| PTPRR | Rn.6277 | Hs.506076 | Protein tyrosine phosphatase receptor type R, |
| LYPLA3 | Rn.93631 | Hs.632199 | Lysophosphilipase 3 |
| CYYR1 | Rn.1528 | Hs.37445 | Cysteine/tyrosine-rich 1 Membrane-associated protein |
| SOX17 | Rn.7884 | Hs.98367 | SRY-box gene 17 |
| LY6H | Rn.40119 | Hs.159590 | Lymphocyte antigen 6 complex, locus H |
| SEMA3G | Rn.32183 | Hs.59729 | Semaphorin 3G |
| C1QTNF1 | Rn.53880 | Hs.201398 | C1q and tumor necrosis factor related protein 1 |
| ADCY4 | Rn.1904 | Hs.443428 | Adenylate cyclase 4 |
| RBP7 | Rn.13092 | Hs.422688 | Retinol binding protein 7, |
| ADRB3 | Rn.10100 | Hs.2549 | Adrenergic, beta-3-, receptor |
| NR1H3 | Rn.11209 | Hs.438863 | Nuclear receptor subfamily, group H, member 3 |
| TMEFF1 | Rn.162809 | Hs.657066 | Transmembrane protein with EGF-like and two follistatin-like domains 1 |
| TIMP-4 | Rn.155651 | Hs.591665 | Tissue inhibitor of metalloproteinase 4 |
| CYP4F8 | Rn.10170 | Hs.268554 | Cytochrome P450, family 4, subfamily F, polypeptide 8 |
| FOLR1 | Rn.6912 | Hs.73769 | Folate receptor 1 |
| SCD | Rn.83595 | Hs.558396 | Stearoyl-CoA desaturase |
| KIAA2022 | Rn.62924 | Hs.124128 | DNA polymerase activity |
| GK | Rn.44654 | Hs.1466 | Glycerol kinase |
| OCLN | Rn.31429 | Hs.592605 | Occludin |
| SPINT2 | Rn.3857 | Hs.31439 | Serine peptidase inhibitor, Kunitz type, 2 |
| RBM24 | Rn.164640 | Hs.519904 | RNA binding motif protein 24 |
| SLC25A13 | Rn.14686 | Hs.489190 | Solute carrier family 25, member 13 (citrin) |
| TPMT | Rn.112598 | Hs.444319 | Thiopurine S-methyltransferase |
| KRT18 | Rn.103924 | Hs.406013 | Keratin 18 |
| unknown | Rn.153497 | n/a | unknown |
| C2orf40 | Rn.16593 | Hs.43125 | Chromosome 2 open reading frame 40 |
| LOC440335 | Rn.137175 | Hs.390599 | Hypothetical gene supported by BC022385 |
| BEXL1 | Rn.9287 | Hs.184736 | Brain expressed X-linked-like 1 |
| CYB561 | Rn.14673 | Hs.355264 | Cytochrome b-561 |
| AMOT | Rn.149241 | Hs.528051 | Angiomotin |
| SQLE | Rn.33239 | Hs.71465 | Squalene epoxidase |
| ANKRD6 | Rn.45844 | Hs.656539 | Ankyrin repeat domain 6 |
| CCDC8 | Rn.171055 | Hs.97876 | Coiled-coil domain containing 8 |
| KRT8 | Rn.11083 | Hs.533782 | Keratin 8 |
| WWC1 | Rn.101912 | Hs.484047 | WW and C2 domain containing 1 |
| PFKP | Rn.2278 | Hs.26010 | Phosphofructokinase |
| PEBP1 | Rn.29745 | Hs.433863 | Phosphatidylethanolamine binding protein 1 |
| SLC7A1 | Rn.9439 | Hs.14846 | Solute carrier family 7 (cationic amino acid transporter, y+ system), member 1 |
| GSTM1 | Rn.625 | Hs.301961 | Glutathione S-transferase M1 Glutathione metabolism |

TABLE 13-continued

Common Transcripts Differentially Expressed in Progression and Resistance Models

| Name | UniGene (rat) | UniGene (human) | Description and Gene Ontology |
| --- | --- | --- | --- |
| CCL5 | Rn.8019 | Hs.514821 | Chemokine (C-C motif) ligand 5 |
| STEAP1 | Rn.51773 | Hs.61635 | Six transmembrane epithelial antigen of the prostate 1 |
| IAH1 | Rn.8209 | Hs.656852 | Isoamyl acetate-hydrolyzing esterase 1 homolog (*S. cerevisiae*) |
| GNA14 | Rn.35127 | Hs.657795 | Guanine nucleotide binding protein (G protein), alpha 14 |
| TMEM64 | Rn.164935 | Hs.567759 | transmembrane protein 64 |

Unique transcripts that show a change in expression of 3 fold or higher are listed in Table 14. These transcripts are unique in the sense that the changes of the expression level are observed only within one of the models described and as such, they may serve as markers to further study resistance against Type 2 Diabetes or progression and predisposition for the disease.

TABLE 14

Unique Transcripts Found in Epididymal Fat Tissue with Changes Greater than 3-Fold.

| Name | UniGene (rat) | UniGene (human) | Description and Gene Ontology |
| --- | --- | --- | --- |
| SDF2L1 | Rn.1414 | Hs.303116 | Stromal cell-derived factor 2-like 1 |
| CCL11 | Rn.10632 | Hs.54460 | Chemokine (C-C motif) ligand 11 |
| CNN1 | Rn.31788 | Hs.465929 | Calponin 1 |
| ZCD2 | Rn.24858 | Hs.556638 | Zinc finger, CDGSH-type domain 2 |
| CYR61 | Rn.22129 | Hs.8867 | Cysteine-rich, angiogenic inducer, 61 |
| GGH | Rn.10260 | Hs.78619 | Gamma-glutamyl hydrolase |
| TPM3 | Rn.17580 | Hs.645521 | Tropomyosin 3 |
| CSNK1A1 | Rn.23810 | Hs.654547 | Casein kinase 1, alpha 1 |
| PCDH7 | Rn.25383 | Hs.570785 | Protocadherin 7 |
| FHL2 | Rn.3849 | Hs.443687 | Four and a half LIM domains 2 |
| COL11A1 | Rn.260 | Hs.523446 | Collagen, type XI, alpha 1 |
| EMB | Rn.16221 | Hs.645309 | Embigin homolog (mouse) |
| ISG15 | Rn.198318 | Hs.458485 | ISG15 ubiquitin-like modifier |
| CRYAB | Rn.98208 | Hs.408767 | Crystallin, alpha B |
| ACADSB | Rn.44423 | Hs.81934 | Acyl-Coenzyme A dehydrogenase, |
| Unknown | Rn.164743 | n/a | Unknown |
| ABCA1 | Rn.3724 | Hs.429294 | ATP-binding cassette, sub-family A (ABC1), member 1 |
| Unknown | Rn.7699 | n/a | IMAGE clone: BC086433 |
| ACSM3 | Rn.88644 | Hs.653192 | Acyl-CoA synthetase medium-chain family member 3 |
| CHD2 | Rn.162437 | Hs.220864 | Chromodomain helicase DNA binding protein 2 |
| ACTA2 | Rn.195319 | Hs.500483 | Actin, alpha 2, smooth muscle, aorta |
| RAMP3 | Rn.48672 | Hs.25691 | Receptor (G protein-coupled) activity modifying protein 3 |
| DDEF1 | Rn.63466 | Hs.655552 | Development and differentiation enhancing factor 1 |
| NIPSNAP3A | Rn.8287 | Hs.591897 | Nipsnap homolog 3A (*C. elegans*) |
| Unknown | Rn.9546 | n/a | Unknown |
| GPR64 | Rn.57243 | Hs.146978 | G protein-coupled receptor 64 |
| SGCB | Rn.98258 | Hs.438953 | Sarcoglycan, beta |
| Unknown | Rn.146540 | n/a | Unknown |
| Unknown | Rn.199679 | n/a | Unknown |
| CALML3 | Rn.105124 | Hs.239600 | Calmodulin-like 3 |
| LOC645638 | Rn.41321 | Hs.463652 | Similar to WDNM1-like protein |
| RAB8B | Rn.10995 | Hs.389733 | RAB8B, a member RAS oncogene family |
| Unknown | Rn.6638 | n/a | Unknown |
| YTHDF2 | Rn.21737 | Hs.532286 | YTH domain family, member 2 |
| SCEL | Rn.34468 | Hs.534699 | Sciellin |
| BNC1 | Rn.26595 | Hs.459153 | Basonuclin 1 |
| FGL2 | Rn.64635 | Hs.520989 | Fibrinogen-like 2 |
| UPK1B | Rn.9134 | Hs.271580 | Uroplakin 1B |
| CTDSPL | Rn.37030 | Hs.475963 | CTD (carboxy-terminal domain, RNA polymerase II, polypeptide A) small phosphatase-like |
| PIK3R1 | Rn.163585 | Hs.132225 | Phosphoinositide-3-kinase, regulatory subunit 1 (p85 alpha) |

TABLE 14-continued

Unique Transcripts Found in Epididymal Fat Tissue with Changes Greater than 3-Fold.

| Name | UniGene (rat) | UniGene (human) | Description and Gene Ontology |
|---|---|---|---|
| POLA2 | Rn.153998 | Hs.201897 | Polymerase (DNA directed), alpha 2 (70 kD subunit) |
| SPTBN1 | Rn.93208 | Hs.659362 | Spectrin, beta, non-erythrocytic 1 |
| RTEL1 | Rn.98315 | Hs.434878 | Regulator of telomere elongation helicase 1 |
| MSLN | Rn.18607 | Hs.408488 | Mesothelin |
| ARVCF | Rn.220 | Hs.655877 | Armadillo repeat gene deletes in velocardiofacial syndrome |
| ALB | Rn.9174 | Hs.418167 | Albumin |
| SLC6A4 | Rn.1663 | Hs.591192 | Solute carrier family 6 (neurotransmitter transporter, serotonin), member 4 |
| SLC2A4 | Rn.1314 | Hs.380691 | Solute carrier family 2 (facilitated glucose transporter), member 4 |
| Unknown | Rn.26537 | n/a | Unknown |
| Unknown | Rn.44072 | n/a | Unknown |
| Unknown | Rn.199355 | n/a | Unknown |
| MRPL4 | Rn.13113 | Hs.279652 | Mitochondrial ribosomal protein L4 |
| GPR109A | Rn.79620 | Hs.524812 | G protein-coupled receptor 109A |

Figure 10:
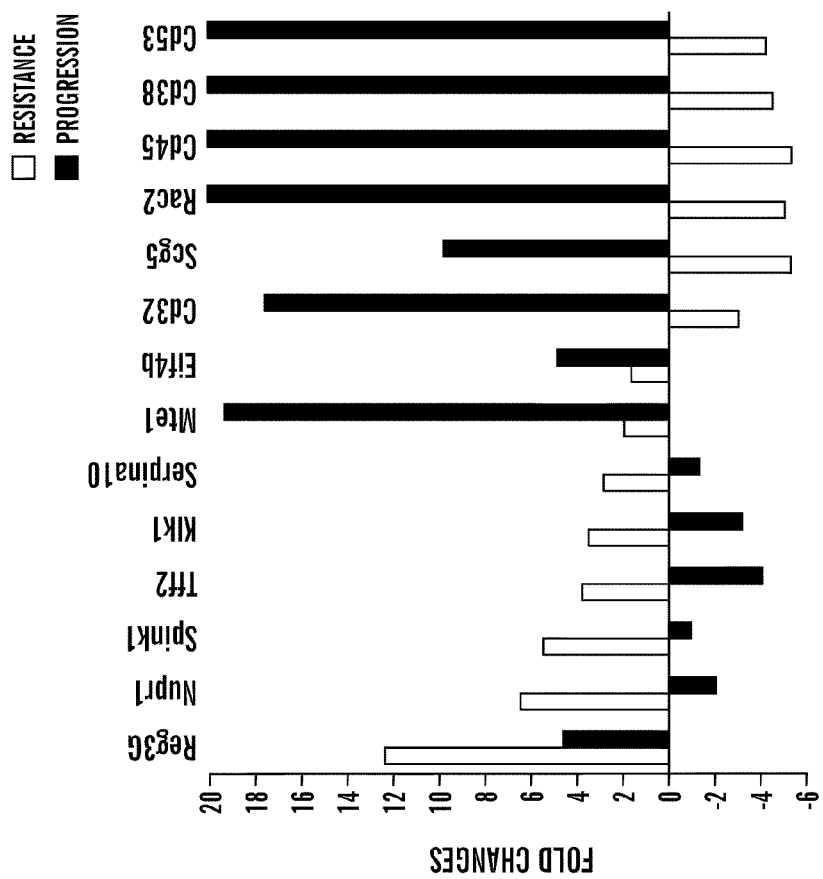
FIG. 10 is a summary graph of expression of selected markers measured in pancreatic tissue.

Transcriptome/gene expression analyses were conducted on pancreatic and epididymal fat tissue for the Cohen rat models. Transcripts differentially expressed for both tissues have been characterized as described above. For selected transcripts (14 transcripts for pancreatic tissue and 48 transcripts for epididymal fat tissue), the microarray results have been confirmed by quantitative PCR. FIG. 10 is a summary graph of the expression of the selected markers measured in pancreatic tissue.

Figure 11A:
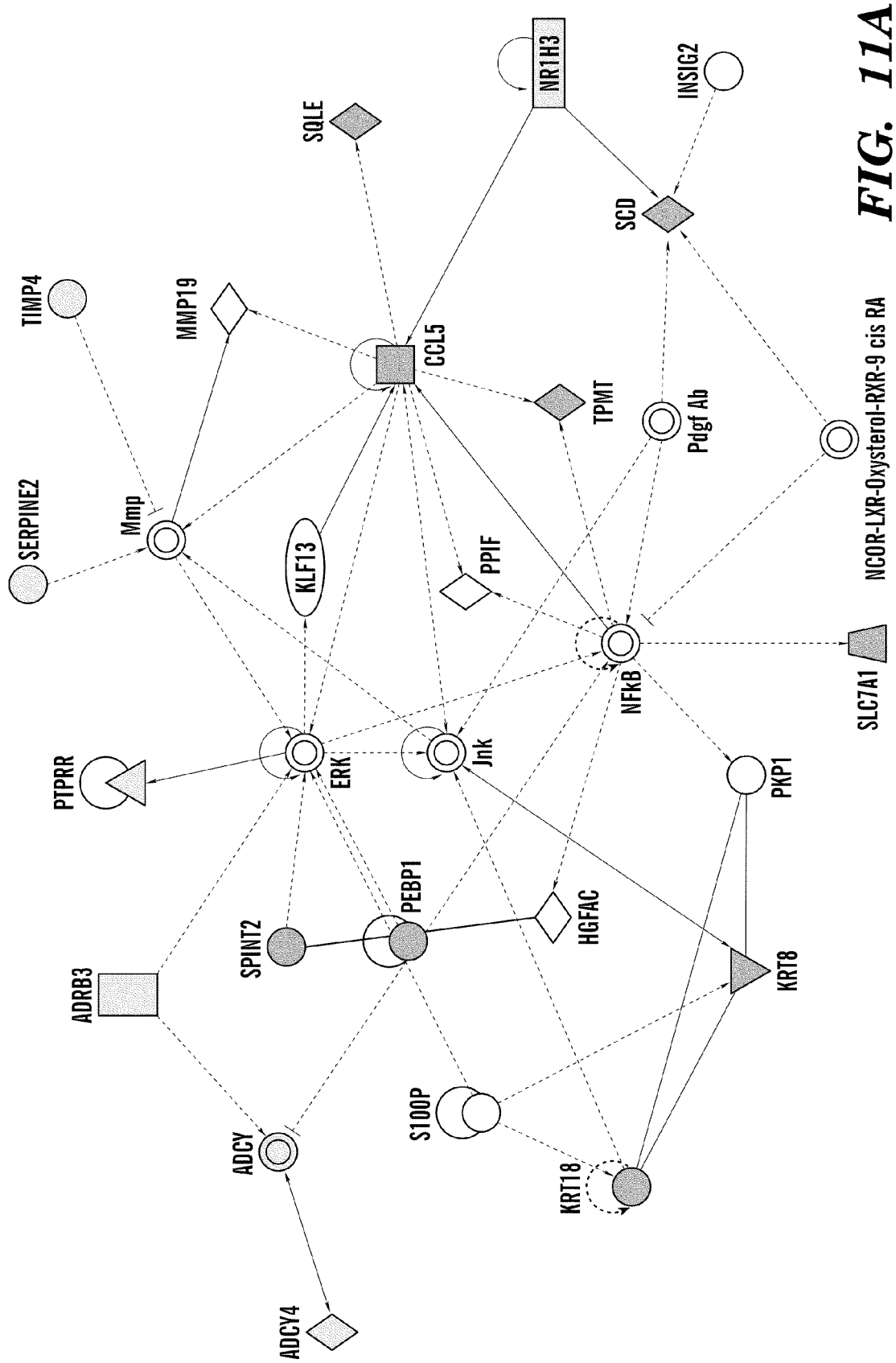
FIG. 11A depicts a network derived from biomarkers identified in epididymal fat from a rat model of Diabetes resistance.
Figure 11B:
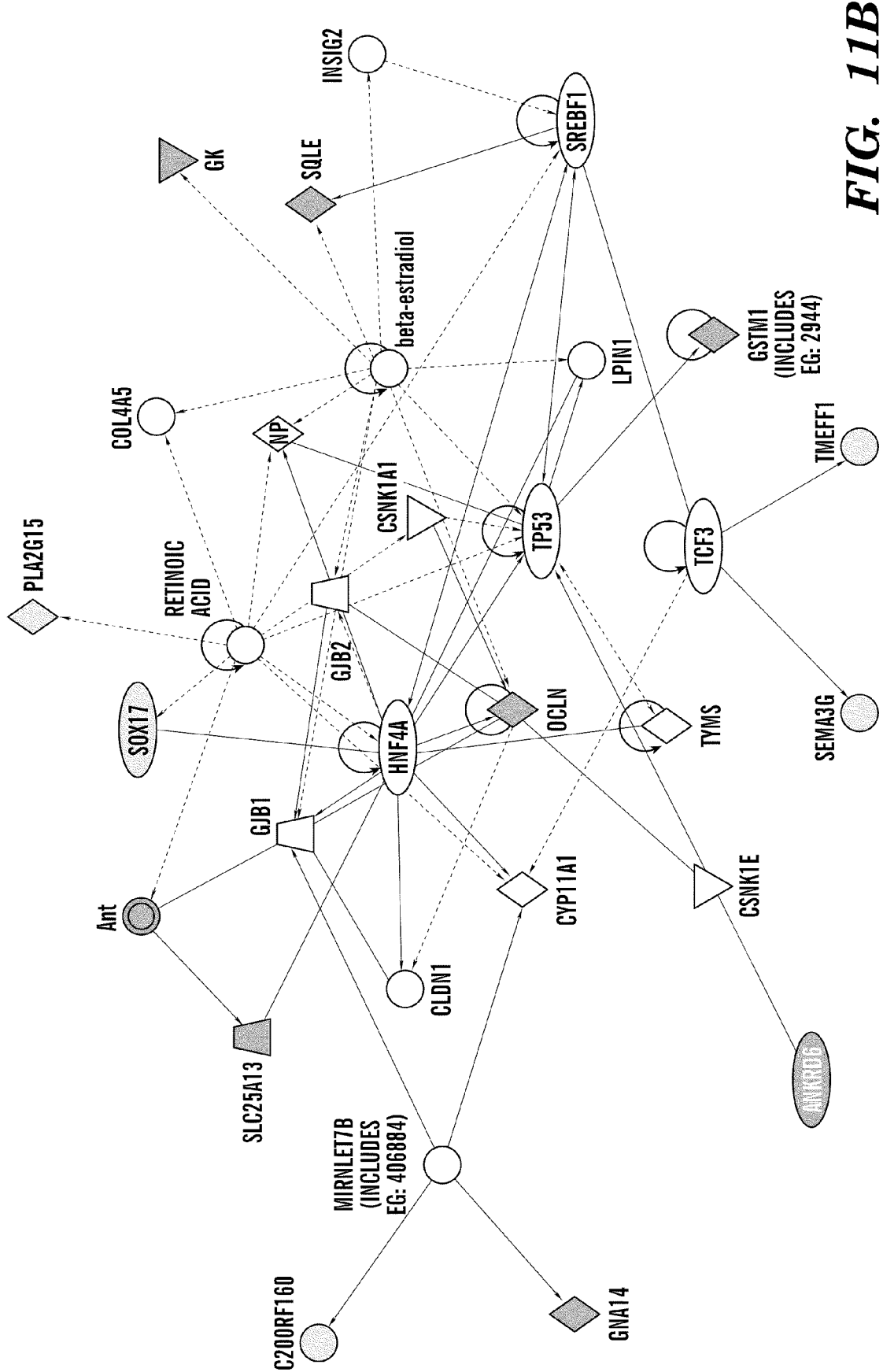
FIG. 11B depicts a network derived from biomarkers identified in epididymal fat from a rat model of Diabetes progression.
Figure 11C:
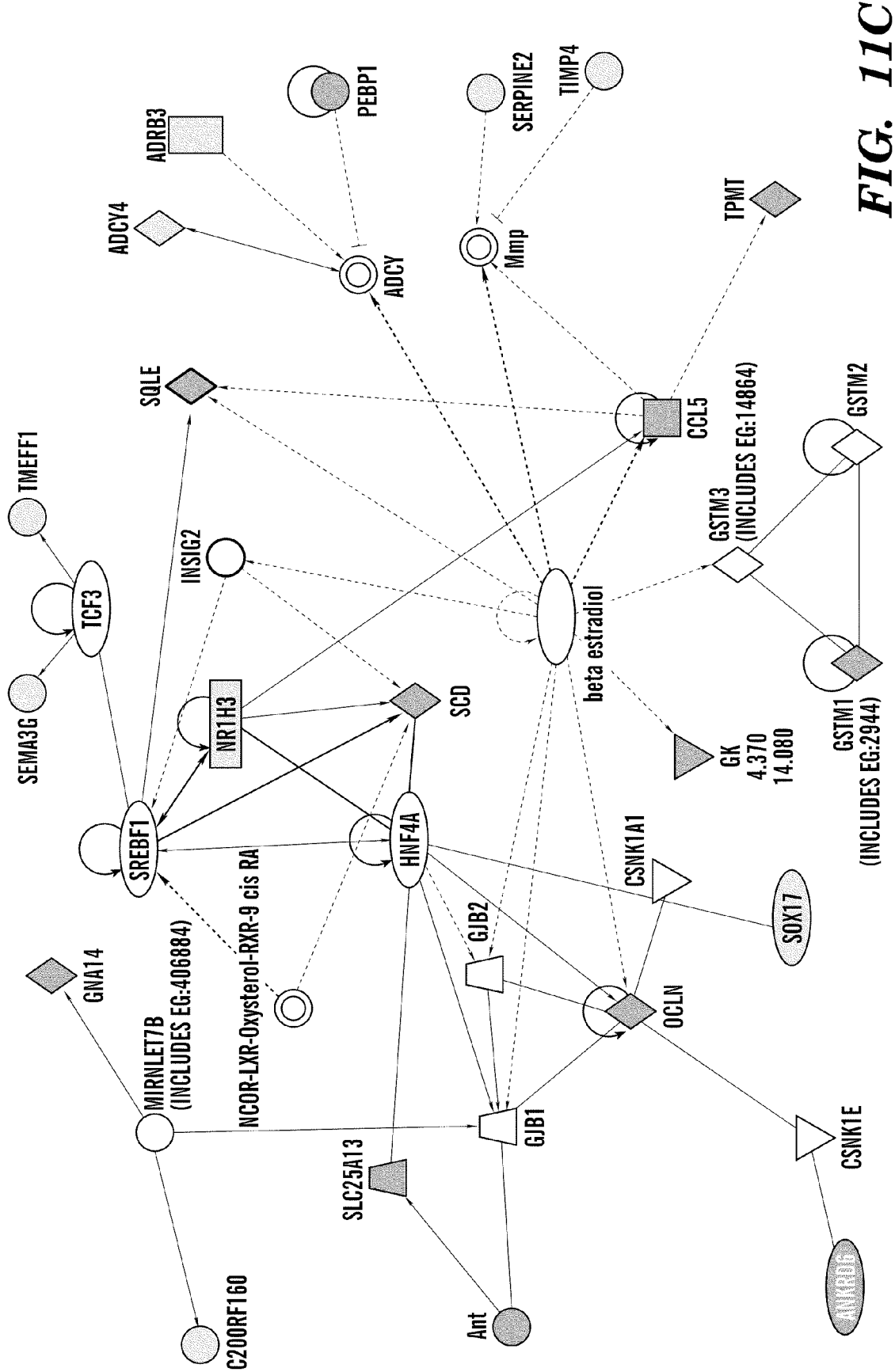
FIG. 11C shows a network that combined the networks depicted in FIGS. 11A and 11B.

The 48 gene expression biomarkers common between models of resistance and progression were mapped according to resistance alone (FIG. 11A) or progression alone (FIG. 11B). FIG. 11C shows the "merged" network, wherein the top biological functions associated with the identified biomarkers include the following in Table 15:

TABLE 15

Top Biological Functions

| Function | P-value confidence | Biomarkers |
|---|---|---|
| Hepatic system disease | 5.4E−06 to 1.75E−02 | SCD, SLC25A13, KRT8, KRT18, NR1H3, CCL5, GK, ADRB3 |
| Cellular assembly and organization | 8.41E−06 to 4.88E−02 | PEBP1, SCD, KRT8, KRT18, NR1H3, CCL5, OCLN |
| Hair and skin development and function | 8.41E−06 to 4.6E−02 | KRT8, KR18, CCL5 |
| Development and function | 8.41E−06 to 2.61E−02 | SCD, SLC25A13, KRT8, KRT18, NR1H3, CCL5 |

Table 16 lists the top canonical pathways associated with the biomarkers identified in epididymal fat:

TABLE 16

Top Canonical Pathways

| Canonical Pathways | P-value confidence | Biomarkers |
|---|---|---|
| PXR/RXR Activation | 1.92E+00 | SCD, GSTM1 (includes EG: 2944) |
| LXR/RXR Activation | 1.90E+00 | SCD, NR1H3 |
| Hepatic Cholestasis | 1.34E+00 | ADCY4, NR1H3 |
| Synaptic Long Term Depression | 1.27E+00 | ADCY4, GNA14 |
| CXCR4 Signaling | 1.25E+00 | ADCY4, GNA14 |
| RAR Activation | 1.18E+00 | RBP7, ADCY4 |

TABLE 16-continued

Top Canonical Pathways

| Canonical Pathways | P-value confidence | Biomarkers |
|---|---|---|
| Biosynthesis of Steroids | 1.17E_00 | SQLE |
| PPARO±/RXRO± Activation | 1.17E+00 | ADCY4, GK |
| cAMP-mediated Signaling | 1.16E+00 | ADCY4, ADRB3 |

Figure 12A:
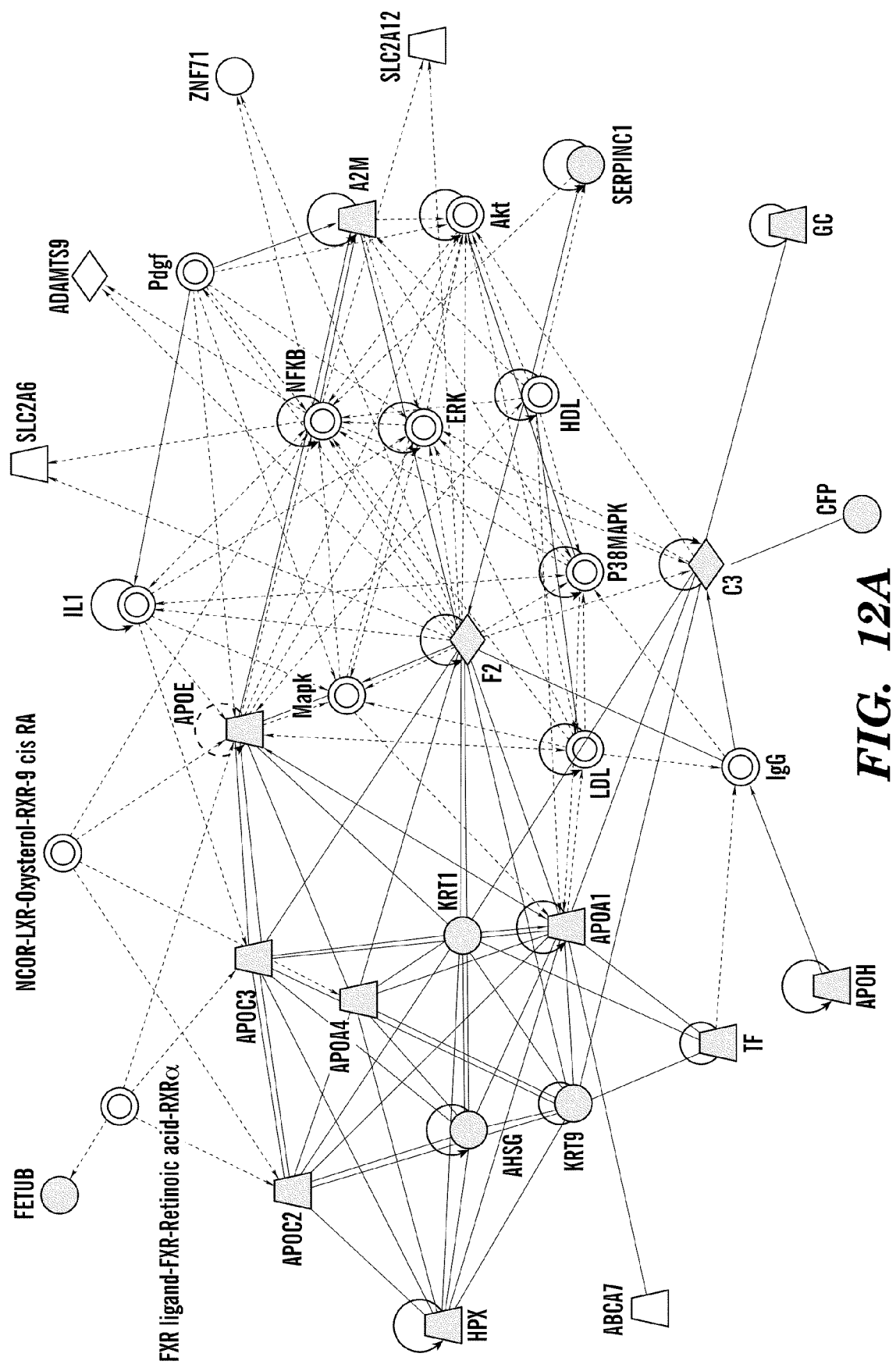
FIG. 12A depicts a network combining most of the biomarkers common to models of progression of Diabetes and models of resistance to Diabetes.
Figure 12B:
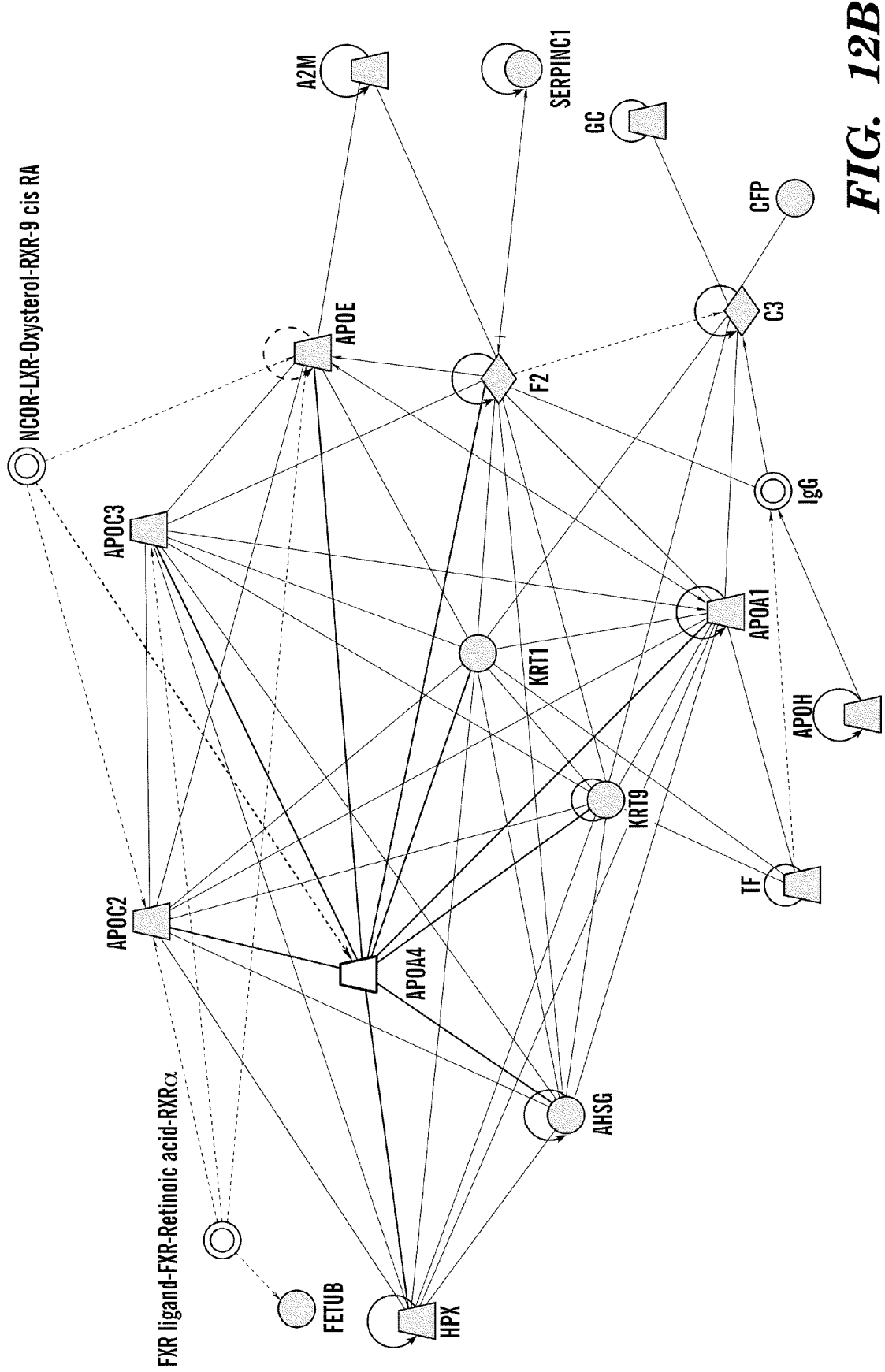
FIG. 12B shows a simplified version of the network depicted in FIG. 12A.
Figure 12C:
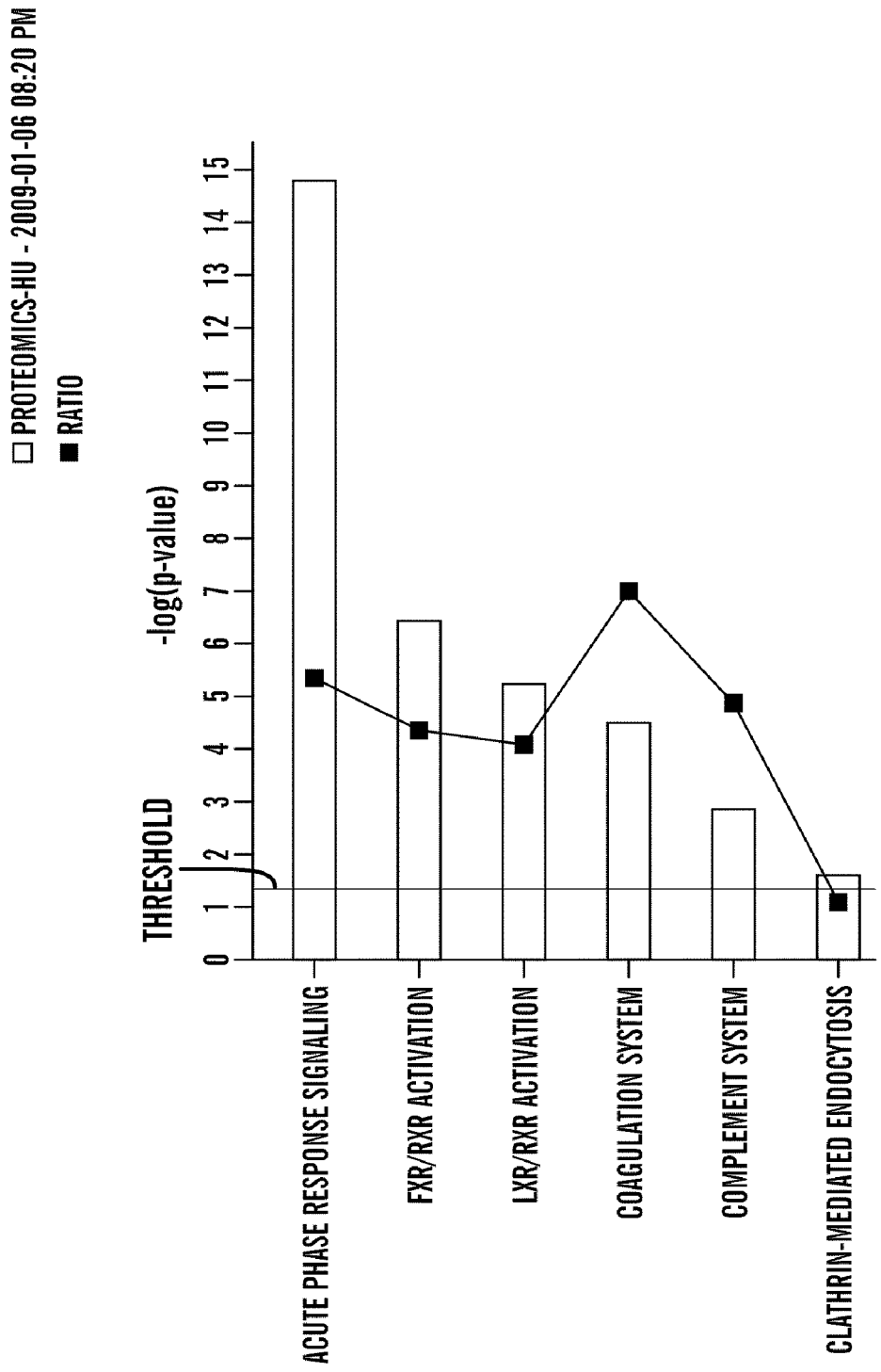
FIG. 12C is a bar graph depicting the top canonical pathways implicated in the bioinformatics assays of Example 3.
Figure 12D:
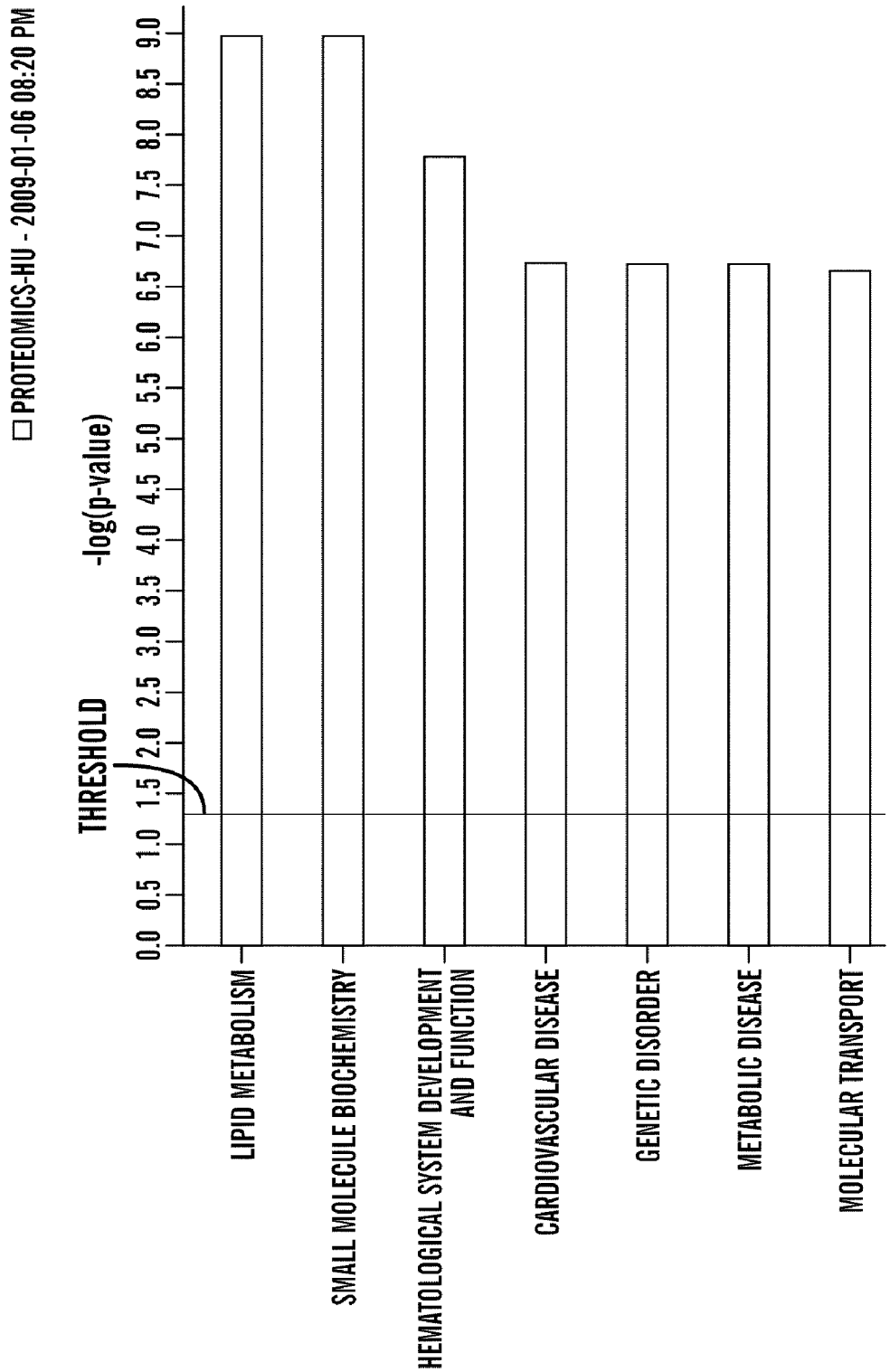
FIG. 12D is a bar graph depicting the top biological functions implicated in the bioinformatics assays described in Example 3.

FIG. 12A depicts a network combining most of the identified biomarkers from serum in the Cohen rat models discussed herein. FIG. 12B shows a simplified version of the network depicted in FIG. 12A. FIG. 12C is a bar graph depicting the top canonical pathways implicated in the bioinformatics analyses discussed herein, while FIG. 12D shows the top implicated biological functions.

Example 4

In Vivo Efficacy of D3 Peptide in the Streptozotocin (STZ) Model of Diabetes

To examine the possible role of D3 peptide in preventing the onset of T2D in the CD rat model, the efficacy of synthetically produced D3 peptide to ameliorate the severity of experimental type 2 Diabetes Mellitus in a multiple low dose streptozotocin (STZ)-induced murine model was tested.

In a 36-day prophylactic study using STZ-induced male C57BL/6 mice, treatment with 1 mg/kg of D3 peptide every 3 days resulted in 100% survival of treated animals compared to 60% survival in untreated controls. Peptide treatment also delayed the onset of Diabetes (mean blood glucose levels≧300 mg/dL) by approximately 14 days, and reduced peak BG levels by 40% (p<0.01) in treated animals. This naturally occurring peptide may represent a safer alternative to small molecule kinase inhibitors for the control of IDDM and associated complications.

Streptozotocin (Streptozocin, STZ, Zanosar) is a naturally occurring glucosamine-nitrosourea compound that is toxic to insulin producing beta cells in the pancreas. This alkylating agent bears enough similarity to the molecular structure of glucose to be readily transported into beta cells by the highly abundant glucose GLU2 glucose transporter protein. Once inside the cell STZ causes damage to the DNA, resulting in a loss of cellular function. Administration of this compound to experimental animals selectively inhibits beta cell function resulting in a deregulation of glucose metabolism and hyperglycemia, both characteristics of type 1 or type 2 Diabetes.

Twenty five male C57BL/6 mice aged approximately 6 weeks were randomized into 3 groups of 10, 10 and 5 animals. Beginning on day −6, non-fasting blood glucose (BG) levels for all animals were determined twice weekly using an Ascencia Contour blood glucose reader (Beyer). Also beginning on day −6, one group of 10 animals (Group 2) was administered 1 mg of D3 peptide in 200 µl sterile water intraperitoneally. Groups 1 and 3 were intraperitoneally administered 200 µl sterile water alone. Injections continued in a similar fashion every 3 days for the duration of the experiment. Beginning on day 0, Groups 2 and 3 also received 50 mg/kg of STZ in 200 µl of sterile water via the intraperitoneal route for 5 consecutive days. Group 1 animals received a mock intraperitoneal injection of 200 µl of sterile water during the same period (see Table 17). Animals were allowed access to food and water ad libitum and this treatment schedule was followed until day 36.

TABLE 17

Experimental design for efficacy study of D3 peptide in STZ induced diabetic C57BL/6 mice.

| Group No. | No. of Animals | BG Level | Treatment | Disease Induction | Description |
|---|---|---|---|---|---|
| 1 | 5 | Biweekly | $H_2O$ | $H_2O$ | Normal Control |
| 2 | 10 | Biweekly | D3 Peptide | STZ | Treated Diabetic |
| 3 | 10 | Biweekly | $H_2O$ | STZ | Untreated Diabetic |

In experiment 1, animals were fed normal mouse chow for the duration of the experiment and a fresh vial of STZ was used. Blood glucose measurements for each individual animal were recorded twice weekly for the duration of the experiment. The blood glucose levels in the non diabetic control animals remained stable at approximately 150 mg/dl. However, immediately following the administration of STZ to the two experimental groups, blood glucose levels increased steadily over time and reached a maximum at approximately day 15. No difference in blood glucose levels were observed between D3 treated and untreated STZ-induced animals.

Figure 14:
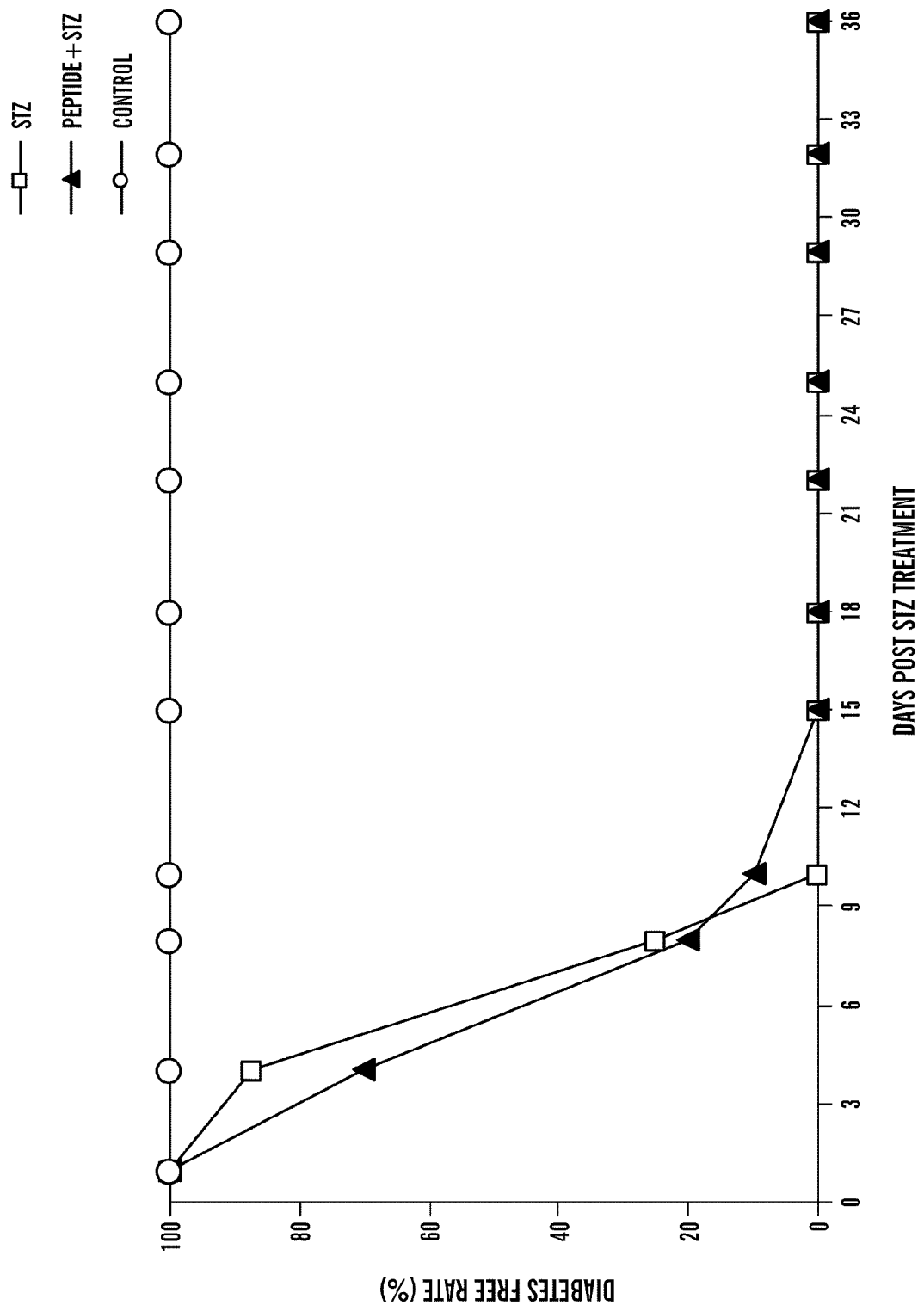
FIG. 14 is a graph showing onset of diabetes in STZ treated animals. No significant differences were noted in the time to onset or rate of disease in D3 treated animals, when compared to untreated diabetic controls.

For the duration of the experiment, the mean blood glucose level of normal control animals was approximately 150 mg/dl. For the purposes of this study, a blood glucose reading in STZ-induced animals more than 2-fold higher than normal (i.e. ≧300 mg/dl) was considered to indicate a diabetic animal. Using this criterion, the incidence and time to onset of diabetes in the treated and untreated STZ groups was determined. The results (FIG. 14) show that none of the normal control animals displayed any sign of diabetes throughout the experiment. For both STZ groups, the onset of Diabetes began as early as day 4 post STZ administration. All of the untreated STZ animals were classed as diabetic by day 10. For the D3 peptide treated animals, the first signs of Diabetes also manifested on day 4, although the time to establish Diabetes in 100% of these animals slightly longer at day 15. The rate of disease progression in treated animals (slope of the graph) was essentially similar for both groups.

Figure 15:
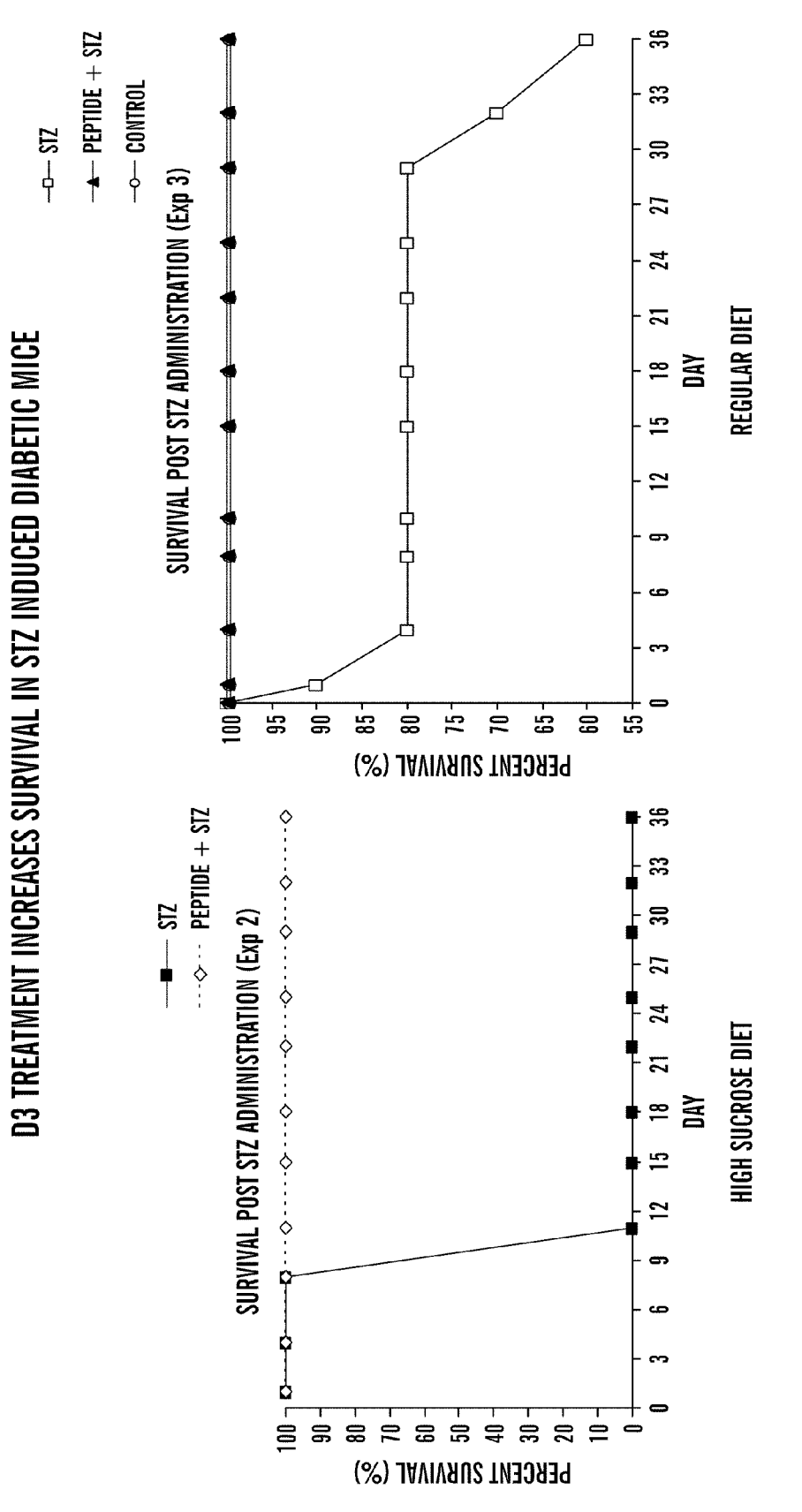
FIG. 15 are graphs showing that treatment with the D3 peptide increases survival in diabetic mice induced with streptozocin.

Once Diabetes is evident in these animals, several changes in animal behavior were observed. Urination becomes more frequent as animals try to excrete excess sugar, grooming is less evident and fur becomes ruffled and pilated. As disease becomes more severe, lethargy can ensue and animals can succumb to diabetic complications rendering them moribund, or resulting in death. In the untreated diabetic group, some initial deaths were recorded following the initial onset of disease with only 80% of animals surviving past day 4. Later in the experiment, further mortality was observed for this group with only 60% of animals reaching the end of the experiment on day 36 (see FIG. 15). In contrast, no mortality was observed in D3 treated animals during the course of the study. As expected, the survival rate was 100% in the normal control group.

Figure 16:
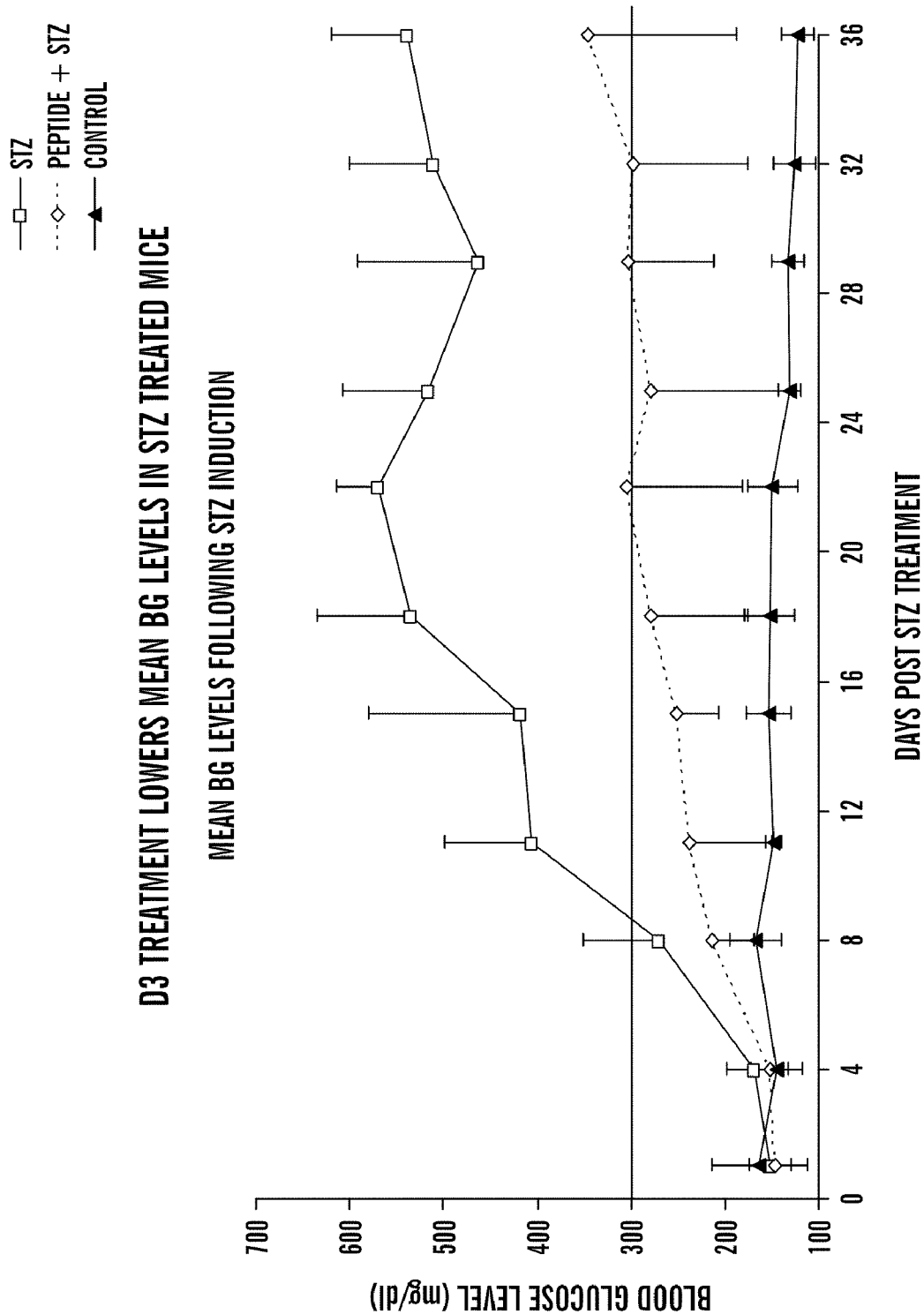
FIG. 16 is a graph depicting that animals administered STZ alone demonstrate a significant increase in mean blood glucose levels compared to normal controls over a 36 day period. In contrast, blood glucose levels in STZ-induced animals also receiving D3 peptide show a marked reduction.

In experiment 2, animals were fed a high carbohydrate diet (~50% sucrose) for the duration of the experiment. An older stock vial of STZ was used. Blood glucose measurements for each individual animal were recorded twice weekly for the duration of the experiment. The data is summarized in FIG. 16. As expected, the blood glucose levels in the non diabetic control animals remained below 150 mg/dl. However, blood glucose levels for both STZ-induced animals increased over time, compared to the control group, and were significantly greater than normal from day 8 onwards (p≦0.05). For the groups receiving STZ, the mean blood glucose levels in untreated diabetic animals were higher than those observed in diabetic animals treated with D3 peptide every 3 days, with significant differences (p≦0.05) first observed on day 10. This trend was maintained for the entire duration of the experiment.

For the duration of the experiment, the mean blood glucose level of normal control animals was approximately 150 mg/dl. For the purposes of this study, a blood glucose reading in STZ-induced animals more than 2-fold higher than normal (i.e. ≧300 mg/dl) was considered to indicate a diabetic animal. Using this criterion, the incidence and time to onset of Diabetes in the treated and untreated STZ groups was determined. The results showed that none of the normal control animals showed any signed of Diabetes throughout the experiment. For the untreated STZ group, Diabetes onset began as early as day 8 post STZ administration, and 100% of animals were diabetic by day 18. For the D3 peptide treated animals however, the first signs of diabetes did not manifest until day 12, four days later than in untreated animals. The rate of disease progression in treated animals (slope of the graph) was much less pronounced in D3 treated animals. By day 36 only 70% of animals in the D3 treated group were classified as diabetic. No animals succumbed to diabetic complications or experienced any toxic events related to peptide or STZ treatment during this study.

In experiment 3, animals were fed a high sucrose diet ad libitum upon arrival. D3 peptide was administered at 1 mg per animal every 3 days in water via the intraperitoneal route beginning on day −6. Diabetes was induced by the intraperitoneal administration of 50 mg/kg of fresh STZ in 0.1 mM sodium citrate buffer (pH 4.5) for 5 consecutive days, beginning on day 0. Blood glucose was measured twice weekly using an Ascencia Countour BG meter (Beyer, maximum reading is 600 mg/dL). On day 37, a glucose tolerance test was administered by injecting 2 g/kg of glucose IP and monitoring BG levels at 0, 15, 30, 60, 120 and 180 minutes post injection. After GTT, animals were switched to regular mouse chow and peptide treatment was halted. BG levels were followed for a further 21 days. The experiment was terminated on day 69, at which time serum samples were obtained from each animal and pancreata were removed and formalin fixed for possible histological analysis.

Example 5

Serpina D3 Peptide Inhibits Kinases in vitro

Kinase assays were performed using the ProfilerPro kinase panel kit available from NovaScreen and were validated using the KinaseProfiler enzyme panel available from Millipore. To obtain information of biological activity and selectivity of the D3 peptide, this lead biomarker was first tested at a concentration of 1 µM for binding by NovaScreen to 59 receptors, including 25 neurotransmitter-related receptors, 4 steroid receptors, 3 ion channels, 2 second messengers, 2 growth factors/hormones, 7 Brain/gut peptides, and 16 enzymes including 12 Kinases. The preliminary results indicated that the D3 peptide showed specific inhibition activities to 7 kinases that are involved in insulin receptor signaling pathways. To confirm this finding, two concentrations of D3 peptide (0.1 uM and 1 uM) were used to test for binding in the same 12 kinases using the Millipore enzyme panel. The data confirmed that the D3 peptides have specific inhibition activity on 4 out of 7 kinases highlighted in Table 18 with $IC_{50}$ values ranging from 0.3 µM-1 µM.

TABLE 18

Kinase Profiling Data Summary

| Kinase | D3 at 0.1 µM % activity | D3 at 1 µm % activity | $IC_{50}$ (µM) |
| --- | --- | --- | --- |
| GSK3β(h) | 101 | 100 | |
| IKKβ(h) | 103 | 71 | |
| IR (h) | 96 | 103 | |
| MAPK1(h) | 86 | 92 | |
| MAPK2(h) | 96 | 96 | |
| P70S6K(h) | 73 | 22 | 0.373 |
| PDK1(h) | 98 | 108 | |
| PKA(h) | 115 | 105 | |
| PKBβ(h) | 63 | 12 | 0.448 |
| PKCβII(h) | 101 | 103 | |
| PKCζ(h) | 95 | 42 | 1.045 |
| SGK(h) | 74 | 5 | 0.325 |

Two kinase screens were performed using the Invitrogen SelectScreen™ biochemical kinase profiling service. The Z'-LYTE® biochemical assay employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair. In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress, as shown in the equation:

$$\text{Emission Ratio} = \frac{\text{Coumarin Emission (445 nm)}}{\text{Fluorescein Emission (520 nm)}}$$

The assay yields very high Z'-factor values (>0.7) at a low percent phosphorylation. Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

Test Compounds are screened in 1% DMSO (final) in the well. For 10 point titrations, 3-fold serial dilutions are conducted from the starting concentration selected by the present inventors. All Peptide/Kinase Mixtures are diluted to a 2× working concentration in the appropriate Kinase Buffer. All ATP Solutions are diluted to a 4× working concentration in Kinase Buffer (50 mM HEPES pH 7.5, 0.01% BRIJ-35, 10 mM $MgCl_2$, 1 mM EGTA). ATP $K_m$ apparent is previously determined using a Z'-LYTE® assay. The Development Reagent is diluted in Development Buffer: 10× Novel PKC Lipid Mix: 2 mg/ml Phosphatidyl Serine, 0.2 mg/ml DAG in 20 mM HEPES, pH 7.4, 0.3% CHAPS. For 5 mL 10× Novel PKC Lipid Mix, ten mg of phosphatidylserine and 1 mg diacylglycerol were added to a glass tube. The lipid mixture was removed from the chloroform by evaporation under a stream of nitrogen and dried. To the dried lipid mixture, 5 mL of resuspension buffer, 10% CHAPS/500 mM HEPES, pH 7.4, was added. The mixture was then heated gently to 50-60° C. and vortexed in short intervals until the lipids dissolved and the solution appeared clear. The mixture was divided into single use volumes and stored at –20° C.

To a bar-coded Corning, low volume NBS, black 384-well plate, the following components were added: 2.5 µL of 4× Test Compound or 100 nL 100× plus 2.4 µL kinase buffer, 5 µL of 2× Peptide/Kinase Mixture, and 2.5 µL of 4×ATP Solution. The plate was shaken for 30 seconds, then incubated for 60 minutes at room temperature to allow the kinase reaction to run. After incubation, 5 µL of Development Reagent Solution was added, then the plate was shaken for another 30-seconds and incubated at room temperature for another 60 minutes. Fluorescence was captured on a fluorescence plate reader and the data was analyzed alongside the following controls, which were made for each individual kinase and located on the same plate as the kinase: 0% Phosphorylation Control (100% Inhibition Control), 100% Phosphorylation Control, and 0% Inhibition Control. The maximum Emission Ratio is established by the 0% Phosphorylation Control (100% Inhibition Control), which contains no ATP and therefore exhibits no kinase activity. This control yields 100% cleaved peptide in the Development Reaction. The 100% Phosphorylation Control, which consists of a synthetically phosphorylated peptide of the same sequence as the peptide substrate, is designed to allow for the calculation of percent phosphorylation. This control yields a very low percentage of cleaved peptide in the Development Reaction. The 0% Phosphorylation and 100% Phosphorylation Controls allow one to calculate the percent Phosphorylation achieved in a specific reaction well. Control wells do not include any kinase inhibitors.

The minimum Emission Ratio in a screen is established by the 0% Inhibition Control, which contains active kinase. This control is designed to produce a 10-50% phosphorylated peptide in the Kinase Reaction. A known inhibitor control standard curve, 10 point titration, is run for each individual kinase on the same plate as the kinase to ensure the kinase is inhibited within an expected $IC_{50}$ range previously determined.

The following controls are prepared for each concentration of Test Compound assayed: "Development Reaction Interference," which is established by comparing the Test Compound Control wells that do not contain ATP versus the 0% Phosphorylation Control (which does not contain the Test Compound). The expected value for a non-interfering compound should be 100% and any value outside of 90% to 110% is flagged; Test Compound Fluorescence Interference, which is determined by comparing the Test Compound Control wells that do not contain the Kinase/Peptide Mixture (zero peptide control) versus the 0% Inhibition Control. The expected value for a non-fluorescence compound should be 0%. Any value>20% is flagged. Table 19 is a list of equations that were used for each set of data points:

TABLE 19

Equations Used in Data Analysis

| | Equation |
|---|---|
| Correction for Background Fluorescence | FI Sample − FI TCFI Ctl |
| Emission Ratio (using values corrected for background fluorescence) | Coumarin Emission (445 nm) / Fluorescein Emission (520 nm) |
| % Phosphorylation (% Phos) | {1 − (Emission Ratio × F100%) − C100% (C0% − C100%) + [Emission Ratio × (F100% − F0%)]} * 100 |
| % Inhibition | {1 − % Phos Sample / % Phos 0% Inhibition Ctl} * 100 |
| Z' (using Emission Ratio values) | 1 − 3 * Stdev 0% Phos Ctl + 3 * Stdev 0% Inhibition / Mean 0% Phos Ctl − Mean 0% Inhibition |
| Difference Between Data Points (single point only) | \|% Inhibition Point 1 − % Inhibition Point 2\| |
| Development Reaction Interference (DRI) (no ATP control) | Emission Ratio DRI Ctl / Emission Ratio 0% Phos Ctl |
| Test Compound Fluorescence Interference (TCFI) (check both Coumarin and Fluorescein emissions) | FI TCFI Ctl / FI 0% Inhibitor Ctl |

FI = Fluorescence Intensity
C100% = Average Coumarin emission signal of the 100% Phos. Control
C0% = Average Coumarin emission signal of the 0% Phos. Control
F100% = Average Fluorescein emission signal of the 100% Phos. Control
F0% = Average Fluorescein emission signal of the 0% Phos. Control The SELECTSCREEN™ Kinase Profiling Service used XLfit from IDBS as graphing software. The dose response curve is curve fit to model number 205 (sigmoidal dose-response model). If the bottom of the curve does not fit between −20% & 20% inhibition, it is set to 0% inhibition. If the top of the curve does not fit between 70% and 130% inhibition, it is set to 100% inhibition.

Table 20 below provides a summary of the results of the two Invitrogen SelectScreen™ kinase profiling assays:

| | % Inhibition | Annotation | | |
|---|---|---|---|---|
| Kinase Tested | mean | Group | Family | Subfamily |
| NEK9 NIMA (never in mitosis gene a)-related kinase 9 | 108.33 | | NEK | NEK8 |
| MAP2K2 (MEK2) Mitogen-activated protein kinase kinase 2 | 104.81 | STE | STE7 | MEK1 |
| SGK2 Serum/glucocorticoid regulated kinase 2 | 101.80 | AGC | SGK | |
| MAP3K9 (MLK1) Mitogen-activated protein kinase kinase kinase 9 | 100.99 | TKL | MLK | MLK |
| MINK1 Misshapen-like kinase 1 | 100.96 | | | |
| MST4 | 100.88 | STE | STE20 | YSK |
| PRKG2 (PKG2) | 100.88 | AGC | PKG | |
| SGK (SGK1) Serum/glucocorticoid regulated kinase | 100.46 | AGC | SGK | |

-continued

| Kinase Tested | % Inhibition mean | Group | Family | Subfamily |
|---|---|---|---|---|
| RPS6KB1 (p70S6K) Ribosomal protein S6 kinase, 70 kDa, polypeptide 1 | 100 | AGC | RSK | p70 |
| BRAF V-raf murine sarcoma viral oncogene homolog B1 | 100.40 | TKL | RAF | RAF |
| MAP4K4 (HGK) | 100 | STE | STE20 | MSN |
| PRKX | 100.32 | AGC | PKA | |
| TAOK2 (TAO1) TAO kinase 2 | 100.15 | STE | STE20 | TAO |
| BRAF V599E V-raf murine sarcoma viral oncogene homolog B1 V599E mutation | 99.79 | | | |
| CAMK4 (CaMKIV) Calcium/calmodulin-dependent protein kinase IV | 99.58 | CAMK | CAMK1 | |
| STK4 (MST1) Serine/threonine kinase 4 | 98.95 | STE | STE20 | MST |
| STK24 (MST3) Serine/threonine kinase 24 (STE20 homolog, yeast) | 98.63 | STE | STE20 | YSK |
| MAP3K8 (COT) Mitogen-activated protein kinase kinase kinase 8 | 98.58 | STE | STE-Unique | |
| MAP4K2 (GCK) Mitogen-activated protein kinase kinase kinase kinase 2 | 98.41 | STE | STE20 | KHS |
| RPS6KA1 (RSK1) Ribosomal protein S6 kinase, 90 kDa, polypeptide 1 | 98.30 | AGC | RSK | RSK |
| CAMK1D (CaMKI delta) Calcium/calmodulin-dependent protein kinase I delta | 98.01 | CAMK | CAMK1 | |
| NEK6 NIMA (never in mitosis gene a)-related kinase 6 | 97.42 | NEK | NEK6 | Other |
| SGKL (SGK3) Serum/glucocorticoid regulated kinase family, member 3 | 97.00 | AGC | SGK | |
| RPS6KA4 (MSK2) Ribosomal protein S6 kinase, 90 kDa, polypeptide 4 | 96.82 | AGC | RSK | MSK |
| IRAK4 IRAK4 (interleukin-1 receptor-associated kinase 4) | 96 | TKL | IRAK | |
| RAF1 (cRAF) Y340D Y341D c-Raf | 94.58 | TKL | RAF | RAF |
| MAP2K1 (MEK1) | 94 | STE | STE7 | MEK1 |
| STK25 (YSK1) Serine/threonine kinase 25 (STE20 homolog, yeast) | 93.14 | STE | STE20 | YSK |
| RPS6KA3 (RSK2) Ribosomal protein S6 kinase, 90 kDa, polypeptide 3 | 93 | AGC | RSK | RSK |
| MAPK9 (JNK2) Mitogen-activated protein kinase 9 | 92.94 | CMGC | MAPK | JNK |
| PRKD2 (PKD2) Protein kinase D2 | 92.53 | CAMK | PKD | |
| MAPK10 (JNK3) Mitogen-activated protein kinase 10 | 90.65 | CMGC | MAPK | JNK |
| STK3 (MST2) Serine/threonine kinase 3 (STE20 homolog, yeast) | 90.37 | STE | STE20 | MST |
| CAMK2B (CaMKII beta) | 90.26 | | | |
| PIM2 | 89.94 | | | |
| NEK2 | 89.57 | | | |
| PIM1 Pim-1 oncogene | 89 | CAMK | PIM | |

-continued

| Kinase Tested | % Inhibition mean | Annotation Group | Family | Subfamily |
|---|---|---|---|---|
| MAPK8 (JNK1) Mitogen-activated protein kinase 8 | 89 | CMGC | MAPK | JNK |
| PRKCB1 (PKC beta I) Protein kinase C, beta 1, | 88 | AGC | PKC | Alpha |
| RPS6KA6 (RSK4) | 87.62 | | | |
| PHKG2 Phosphorylase kinase, gamma 2 | 87 | CAMK | PHK | |
| AMPK A2/B1/G1 | 86.48 | | | |
| PRKCQ (PKC theta) | 86.33 | | | |
| MAP4K5 (KHS1) | 86.31 | | | |
| MELK | 85.80 | | | |
| RPS6KA5 (MSK1) | 85.05 | | | |
| NEK1 NIMA (never in mitosis gene a)-related kinase 1 | 84 | OTHER | NEK | NEK1 |
| BRSK1 (SAD1) | 83.46 | | | |
| MAPK14 (p38 alpha) Mitogen-activated protein kinase 14 | 83 | CMGC | MAPK | p38 |
| CAMK2A (CaMKII alpha) | 82.58 | | | |
| PRKCG (PKC gamma) | 81.02 | | | |
| PASK | 80.82 | | | |
| PRKD1 (PKC mu) | 80.58 | | | |
| MERTK (cMER) | 79.55 | | | |
| SRPK2 | 79.19 | | | |
| AMPK A1/B1/G1 AMP-activated protein kinase | 79 | CAMK | CAMKL | AMPK |
| PRKCZ (PKC zeta) | 74.39 | | | |
| CHEK1 (CHK1) CHK1 checkpoint homolog | 74 | CAMK | CAMKL | CHK1 |
| NEK7 | 73.81 | | | |
| CAMK2D (CaMKII delta) | 72.54 | | | |
| TYK2 | 70.50 | | | |
| ABL1 T315I | 69.85 | | | |
| PRKCN (PKD3) | 69.58 | | | |
| AKT2 (PKB beta) | 67.74 | | | |
| ADRBK2 (GRK3) | 66.73 | | | |
| ROCK2 | 66.70 | | | |
| TEK (Tie2) Tyrosine kinase, endothelial | 67 | TK | Tie | |
| CLK2 | 65.89 | | | |
| ABL1 E255K | 65.63 | | | |
| MYLK2 (skMLCK) | 64.57 | | | |
| MAPKAPK3 | 64.06 | | | |
| PKN1 (PRK1) | 64.00 | | | |
| PDK1 | 63.95 | | | |
| CHEK2 (CHK2) | 62.13 | | | |
| DAPK3 (ZIPK) | 62.04 | | | |
| PRKCB2 (PKC beta II) | 61.65 | | | |
| DYRK4 | 61.23 | | | |
| GRK4 | 58.65 | | | |
| MAPKAPK2 Mitogen-activated protein kinase-activated protein kinase 2 | 58 | CAMK | MAPKAPK | MAPKAPK |
| PRKCD (PKC delta) | 57.41 | | | |
| GRK6 | 57.06 | | | |
| ADRBK1 (GRK2) | 56.06 | | | |
| MATK (HYL) | 55.61 | | | |
| CSK | 55.21 | | | |
| PHKG1 | 54.82 | | | |
| SYK Spleen tyrosine kinase | 54 | TKL | Syk | |
| GRK5 | 50.83 | | | |
| ABL1 G250E | 50.74 | | | |
| PLK1 Polo-like kinase 1 | 51 | | | |
| GRK7 | 49.86 | | | |
| PRKCI (PKC iota) | 48.93 | | | |
| PAK4 P21(CDKN1A)-activated kinase 4 | 47 | STE | STE20 | PAKB |

-continued

| Kinase Tested | % Inhibition mean | Annotation | | |
|---|---|---|---|---|
| | | Group | Family | Subfamily |
| SRMS (Srm) | 46.49 | | | |
| PRKCH (PKC eta) | 46.46 | | | |
| CLK3 | 45.99 | | | |
| PRKCA (PKC alpha) | 45.09 | | | |
| IKBKB (IKK beta) IKK2 | 41 | OTHER | IKK | |

It is to be understood that while the invention has been described in conjunction with the detailed description thereof, the foregoing description is intended to illustrate and not limit the scope of the invention, which is defined by the scope of the appended claims. Other aspects, advantages, and modifications are within the ambit of the following claims.

What is claimed is:

1. A method of treating type 2 Diabetes or a pre-diabetic condition in a subject, comprising administering to the subject a pharmaceutical composition comprising as an active ingredient an isolated peptide of SEQ ID No.: 1 and a pharmaceutically acceptable carrier or diluent.

2. The method of claim 1, wherein the pharmaceutical composition is co-administered with a second therapeutic agent.

3. The method of claim 1, wherein the isolated peptide of SEQ. ID. No. 1 has an effective concentration of 5-100 μM in a pharmaceutical preparation.

4. The method of claim 1, wherein the pharmaceutical composition is administered subcutaneously, intramuscularly, intravenously, or intraperitoneally.

5. The method of claim 1, wherein the subject is a mammal.

6. The method of claim 5, wherein the mammal is a human.

* * * * *

```
                        SEQUENCE LISTING

<160> NUMBER OF SEQ ID NOS: 28

<210> SEQ ID NO 1
<211> LENGTH: 38
<212> TYPE: PRT
<213> ORGANISM: Rattus norvegicus

<400> SEQUENCE: 1

Ser Gly Arg Pro Pro Met Ile Val Trp Phe Asn Arg Pro Phe Leu Ile
1               5                   10                  15

Ala Val Ser His Thr His Gly Gln Thr Ile Leu Phe Met Ala Lys Val
            20                  25                  30

Ile Asn Pro Val Gly Ala
        35

<210> SEQ ID NO 2
<211> LENGTH: 85
<212> TYPE: PRT
<213> ORGANISM: Rattus norvegicus

<400> SEQUENCE: 2

Phe Ser Gln Gln Ala Asp Leu Ser Arg Ile Thr Gly Ala Lys Asp Leu
1               5                   10                  15

Ser Val Ser Gln Val Val His Lys Val Val Leu Asp Val Asn Glu Thr
            20                  25                  30

Gly Thr Glu Ala Ala Ala Thr Gly Ala Asn Leu Val Pro Arg Ser
        35                  40                  45

Gly Arg Pro Pro Met Ile Val Trp Phe Asn Arg Pro Phe Leu Ile Ala
    50                  55                  60

Val Ser His Thr His Gly Gln Thr Ile Leu Phe Met Ala Lys Val Ile
65                  70                  75                  80

Asn Pro Val Gly Ala
            85

<210> SEQ ID NO 3
<211> LENGTH: 419
<212> TYPE: PRT
<213> ORGANISM: Rattus norvegicus

<400> SEQUENCE: 3

Met Ala Phe Ile Ala Ala Leu Gly Leu Leu Met Ala Gly Ile Cys Pro
1               5                   10                  15

Ala Val Leu Gly Phe Pro Asp Gly Thr Leu Gly Asn Asp Thr Leu Leu
            20                  25                  30
```

```
His Lys Asp Gln Asp Lys Gly Thr Gln Leu Asp Ser Leu Thr Leu Glu
        35                  40                  45

Ser Ile Asn Thr Asp Phe Ala Phe Ser Leu Tyr Lys Met Leu Ala Leu
    50                  55                  60

Lys Asn Pro Asp Lys Asn Val Val Phe Ser Pro Leu Ser Ile Ser Ala
65                  70                  75                  80

Ala Leu Ala Ile Val Ser Leu Gly Ala Lys Gly Asn Thr Leu Glu Glu
                85                  90                  95

Ile Leu Glu Val Leu Arg Phe Asn Leu Thr Glu Ser Tyr Glu Thr Asp
            100                 105                 110

Ile His Gln Gly Phe Gly His Leu Leu Gln Arg Leu Ser Gln Pro Gly
        115                 120                 125

Asp Gln Val Lys Ile Ile Thr Gly Asn Ala Leu Phe Ile Asp Lys Asn
    130                 135                 140

Leu Gln Val Leu Ala Glu Phe Gln Glu Lys Thr Arg Ala Leu Tyr Gln
145                 150                 155                 160

Val Glu Ala Phe Thr Ala Asp Phe Gln Gln Pro Arg Val Thr Glu Lys
                165                 170                 175

Leu Ile Asn Asp Tyr Val Arg Asn Gln Thr Gln Gly Lys Ile Gln Glu
            180                 185                 190

Leu Val Ser Gly Leu Lys Glu Arg Thr Ser Met Val Leu Val Asn Tyr
        195                 200                 205

Leu Leu Phe Arg Gly Lys Trp Lys Val Pro Phe Asp Pro Asp Tyr Thr
    210                 215                 220

Phe Glu Ser Glu Phe Tyr Val Asp Glu Lys Arg Ser Val Lys Val Ser
225                 230                 235                 240

Met Met Lys Ile Glu Glu Leu Thr Thr Pro Tyr Phe Arg Asp Glu Glu
                245                 250                 255

Leu Ser Cys Ser Val Leu Glu Leu Lys Tyr Thr Gly Asn Ser Ser Ala
            260                 265                 270

Leu Phe Ile Leu Pro Asp Lys Gly Arg Met Gln Gln Val Glu Ala Ser
        275                 280                 285

Leu Gln Pro Glu Thr Leu Lys Lys Trp Lys Asp Ser Leu Arg Pro Arg
    290                 295                 300

Lys Ile Asp Glu Leu Tyr Leu Pro Arg Leu Ser Ile Ser Thr Asp Tyr
305                 310                 315                 320

Ser Leu Glu Glu Val Leu Pro Glu Leu Gly Ile Arg Asp Val Phe Ser
                325                 330                 335

Gln Gln Ala Asp Leu Ser Arg Ile Thr Gly Ala Lys Asp Leu Ser Val
            340                 345                 350

Ser Gln Val Val His Lys Val Val Leu Asp Val Asn Glu Thr Gly Thr
        355                 360                 365

Glu Ala Ala Ala Ala Thr Gly Ala Asn Leu Val Pro Arg Ser Gly Arg
    370                 375                 380

Pro Pro Met Ile Val Trp Phe Asn Arg Pro Phe Leu Ile Ala Val Ser
385                 390                 395                 400

His Thr His Gly Gln Thr Ile Leu Phe Met Ala Lys Val Ile Asn Pro
                405                 410                 415

Val Gly Ala

<210> SEQ ID NO 4
<211> LENGTH: 17
<212> TYPE: DNA
<213> ORGANISM: Artificial
```

```
<220> FEATURE:
<223> OTHER INFORMATION: Description of Artificial Sequence: Synthetic
      primer

<400> SEQUENCE: 4
ttcaacmrrc cyttyst                                                  17

<210> SEQ ID NO 5
<211> LENGTH: 18
<212> TYPE: DNA
<213> ORGANISM: Artificial
<220> FEATURE:
<223> OTHER INFORMATION: Description of Artificial Sequence: Synthetic
      primer

<400> SEQUENCE: 5
yvacyttkcy makraaga                                                 18

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Asn Arg Pro Phe Leu
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Gly
<220> FEATURE:
<221> NAME/KEY: MOD_RES
<222> LOCATION: (6)..(6)
<223> OTHER INFORMATION: Thr or Val

<400> SEQUENCE: 7

Phe Met Xaa Lys Val Xaa Asn Pro
1               5

<210> SEQ ID NO 8
<211> LENGTH: 32
<212> TYPE: PRT
<213> ORGANISM: Homo sapiens

<400> SEQUENCE: 8

Ile Val Arg Phe Asn Arg Pro Phe Leu Met Ile Ile Val Pro Thr Asp
1               5                   10                  15

Thr Gln Asn Ile Phe Phe Met Ser Lys Val Thr Asn Pro Lys Gln Ala
            20                  25                  30

<210> SEQ ID NO 9
<211> LENGTH: 31
<212> TYPE: PRT
<213> ORGANISM: Homo sapiens
```

-continued

```
<400> SEQUENCE: 9

Ile Val Phe Asn Arg Pro Phe Leu Met Ile Ile Val Pro Thr Asp Thr
1               5                   10                  15

Gln Asn Ile Phe Phe Met Ser Lys Val Thr Asn Pro Lys Gln Ala
            20                  25                  30

<210> SEQ ID NO 10
<211> LENGTH: 31
<212> TYPE: PRT
<213> ORGANISM: Homo sapiens

<400> SEQUENCE: 10

Ile Val Phe Asn Arg Pro Phe Leu Met Ile Ile Val Pro Thr Asp Thr
1               5                   10                  15

Gln Asn Ile Phe Phe Met Ser Lys Val Thr Asn Pro Lys Gln Ala
            20                  25                  30

<210> SEQ ID NO 11
<211> LENGTH: 32
<212> TYPE: PRT
<213> ORGANISM: Homo sapiens

<400> SEQUENCE: 11

Pro Pro Val Phe Asn Lys Pro Phe Val Phe Leu Met Ile Glu Gln Asn
1               5                   10                  15

Thr Lys Ser Pro Leu Phe Met Gly Lys Val Val Asn Pro Thr Gln Lys
            20                  25                  30

<210> SEQ ID NO 12
<211> LENGTH: 30
<212> TYPE: PRT
<213> ORGANISM: Homo sapiens

<400> SEQUENCE: 12

Ile Phe Asn Arg Pro Phe Leu Val Val Ile Phe Ser Thr Ser Thr Gln
1               5                   10                  15

Ser Val Leu Phe Leu Gly Lys Val Val Asp Pro Thr Lys Pro
            20                  25                  30

<210> SEQ ID NO 13
<211> LENGTH: 30
<212> TYPE: PRT
<213> ORGANISM: Homo sapiens

<400> SEQUENCE: 13

Ile Phe Asn Arg Pro Phe Leu Val Val Ile Phe Ser Thr Ser Thr Gln
1               5                   10                  15

Ser Val Leu Phe Leu Gly Lys Val Val Asp Pro Thr Lys Pro
            20                  25                  30

<210> SEQ ID NO 14
<211> LENGTH: 30
<212> TYPE: PRT
<213> ORGANISM: Homo sapiens

<400> SEQUENCE: 14

Pro Phe Asn Lys Pro Phe Val Phe Leu Met Ile Glu Gln Asn Thr Lys
1               5                   10                  15

Ser Pro Leu Phe Met Gly Lys Val Val Asn Pro Thr Gln Lys
            20                  25                  30
```

```
<210> SEQ ID NO 15
<211> LENGTH: 29
<212> TYPE: PRT
<213> ORGANISM: Homo sapiens

<400> SEQUENCE: 15

Phe Asn Arg Pro Phe Leu Val Ile Ile Lys Asp Asp Ile Thr Asn Phe
1               5                   10                  15

Pro Leu Phe Ile Gly Lys Val Val Asn Pro Thr Gln Lys
            20                  25

<210> SEQ ID NO 16
<211> LENGTH: 29
<212> TYPE: PRT
<213> ORGANISM: Homo sapiens

<400> SEQUENCE: 16

Phe Asn Arg Pro Phe Leu Leu Leu Leu Trp Glu Val Thr Thr Gln Ser
1               5                   10                  15

Leu Leu Phe Leu Gly Lys Val Val Asn Pro Val Ala Gly
            20                  25

<210> SEQ ID NO 17
<211> LENGTH: 29
<212> TYPE: PRT
<213> ORGANISM: Homo sapiens

<400> SEQUENCE: 17

Ala Asn Arg Pro Phe Leu Val Phe Ile Arg Glu Val Pro Leu Asn Thr
1               5                   10                  15

Ile Ile Phe Met Gly Arg Val Ala Asn Pro Cys Val Lys
            20                  25

<210> SEQ ID NO 18
<211> LENGTH: 133
<212> TYPE: DNA
<213> ORGANISM: Homo sapiens
<220> FEATURE:
<221> NAME/KEY: CDS
<222> LOCATION: (23)..(118)

<400> SEQUENCE: 18
tgcattagtg gagacaagga cc att gtg cgt ttc aac agg ccc ttc ctg atg      52
                        Ile Val Arg Phe Asn Arg Pro Phe Leu Met
                        1               5                   10 atc att gtc cct aca gac acc cag aac atc ttc ttc atg agc aaa gtc     100
Ile Ile Val Pro Thr Asp Thr Gln Asn Ile Phe Phe Met Ser Lys Val
                15                  20                  25 acc aat ccc aag caa gcc tagagcttgc catca                             133
Thr Asn Pro Lys Gln Ala
            30

<210> SEQ ID NO 19
<211> LENGTH: 133
<212> TYPE: DNA
<213> ORGANISM: Homo sapiens

<400> SEQUENCE: 19
tgcattagtg gagacaagga ccattgtgcg tttcaacagg cccttcctga tgatcattgt     60
ccctacagac acccgaaaca tcttcttcat gagcaaagtc accaatccca agcaagccta   120
gagcttgcca tca                                                       133
```

-continued

```
<210> SEQ ID NO 20
<211> LENGTH: 133
<212> TYPE: DNA
<213> ORGANISM: Homo sapiens

<400> SEQUENCE: 20
tgcattagtg gagacaagga ccattgtgcg tttcaacagg cccttcctga tgatcattgt      60
ccctacagac acccagaaca tcttcttcat gagcaaagtc accaatccca agcaagccta    120
gagcttgcca tca                                                        133

<210> SEQ ID NO 21
<211> LENGTH: 98
<212> TYPE: DNA
<213> ORGANISM: Homo sapiens

<400> SEQUENCE: 21
ccccagaggt caagttcaac aaacccttt g tcttcttaat gattgaacaa ataccaagt      60 ctcccctctt catgggaaaa gtggtgaatc ccacccaa                              98

<210> SEQ ID NO 22
<211> LENGTH: 118
<212> TYPE: DNA
<213> ORGANISM: Homo sapiens

<400> SEQUENCE: 22
tgcccagacc aatcgccaca tcctgcgatt caaccggccc ttccttgtgg tgatcttttc      60
caccagcacc cagagtgtcc tctttctggg caaggtcgtc gaccccacga aaccatag      118

<210> SEQ ID NO 23
<211> LENGTH: 145
<212> TYPE: DNA
<213> ORGANISM: Homo sapiens

<400> SEQUENCE: 23
tgcccagacc aatcgccaca tcctgcgatt caaccggccc ttccttgtgg tgatcttttc      60
caccagcacc cagagtgtcc tctttctggg caaggtcgtc gaccccacga aaccatagcc    120
ctcccagggc tgctcatctg ttcca                                           145

<210> SEQ ID NO 24
<211> LENGTH: 103
<212> TYPE: DNA
<213> ORGANISM: Homo sapiens

<400> SEQUENCE: 24 tatcccccccc gaggtcaagt tcaacaaacc ctttgtcttc ttaatgattg aacaaaatac    60
caagtctccc ctcttcatgg gaaaagtggt gaatcccacc caa                      103

<210> SEQ ID NO 25
<211> LENGTH: 101
<212> TYPE: DNA
<213> ORGANISM: Homo sapiens

<400> SEQUENCE: 25
agtatcagac agtcatgttc aaccggccct tcctggtcat catcaaggat gacatcacca     60
actttccgct cttcattgga aaagtggtga atcccaccca a                        101

<210> SEQ ID NO 26
<211> LENGTH: 113
<212> TYPE: DNA
<213> ORGANISM: Homo sapiens
```

-continued

```
<400> SEQUENCE: 26
cccatctctg aacaccatgt cagacccaca tgcccacttc aacaggcctt tcctcttgct      60
cctttgggag gtcaccaccc agagcttact cttcctggga aaagttgtca acc            113

<210> SEQ ID NO 27
<211> LENGTH: 14
<212> TYPE: PRT
<213> ORGANISM: Rattus norvegicus

<400> SEQUENCE: 27

Ile Val Trp Phe Asn Arg Pro Phe Leu Ile Ala Val Ser His
1               5                   10

<210> SEQ ID NO 28
<211> LENGTH: 12
<212> TYPE: PRT
<213> ORGANISM: Rattus norvegicus

<400> SEQUENCE: 28

His Gly Gln Thr Ile Leu Phe Met Ala Lys Val Ile
1               5                   10
```